(12) United States Patent
Kishi et al.

(10) Patent No.: US 11,498,892 B2
(45) Date of Patent: Nov. 15, 2022

(54) FE/CU-MEDIATED KETONE SYNTHESIS

(71) Applicant: President and Fellows of Harvard College, Cambridge, MA (US)

(72) Inventors: Yoshito Kishi, Cambridge, MA (US); Kenzo Yahata, Osaka (JP); Vemula Praveen Kumar, Somerville, MA (US); Sudheer Babu Vaddela, Bellevue, WA (US)

(73) Assignee: President and Fellows of Harvard College, Cambridge, MA (US)

( * ) Notice: Subject to any disclaimer, the term of this patent is extended or adjusted under 35 U.S.C. 154(b) by 132 days.

(21) Appl. No.: 16/628,419

(22) PCT Filed: May 9, 2018

(86) PCT No.: PCT/US2018/031765
§ 371 (c)(1),
(2) Date: Jan. 3, 2020

(87) PCT Pub. No.: WO2019/009956
PCT Pub. Date: Jan. 10, 2019

(65) Prior Publication Data
US 2020/0165183 A1 May 28, 2020
US 2021/0179522 A9 Jun. 17, 2021

Related U.S. Application Data

(60) Provisional application No. 62/584,329, filed on Nov. 10, 2017, provisional application No. 62/529,326, filed on Jul. 6, 2017.

(30) Foreign Application Priority Data

Nov. 10, 2017 (JP) .............................. JP2017-217255

(51) Int. Cl.
C07C 45/45 (2006.01)
C07C 67/343 (2006.01)
(Continued)

(52) U.S. Cl.
CPC .......... C07C 45/455 (2013.01); C07C 67/343 (2013.01); C07C 69/738 (2013.01);
(Continued)

(58) Field of Classification Search
CPC ... C07C 45/455; C07C 67/343; C07C 69/738; C07D 307/20; C07D 319/06; C07D 309/10; C07F 7/1804
(Continued)

(56) References Cited

U.S. PATENT DOCUMENTS 5,338,865 A  8/1994  Kishi et al.
5,436,238 A  7/1995  Kishi et al.
(Continued)

FOREIGN PATENT DOCUMENTS

CO  2018008667 A2  8/2018
CO  2019009000 A2  1/2020
(Continued)

OTHER PUBLICATIONS

US 9,029,573 B2, 05/2015, Hu (withdrawn)
(Continued)

*Primary Examiner* — Taylor V Oh
(74) *Attorney, Agent, or Firm* — Wolf, Greenfield & Sacks, P.C.

(57) ABSTRACT

Provided herein are methods for preparing ketone-containing organic molecules. The methods are based on novel iron/copper-mediated ("Fe/Cu-mediated") coupling reactions. The Fe/Cu-mediated coupling reaction can be used in the preparation of complex molecules, such as halichondrins
(Continued)

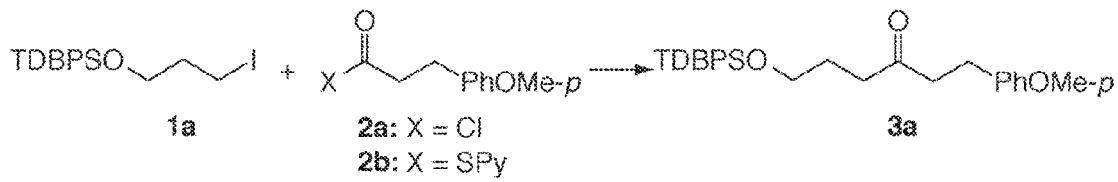

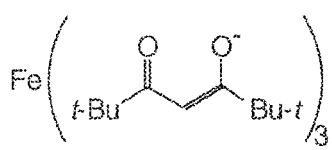

4: Fe(TMHD)$_3$

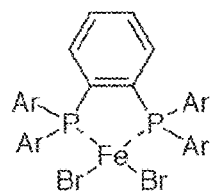

5a: FeBr$_2$(dppb): Ar = C$_6$H$_5$
5b: FeBr$_2$(SciOPP): Ar = C$_6$H$_3$(Bu-t)$_2$-3,5 and analogs thereof. In particular, the Fe/Cu-mediated ketolization reactions described herein are useful in the preparation of intermediates en route to halichondrins.

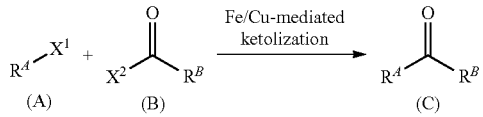

60 Claims, 7 Drawing Sheets

(51) Int. Cl.
  *C07D 307/20* (2006.01)
  *C07F 7/18* (2006.01)
  *C07C 69/738* (2006.01)
  *C07D 319/06* (2006.01)
  *C07D 309/10* (2006.01)
(52) U.S. Cl.
  CPC .......... *C07D 307/20* (2013.01); *C07D 309/10* (2013.01); *C07D 319/06* (2013.01); *C07F 7/1804* (2013.01)
(58) Field of Classification Search
  USPC .......................................... 549/214; 568/383
  See application file for complete search history.

(56) References Cited

U.S. PATENT DOCUMENTS

| | | |
|---|---|---|
| 5,786,492 A | 7/1998 | Gravalos et al. |
| 6,214,865 B1 | 4/2001 | Littlefield et al. |
| 6,469,182 B1 | 10/2002 | Littlefield et al. |
| 6,653,341 B1 | 11/2003 | Littlefield et al. |
| 7,470,720 B2 | 12/2008 | Littlefield et al. |
| 7,982,060 B2 | 7/2011 | Austad et al. |
| 8,093,410 B2 | 1/2012 | Chase et al. |
| 8,097,648 B2 | 1/2012 | Littlefield et al. |
| 8,203,010 B2 | 6/2012 | Endo et al. |
| 8,350,067 B2 | 1/2013 | Endo et al. |
| 8,445,701 B2 | 5/2013 | Austad et al. |
| 8,598,373 B2 | 12/2013 | Hu |
| 8,618,313 B2 | 12/2013 | Benayoud et al. |
| 8,884,031 B2 | 11/2014 | Chase et al. |
| RE45,324 E | 1/2015 | Austad et al. |
| 8,927,597 B2 | 1/2015 | Endo et al. |
| 8,975,422 B2 | 3/2015 | Fang et al. |
| 8,987,479 B2 | 3/2015 | Chase et al. |
| 9,206,194 B2 | 12/2015 | Hu |
| 9,278,979 B2 | 3/2016 | Souza et al. |
| 9,303,039 B2 | 4/2016 | Zhang et al. |
| 9,303,050 B2 | 4/2016 | Benayoud et al. |
| 9,382,262 B2 | 7/2016 | Endo et al. |
| 9,469,651 B2 | 10/2016 | Hu |
| 9,938,288 B1 | 4/2018 | Kishi et al. |
| 10,344,038 B2 | 7/2019 | Kishi et al. |
| 10,556,910 B2 | 2/2020 | Kishi et al. |
| 10,633,392 B2 | 4/2020 | Kishi et al. |
| 10,844,073 B2 | 11/2020 | Lee et al. |
| 10,954,249 B2 | 3/2021 | Kishi et al. |
| 11,155,562 B2 | 10/2021 | Kishi et al. |
| 11,220,513 B2 | 1/2022 | Kishi et al. |
| 2004/0198806 A1 | 10/2004 | Eisai et al. |
| 2006/0104984 A1 | 5/2006 | Littlefield et al. |
| 2006/0154312 A1 | 7/2006 | Agoulnik et al. |
| 2007/0244187 A1 | 10/2007 | Austad et al. |
| 2009/0198074 A1 | 8/2009 | Chase et al. |
| 2009/0203771 A1 | 8/2009 | Inanaga et al. |
| 2010/0254996 A1 | 10/2010 | Brantley-Sieders et al. |
| 2011/0054194 A1 | 3/2011 | Hu et al. |
| 2011/0184190 A1 | 7/2011 | Endo et al. |
| 2013/0336974 A1 | 12/2013 | Collier et al. |
| 2014/0198806 A1 | 7/2014 | Pani et al. |
| 2016/0090391 A1 | 3/2016 | Souza et al. |
| 2017/0137437 A1 | 5/2017 | Kishi et al. |
| 2018/0155361 A1 | 6/2018 | Lee et al. |
| 2018/0230164 A1 | 8/2018 | Kishi et al. |
| 2020/0002352 A1 | 1/2020 | Lee et al. |
| 2020/0148698 A1 | 5/2020 | Kishi et al. |
| 2020/0223863 A1 | 7/2020 | Kishi et al. |
| 2020/0325152 A1 | 10/2020 | Kishi et al. |
| 2021/0009605 A1 | 1/2021 | Kishi et al. |
| 2021/0230177 A1 | 7/2021 | Kishi et al. |
| 2021/0261566 A1 | 8/2021 | Kishi et al. |

FOREIGN PATENT DOCUMENTS

| | | |
|---|---|---|
| JP | S6-1191687 A | 8/1986 |
| JP | 6-122687 | 5/1994 |
| JP | 6-279450 | 10/1994 |
| JP | 6-279451 A | 10/1994 |
| JP | H07-504664 A | 5/1995 |
| JP | H08-208600 A | 8/1996 |
| JP | 2001-305734 A | 11/2001 |
| JP | 2003-261447 A | 9/2003 |
| RU | 2517167 C2 | 5/2014 |
| WO | WO 1993/017690 A1 | 9/1993 |
| WO | WO 1999/065894 A1 | 12/1999 |
| WO | WO 2005/118565 A1 | 12/2005 |
| WO | WO 2006/076100 A2 | 7/2006 |
| WO | WO 2007/139149 A1 | 12/2007 |
| WO | WO 2009/046308 A1 | 4/2009 |
| WO | WO 2009/064029 A1 | 5/2009 |
| WO | WO 2009/124237 A1 | 10/2009 |
| WO | WO 2011/094339 A1 | 8/2011 |
| WO | WO 2012/147900 A1 | 11/2012 |
| WO | WO 2013/086634 A1 | 6/2013 |
| WO | WO 2013/097042 A1 | 7/2013 |
| WO | WO 2013/142999 A1 | 10/2013 |
| WO | WO 2015/000070 A1 | 1/2015 |
| WO | WO 2015/066729 A1 | 5/2015 |
| WO | WO 2015/085193 A1 | 6/2015 |
| WO | WO 2016/003975 A1 | 1/2016 |
| WO | WO 2016/038624 A1 | 3/2016 |
| WO | WO 2016/176560 A1 | 11/2016 |
| WO | WO 2016/179607 A1 | 11/2016 |
| WO | WO 2017/151979 A1 | 9/2017 |
| WO | WO 2018/149552 A1 | 8/2018 |
| WO | WO 2018/187331 A1 | 10/2018 |
| WO | WO 2019/009956 A1 | 1/2019 |
| WO | WO 2019/010363 A1 | 1/2019 |

OTHER PUBLICATIONS

Extended European Search Report for EP 15814059.0, dated Nov. 24, 2017.
International Search Report and Written Opinion for PCT/US2015/038439, dated Sep. 29, 2015.
International Preliminary Report on Patentability for PCT/US2015/038439, dated Jan. 12, 2017.
International Search Report and Written Opinion for PCT/US2016/030064, dated Aug. 8, 2016.
International Preliminary Report on Patentability for PCT/US2016/030064, dated Nov. 9, 2017.
International Search Report and Written Opinion for PCT/US2018/025887, dated Jun. 21, 2018.
International Preliminary Report on Patentability for Application No. PCT/US2018/025887 dated Oct. 17, 2019.
Invitation to Pay Additional Fees for PCT/US2018/041005, dated Sep. 14, 2018.
International Preliminary Report on Patentability for PCT/US2018/041005, dated Jan. 16, 2020.
Invitation to Pay Additional Fees for PCT/US2018/061250, dated Feb. 26, 2019.
International Search Report and Written Opinion for PCT/US2018/061250, dated Apr. 16, 2019.

(56) References Cited

OTHER PUBLICATIONS

International Search Report and Written Opinion for PCT/US2018/031765, dated Jul. 2, 2018.
International Preliminary Report on Patentability for PCT/US2018/031765, dated Jan. 16, 2020.
[No Author Listed] American Chemical Society. STN Database. Apr. 11, 2014. RN # 1583253-64-8.
[No Author Listed] Application for Product Designation Under the SAKIGAKE Designation System. Generic name E7130. Eisai Co., Ltd. Nov. 22, 2017.
[No Author Listed] Evidentiary Document for Applicability of E7130 to Designation Requirements. Eisai Co., Ltd. Nov. 22, 2017.
[No Author Listed] Overview Relating to the Suitability for Designation Requirements Under the SAKIGAKE Designation System. Generic name E7130. Eisai Co., Ltd.
Aicher et al., Synthetic studies towards halichondrins. Tetrahedron Lett. 1987;28(30):3463-66.
Aicher et al., Synthetic Studies towards Halichondrins: Synthesis of the C.27-C.38 Segment. Tetrahedron Lett. 1992;33(12):1549-52.
Aicher et al., Total synthesis of halichondrin B and norhalichondrin B. J. Am. Chem. Soc., 1992, 114 (8), pp. 3162-3164.
Austed et al., Commercial Manufacture of Halaven®: Chemoselective Transformations En Route to Structurally Complex Macrocyclic Ketones. Synlett 2013; 24(3): 333-337. doi: 10.1055/s-0032-1318026.
Berge et al., Pharmaceutical Salts. J. Pharmaceutical Sciences 1977;66(1):1-19.
Bringans, Studies on natural product derivatives : HIV therapies incorporating marine natural products. Dissertation. University of Canterbury, 2001.
Buszek et al., Synthetic Studies Towards Halichondrins: Synthesis of the Left Half of Halichondrins. Tetrahedron Lett. 1992;33:1553.
Chen et al., Ni(II)/Cr(II)-mediated coupling reaction: an asymmetric process. J. Org. Chem., 1995, 60 (17), pp. 5386-5387.
Choi et al., Asymmetric Ni(II)/Cr(II)-Mediated Coupling Reaction: Catalytic Process. Org. Lett., 2002, 4 (25), pp. 4435-4438. doi: 10.1021/ol026981x.
Choi et al., Synthetic studies on the marine natural product halichondrins. Pure Appl. Chem., 2003, vol. 75, No. 1, pp. 1-17.
Dong et al., New syntheses of E7389 C14-C35 and halichondrin C14-C38 building blocks: reductive cyclization and oxy-Michael cyclization approaches. J Am Chem Soc. Nov. 4, 2009;131(43):15642-6. doi: 10.1021/ja9058487.
Fang et al., Synthetic Studies Towards Halichondrins: Synthesis of the Left Halves of Norhalichondrins and Homohalichondrins. Tetrahedron Lett. 1992;33(12):1557-60.
Fukuyama et al., Application of a Rotor-Stator High-Shear System for Cr/Mn-Mediated Reactions in Eribulin Mesylate Synthesis. Org. Process Res. Dev., 2016, 20 (1), pp. 100-104. doi: 10.1021/acs.oprd.5b00383.
Fukuyama et al., Application of Continuous Flow for DIBAL-H Reduction and n-BuLi Mediated Coupling Reaction in the Synthesis of Eribulin Mesylate. Org. Process Res. Dev., 2016, 20 (2), pp. 503-509. doi: 10.1021/acs.oprd.5b00353.
Gould et al., Salt selection for basic drugs. International Journal of Pharmaceutics Nov. 1986;33(1-3):201-217. https://doi.org/10.1016/0378-5173(86)90055-4.
Guo et al., Toolbox approach to the search for effective ligands for catalytic asymmetric Cr-mediated coupling reactions. J Am Chem Soc. Oct. 28, 2009;131(42):15387-93. doi: 10.1021/ja905843e.
Hickford et al., Antitumour polyether macrolides: four new halichondrins from the New Zealand deep-water marine sponge *Lissodendoryx* sp. Bioorg Med Chem. Mar. 15, 2009;17(6):2199-203. doi: 10.1016/j.bmc.2008.10.093. Epub Nov. 19, 2008.
Hirata et al., Halichondrins—antitumor polyether macrolides from a marine sponge. Pure Appl. Chem., 1986, vol. 58, No. 5, pp. 701-710.
Jackson et al., A total synthesis of norhalichondrin B. Angew Chem Int Ed Engl. 2009;48(13):2346-50. doi: 10.1002/anie.200806111.

Kaburagi et al., Effective procedure for selective ammonolysis of monosubstituted oxiranes: application to E7389 synthesis. Tetrahedron Lett. 2007;48(51):8967-71.
Kim et al., New syntheses of E7389 C14-C35 and halichondrin C14-C38 building blocks: double-inversion approach. J Am Chem Soc. Nov. 4, 2009; 131(43):15636-41. doi: 10.1021/ja9058475.
Kress et al., Investigations of the intramolecular Ni(II)/Cr(II)-mediated coupling reaction: Application to the taxane ring system. Tetrahedron Letters 1993;34(38);6003-6.
Kumar et al., Fe/Cu-Mediated One-Pot Ketone Synthesis. Org Lett. May 19, 2017;19(10):2766-2769. doi: 10.1021/acs.orglett.7b01128. Epub May 10, 2017.
Li et al., Unified Synthesis of C1-C19 Building Blocks of Halichondrins via Selective Activation/Coupling of Polyhalogenated Nucleophiles in (Ni)/Cr-Mediated Reactions. J Am Chem Soc. May 20, 2015;137(19):6226-31. doi: 10.1021/jacs.5b03499. Epub May 11, 2015.
Lill, Studies on New Zealand marine natural products. Dissertation. University of Canterbury, 1999.
Liu et al., Catalytic enantioselective Cr-mediated propargylation: application to halichondrin synthesis. Org Lett. Oct. 15, 2009;11(20):4520-3. doi: 10.1021/ol9016595.
Liu et al., Dramatic improvement in catalyst loadings and molar ratios of coupling partners for Ni/Cr-mediated coupling reactions: heterobimetallic catalysts. J Am Chem Soc. Nov. 25, 2009;131(46):16678-80. doi: 10.1021/ja9079308.
Liu et al., Synthesis of Alcohols from m-Fluorophenylsulfones and Dialkylboranes: Application to the C14-C35 Building Block of E7389. Org. Lett., 2012, 14 (9), pp. 2262-2265. doi: 10.1021/ol300672q.
Namba et al., New catalytic cycle for couplings of aldehydes with organochromium reagents. Org Lett. Dec. 23, 2004;6(26):5031-3.
Narayan et al., Novel second generation analogs of eribulin. Part I: Compounds containing a lipophilic C32 side chain overcome P-glycoprotein susceptibility. Bioorg Med Chem Lett, Mar. 15, 2011;21(6):1630-3.
Narayan et al., Novel second generation analogs of eribulin. Part II: Orally available and active against resistant tumors in vivo. Bioorg Med Chem Lett, Mar. 15, 2011;21(6):1634-8.
Narayan et al., Novel second generation analogs of eribulin. Part III: Blood-brain barrier permeability and in vivo activity in a brain tumor model. Bioorg Med Chem Lett, Mar. 15, 2011;21(6):1639-43.
Ortega et al., Potential clinical applications of halichondrins in breast cancer and other neoplasms. Breast Cancer (Dove Med Press). Feb. 8, 2012;4:9-19. doi: 10.2147/BCTT.S12423.
Seletsky et al., Structurally simplified macrolactone analogues of halichondrin B. Bioorg Med Chem Lett, Nov. 15, 2004;14(22):5547-50.
Shan et al., Concise and Highly Stereoselective Synthesis of the C20-C26 Building Block of Halichondrins and Eribulin. Org. Lett., 2012, 14 (2), pp. 660-663. doi: 10.1021/ol203373d.
Stamos et al., Ni(II)/Cr(II)-Mediated Coupling Reaction: Beneficial Effects of 4-tert-Butylpyridine as an Additive and Development of New and Improved Workup Procedures. Tetrahedron Lett. 1997;38(36):6355-8.
Stamos et al., Synthetic studies on halichondrins: A practical synthesis of the C.1☐C.13 segment. Tetrahedron Letters Nov. 25, 1996;37(48):8643-8646.
Ueda et al., Total synthesis of halichondrin A, the missing member in the halichondrin class of natural products. J Am Chem Soc. Apr. 2, 2014;136(13):5171-6. doi: 10.1021/ja5013307. Epub Mar. 19, 2014.
Uemura et al., Norhalichondrin A: an antitumor polyether macrolide from a marine sponge. J. Am. Chem. Soc., 1985, 107 (16), pp. 4796-4798. doi: 10.1021/ja00302a042.
Uemura, Exploratory research on bioactive natural products with a focus on biological phenomena. Proc Jpn Acad Ser B Phys Biol Sci. 2010;86(3):190-201.
Wan et al., Asymmetric Ni(II)/Cr(II)-mediated coupling reaction: stoichiometric process. Org Lett. Dec. 12, 2002;4(25):4431-4.
Wang et al., Structure-activity relationships of Halichondrin B analogues: modifications at C.30-C.38. Bioorg Med Chem Lett, May 15, 2000;10(10):1029-32.

(56) References Cited

OTHER PUBLICATIONS

Xie et al., Synthesis of the C20-C26 Building Block of Halichondrins via a Regiospecific and Stereoselective SN2' Reaction. Org. Lett., 2002;4(25):4427-1429.DOI: 10.1021/ol026982p.
Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.
Yamamoto et al., Total synthesis of halichondrin C. J Am Chem Soc. Jan. 18, 2012;134(2):893-6. doi: 10.1021/ja2108307. Epub Dec. 23, 2011.
Yan et al., Selective Activation/Coupling of Polyhalogenated Nucleophiles in Ni/Cr-Mediated Reactions: Synthesis of C1-C19 Building Block of Halichondrin Bs. J. Am. Chem. Soc., 2015, 137 (19), pp. 6219-6225.
Zheng et al., Macrocyclic ketone analogues of halichondrin B. Bioorg Med Chem Lett. Nov. 15, 2004;14(22):5551-4.
International Preliminary Report on Patentability for PCT/US2018/061250, dated May 28, 2020.
Araki et al., A Convenient Method for the Preparation of Ketones by the Reaction of Grignard Reagents with Carboxylic Acid Derivatives. Chem. Soc. Jpn. 1974;47:1777-80.
Britovsek et al., Synthesis of iron(ii), manganese(ii) cobalt(ii) and ruthenium(ii) complexes containing tridentate nitrogenligands and their application in the catalytic oxidation of alkanes. Dalton Trans. 2005, 945-55.
Buchwald et al., Synthesis, structure, and reactions of (1-ethoxyethyl)zirconocene chloride, a stable acyclic secondary zirconocene alkyl. Organometallics. 1988;7(11):2324-2328.
Cardellicchio et al., A highly efficient synthetic route to ketones through sequential coupling reactions of grignard reagents with s-phenyl carbonochloridothioate in the presence of nickel or iron catalysts. Tetrahedron Lett. 1985;26(30):3595-98.
Chen et al., Attempts to Improve the Overall Stereoselectivity of the Ireland-Claisen Rearrangement. Org. Lett. Jan. 15, 2009; 11(2):409-12.
Corey et al., Synthesis of 1,n-Dicarbonyl Derivates Using Carbanions from 1,3-Dithianes. Angew. Chem. Int. Ed. 1965;4(12):1077-78.
Dieter, Reaction of acyl chlorides with organometallic reagents: A banquet table of metals for ketone synthesis. Tetrahedron. 1999;55:4177-4236.
Eliel et al., Conformational analysis. 42. Monosubstituted tetrahydropyrans. J. Am. Chem. Soc. 1982; 104(13):3635-43.
Fiandanese et al., One-step synthesis of ketones from carylic acids and grignard reagents in the presence of a nickel(II)-phosphine catalyst. Tetrahedron Lett. 1983;24(34):3677-80.
Fleming et al., Grignard Reagents: Alkoxide-Directed Iodine-Magnesium Exchange at sp3 Centers. Org. Lett. 2007; 9(22):4507-09.
Gerlach et al., Bildung von Estern und Lactonen durch Silberionen-Katalyse. Helv. Chim. Acta. 1974; 57(8): 2661-63.
Hayashi et al., Diarylprolinol in an Asymmetric, Direct Cross-Aldol Reaction with Alkynyl Aldehydes. ChemCatChem. 2013; 5:2887-92.
Hayashi et al., A diarylprolinol in an asymmetric, catalytic, and direct crossed-aldol reaction of acetaldehyde. Angew Chem Int Ed Engl. 2008;47(11):2082-4. doi: 10.1002/anie.200704870.
Hoveyda et al., The remarkable metal-catalysed olefin metathesis reaction. Nature. 2007;450:243-51.
Johannes et al., Biomimetic macrocycle-forming Diels-Alder reaction of an iminium dienophile: synthetic studies directed toward gymnodimine. Org Lett. Sep. 1, 2005;7(18):3997-4000. doi: 10.1021/ol051553n.
Jung et al., Synthesis of 1,4-, 2,4-, and 3,4-dimethylphenanthrenes: a novel deoxygenation of arene 1,4-endoxides with trimethylsilyl iodide. J. Org. Chem. 1989; 54:5667-75.
Kaburagi, Operationally Simple and Efficient Workup Procedure for TBAF-Mediated Desilylation: Application to Halichondrin Synthesis. Org. Lett. 2007; 9(4):723-26.

Katsuki et al., The first practical method for asymmetric epoxidation. J. Am. Chem. Soc. 1980, 102(18) 5974-76.
Kim et al., Copper ion promoted esterification of (S)-2-pyridyl thioates and 2-pyridyl esters. Efficient methods for the preparation of hindered esters. J. Org. Chem. 1984;49(10):1712-16.
Knochel et al., Modern Organocopper Chemistry. 2002. Wiley-VCH, Eds.
Kobayashi et al., Complete Stereochemistry of Tetrafibricin. Org. Lett. 2003; 5(1):93-96.
Lee et al., Extension of Pd-Mediated One-Pot Ketone Synthesis to Macrocyclization: Application to a New Convergent Synthesis of Eribulinv. J. Am. Chem. Soc. 2016; 138(50):16248-51.
Lewis et al., Highly stereoselective approaches to .alpha.- and .beta.-C-glycopyranosides. J. Am. Chem. Soc. 1982;104(18):4976-78.
Li et al., Stereocontrolled Synthesis of β-Amino-α'-alkoxy Ketones by a Copper-Catalyzed Cross-Coupling of Peptidic Thiol Esters and α-Alkoxy alkylstannanes. Org. Lett. 2011; 13(14):3682-85.
Liebeskind et al., Thiol Ester-Boronic Acid Coupling. A Mechanistically Unprecedented and General Ketone Synthesis. J. Am. Chem. Soc. 2000;122(45):11260-61.
Lipschutz, Applications of Higher-Order Mixed Organocuprates to Organic Synthesis. Synthesis. Apr. 1987:325-41.
Loots et al., Nickel-catalyzed conjugate addition of zirconium alkenyls to . alpha., .beta.-unsaturated ketones. J. Am. Chem. Soc. 1977;99(24):8045-46.
Lu et al., Alkyl-Alkyl Suzuki Cross-Coupling of Unactivated Secondary Alkyl Chlorides. C. Angew. Chem. Int. Ed. 2010;49(37):6676-78.
Masashi et al., A Convenient Method for the Preparation of Ketones by the Reaction of Grignard Reagents with Carboxylic Acid Derivatives. Chem. Soc. Jpn. 1974;47:1777-80.
McGee et al., Synthesis and Isolation of Organogold Complexes through a Controlled 1,2-Silyl Migration. Chem. Eur. J. 2015;21(27): 9662-9665.
Miyajima et al., Electric-field-responsive handle for large-area orientation of discotic liquid-crystalline molecules in millimeter-thick films. Angew. Chem., Int. Ed. 2011;123:8011-15.
Nahm et al., N-methoxy-n-methylamides as effective acylating agents. Tetrahedron Lett. 1981;22(39):3815-18.
Negishi et al., Palladium-catalyzed acylation of organozincs and other organometallics as a convenient route to ketones. Tetrahedron Lett. 1983;24(47): 5181-4.
Negri et al., A total synthesis of polyether antibiotic (-)-A23187 (calcimycin). Tetrahedron Lett. 1987; 28(10):1063-66.
Normant, Organocopper(I) Compounds and Organocuprates in Synthesis. Synthesis. Feb. 1972; 1972(2):63-80.
Onaka et al., A Convenient Method for the Direct Preparation of Ketones From 2-(6-(2-Methoxyethyl)Pyridyl)Carboxylates and Alkyl Iodides by Use of Zinc Dust and a Catalytic Amount of Nickel Dichloride. Chem. Lett. 1981;10(4):531-34.
Ruscoe et al., Copper-Catalyzed Double Additions and Radical Cyclization Cascades in the Re-Engineering of the Antibacterial Pleuromutilin. J. Chem. Eur. J. 2016; 22:116-119.
Schrock, Multiple Metal-Carbon Bonds for Catalytic Metathesis Reactions. Adv. Synth Catal. 2007;349: 41-53.
Scriven et al., Azides: their preparation and synthetic uses. Chem Rev. 1988;88(2):297-368.
Seebach, Methods of Reactivity Umpolung. Angew. Chem. Int. Ed. 1979;18(4):239-58.
Seebach et al., Generation and synthetic applications of 2-lithio-1,3-dithianes. J. Org. Chem. 1975;40(2): 231-37.
Serrano et al., Nickel-Catalyzed Reductive Amidation of Unactivated Alkyl Bromides. Angew. Chem. Int. Ed. 2016;55(37):11207-11.
Sharpless et al., High stereo- and regioselectivities in the transition metal catalyzed epoxidations of olefinic alcohols by tert-butyl hydroperoxide. J. Am. Chem. Soc. 1973;95(18):6136-37.
Shiina, An Adventurous Synthetic Journey with MNBA from Its Reaction Chemistry to the Total Synthesis of Natural Products. Bull Chem. Soc. Jpn. 2014; 87(2):196-233.
Shiina et al., A novel and efficient macrolactonization of ω-hydroxycarboxylic acids using 2-methyl-6-nitrobenzoic anhydride (MNBA). Tetrahedron Lett. Oct. 14, 2002;43(42):7535-39.

(56) References Cited

OTHER PUBLICATIONS

Shiina et al., A Novel Method for the Preparation of Macrolides from ω-Hydroxycarboxylic Acids. Chem. Lett. 1994;23(4):677-80.
Smith III et al., Evolution of Dithiane-Based Strategies for the Construction of Architecturally Complex Natural Products. Acc. Chem. Rev. 2004; 37(6): 365-77.
Takai et al., A practical transformation of aldehydes into (E)-iodoalkenes with geminal dichromium reagents. Synlett. 1999;8:1268-70.
Takai et al., Simple and selective method for aldehydes (RCHO) → (E)-haloalkenes (RCH:CHX) conversion by means of a haloform-chromous chloride system. J. Am. Chem. Soc. 1986;108(23):7408-10.
Takaya et al., Investigation of Organoiron Catalysis in Kumada-Tamao-Corriu-Type Cross-Coupling Reaction Assisted by Solution-Phase X-ray Absorption Spectroscopy. Bull. Chem. Soc. Jpn. 2015;88(3): 410-418.
Takuji et al., Kumada-Tamao-Corriu Coupling of Alkyl Halides Catalyzed by an Iron-Bisphosphine Complex. Chem. Lett. 2011, 40(9):1030-32.
Thornton et al., π-Nucleophile Traps for Metallonitrene/Alkyne Cascade Reactions: A Versatile Process for the Synthesis of α-Aminocyclopropanes and β-Aminostyrenes. J. Am. Chem. Soc. 2009;131(7): 2434-2435.
Trnka et al., The Development of L2X2RuCHR Olefin Metathesis Catalysts: An Organometallic Success Story. Acc. Chem. Res. 2001;34(1):18-29.
Turhanen et al., A powerful tool for acid catalyzed organic addition and substitution reactions. RSC Adv. 2015; 5:26218-26222.
Velder et al., Modular Synthesis of Chiral Phosphine-Phosphite-Ligands from Phenolic Precursors: A New Approach to Bidentate Chelate Ligands Exploiting a P☐O to P☐C Migration Rearrangement. Adv Synth Catal. 2008; 350(9):1309-15.
Weix et al., Nickel-Catalyzed Cross-Electrophile Coupling with Organic Reductants in Non-Amide Solvents. Chem. Eur. J. 2016; 22(33):11564-11567.
Williams et al., Competitive oxidation processes in the reaction between (dicyclopentadienyl)zirconium bis(phosphine) complexes and alkyl halides. J. Am. Chem. Soc. 1980; 102(10):3660-62.
Williams et al., Direct observation of metal-centered radicals in an oxidative-addition reaction. J. Am. Chem. Soc. 1982; 104(4):1122-24.
Wipf et al., Transmetalation reactions of alkylzirconocenes: copper-catalyzed conjugate addition to enones. J. Org. Chem. 1991;56(23): 6494-96.
Wittenberg et al., Ketone synthesis under neutral conditions. Cu(I) diphenylphosphinate-mediated, palladium-catalyzed coupling of thiol esters and organostannanes. Org Lett. Aug. 21, 2003;5(17):3033-5. doi: 10.1021/ol034962x.
Wu et al., Ketone Formation via Mild Nickel-Catalyzed Reductive Coupling of Alkyl Halides with Aryl Acid Chlorides. Org. Lett. 2012; 14(12):3044-47.
Yoneda et al., Asymmetric Synthesis of Spiroketals with Aminothiourea Catalysts. Angew Chem Int Ed Engl. Dec. 14, 2015;54(51):15497-500. doi: 10.1002/anie.201508405.
Yus et al., The role of 1,3-dithianes in natural product synthesis. Tetrahedron. Aug. 11, 2003;59(33):6147-6212.
Zhang et al., Alcohols as Latent Coupling Fragments for Metallaphotoredox Catalysis: sp3-sp2 Cross-Coupling of Oxalates with Aryl Halides. J. Am. Chem. Soc. 2016; 138(42):13862-65.
Zhang et al., A Unique Catalyst Effects the Rapid Room-Temperature Cross-Coupling of Organozinc Reagents with Carboxylic Acid Fluorides, Chlorides, Anhydrides, and Thioesters. J. Am. Chem. Soc. 2004; 126(49):15964-65.
Zhao et al., Ni-Catalyzed Reductive Coupling of Alkyl Acids with Unactivated Tertiary Alkyl and Glycosyl Halides. J. Am. Chem. Soc. 2014;136(50):17645-51.
U.S. Appl. No. 15/322,756, filed Dec. 29, 2016, Kishi et al.
U.S. Appl. No. 16/746,233, filed Jan. 17, 2020, Kishi et al.
U.S. Appl. No. 15/570,593, filed Oct. 30, 2017, Kishi et al.
U.S. Appl. No. 16/441,843, filed Jun. 14, 2019, Kishi et al.
U.S. Appl. No. 15/814,105, filed Nov. 15, 2017, Kishi et al.
U.S. Appl. No. 16/500,924, filed Oct. 4, 2019, Kishi et al.
U.S. Appl. No. 16/628,504, filed Jan. 3, 2020, Kishi et al.
U.S. Appl. No. 15/809,845, filed Nov. 10, 2017, Lee et al.
U.S. Appl. No. 16/459,120, filed Jul. 1, 2019, Lee et al.
PCT/US2015/038439, Sep. 29, 2015, International Search Report and Written Opinion.
PCT/US2015/038439, Jan. 12, 2017, International Preliminary Report on Patentability.
EP 15814059.0, Nov. 24, 2017, Extended European Search Report.
PCT/US2016/030064, Nov. 9, 2017, International Preliminary Report on Patentability.
PCT/US2016/030064, Aug. 8, 2016, International Search Report and Written Opinion.
PCT/US2018/025887, Jun. 21, 2018, International Search Report and Written Opinion.
PCT/US2018/025887, Oct. 17, 2019, International Preliminary Report on Patentability.
PCT/US2018/04100, Sep. 14, 2018, Invitation to Pay Additional Fees.
PCT/US2018/04100, Jan. 16, 2020, International Preliminary Report on Patentability.
PCT/US2018/061250, Feb. 26, 2019, Invitation to Pay Additional Fees.
PCT/US2018/061250, Apr. 16, 2019, International Search Report and Written Opinion.
PCT/US2018/031765, Jul. 2, 2018, International Search Report and Written Opinion.
PCT/US2018/031765, Jan. 16, 2020, International Preliminary Report on Patentability.
International Search Report and Written Opinion for PCT/US2020/043501, dated Dec. 3, 2020.
Bockus et al. Form and Function in Cyclic Peptide Natural Products: A Pharmacokinetic Perspective. CurrTop Med Chem. 2013;13(7):821-36. doi: 10.2174/1568026611313070005.
Dybdal-Hargreaves et al. Eribulin Mesylate: Mechanism of Action of a Unique Microtubule-Targeting Agent. Clin Cancer Res. Jun. 1, 2015;21(11):2445-52. doi: 10.1158/1078-0432.CCR-14-3252. Epub Apr. 2, 2015.
Horita et al. Synthetic Studies of Halichondrin B, an Antitumor Polyether Macrolide Isolated from a Marine Sponge. 7. Synthesis of Two C27-C36 Units via Construction of the F Ring and Completely Stereoselective C-Glycosylation Using Mixed Lewis Acids. Chemical & Pharmaceutical Bulletin. 1997; 45(10): 1558-1572. doi:10. 1248/cpb.45.1558.
Jackson et al. The Halichondrins and E7389. Chem Rev. Jul. 2009;109(7):3044-79. doi: 10.1021/cr900016w.
Mori et al. Pd(OH)2/C (Pearlman's catalyst): a highly active catalyst for Fukuyama, Sonogashira, and Suzuki coupling reactions. J Org Chem. Feb. 21, 2003;68(4):1571-4. doi: 10.1021/jo0265277.
Mori et al. A novel procedure for the synthesis of multifunctional ketones through the Fukuyama coupling reaction employing dialkylzincs. Tetrahedron Letters. Sep. 20, 2004;45(39):7343-45.
Mori et al. Synthesis of Multi-Functionalized Ketones Through the Fukuyama Coupling Reaction Catalyzed by Pearlman's Catalyst: Preparation of Ethyl 6-Oxotridecanoate (Tridecanoic Acid, 6-Oxo-, Ethyl Ester).Organic Syntheses. 2007;84: 285-294.
Movassaghi et al. Enantioselective total synthesis of (-)-acylfulvene and (-)-irofulven. Angew Chem Int Ed Engl. Sep. 4, 2006;45(35):5859-63. doi: 10.1002/anie.200602011.
Swami et al. Eribulin in Cancer Treatment. Mar Drugs. Aug. 7, 2015;13(8):5016-58. doi: 10.3390/md13085016.
Ueda et al. Total synthesis of (+)-haplophytine. Angew Chem Int Ed Engl. 2009;48(41):7600-3. doi: 10.1002/anie.200902192.
Umehara et al. Further Studies on Ni/Zr-mediated One-pot Ketone Synthesis: Use of a 1-6 Mixture of NiI- and NiII-catalysts Greatly Improves the Molar Ratio of Coupling Partners. Chem Lett. 2019;48:947-950.
U.S. Appl. No. 17/501,037, filed Oct. 14, 2021, Kishi et al.
International Search Report and Written Opinion for PCT/US2018/041005, dated Nov. 19, 2018.
Durnov et al., Pediatric Oncology. Moscow Medicine. 2002; 139.

(56) References Cited

OTHER PUBLICATIONS

Kaburagi et al., Gram-Scale Synthesis of a Halichondrin-Class Anticancer Drug Candidate E7130. Abstract. Japanese language. 2021. 5 pages.

Kaburagi et al., Gram-Scale Synthesis of a Halichondrin-Class Anticancer Drug Candidate E7130. Abstract. English language. 2021. 2 pages.

Kaburagi, A landmark in drug discovery based on complex natural product synthesis. Abstract. 2021. 1 page.

Kira, Gram-scale synthesis of a structurally complex drug candidate E7130. Abstract. 2021. 1 page.

Kümmerer, Pharmaceuticals in the environment. Annu Rev Environ Resour. 2010;35:57-75.

No Author Listed, Presentation material for the 63rd Symposium on the Chemistry of Natural Products. Sep. 15-17, 2021. 26 pages.

No Author Listed, Small Medical Encyclopedia. Soviet Medicine. 1996; 5: 90-96.

Sabitha et al., Synthesis of the C45-C53 tetrahydropyran domain of norhalichondrins and the C14-C22 tetrahydrofuran domain of the halichondrin family. RSC Advances. 2012; 2: 10157-10159.

Melzig et al., Preparation of Polyfunctional Zinc Organometallics Using an Fe- or Co-Catalyzed Cl/Zn-Exchange, Org Lett. 2011; 13(12): 3174-3177.

Ogawa et al., Total synthesis of resolvin E1. Tetrahedron Letters. Nov. 4, 2009; 50(44): 6079-82.

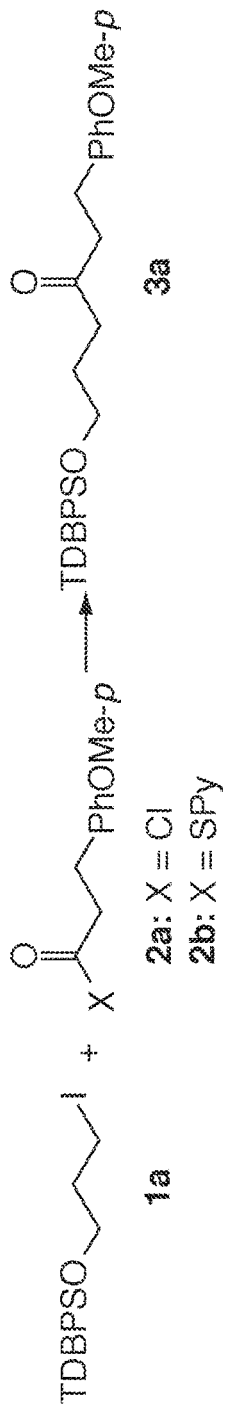
Figure 1A
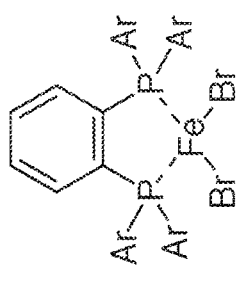
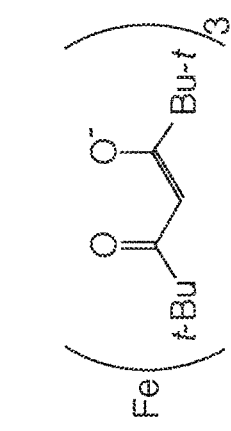
Figure 1B

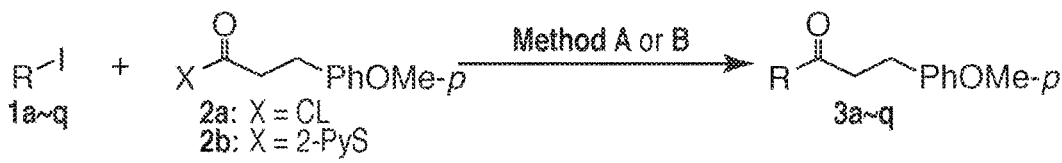

Method A: 2a (3.0 equiv.), 1a~q (1.0 equiv.), Fe(TMHD)$_3$ (10 mol%), CuCl$_2$ (1 equiv.), LiCl (3 equiv.), Mn (2.0 equiv.), DME (C 0.4 M), 0 °C, 15 hr
Method B-1: 2a (1.0 equiv.), 1a~q (1.2 equiv.), FeBr$_2$(dppb) (5 mol%), CuCl$_2$ (1.0 equiv.), LiCl (3 equiv.), Mn (2.0 equiv.), DME (C 0.4 M), 0 °C, 15 hr
B-2: 2a (1.2 equiv.), 1a~q (1.0 equiv.), others are same as Method B-1
Method C: 2b (1.2 equiv.), 1a~q (1.0 equiv.), FeBr$_2$(dppb) (5 mol%), CuI (1.0 equiv.), ZrCp$_2$Cl$_2$ (1.0 equiv.), LiCl (3 equiv.) Mn (2.0 equiv.), DME (C 0.4 M), 0 °C, 15hr

A. Steric Effects

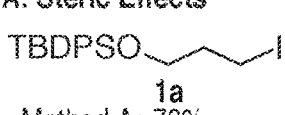
1a
Method A: 76%
Method B-1: 90%; B-2: 87%
Method C: 80%

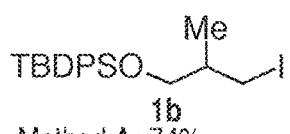
1b
Method A: 74%
Method B-1: 86%; B-2: 83%
Method C: 78%

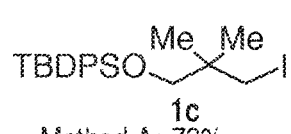
1c
Method A: 72%
Method B-1: 80%; B-2: 80%
Method C: 72%

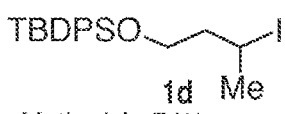
1d
Method A: 74%
Method B-1: 80%; B-2: 80%
Method C: 74%

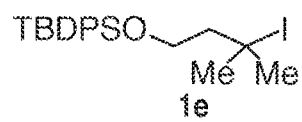
1e
Method A: no PD
Method B-1: no PD; B-2: no PD
Method C: no PD

B. Tolerance with Common Protecting Groups

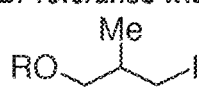

| | | | | |
|---|---|---|---|---|
| 1b: X = TBDPS | 1f: X = TBS | 1g: X = Bz | 1h: X = THP | 1i: X = MPM |
| Method A: 74% | Method A: 78% | Method A: 81% | Method A: 75% | Method A: 71% |
| Method B-1: 86% | Method B-1: 90% | Method B-1: 90% | Method B-1: 85% | Method B-1: 78% |
| B-2: 83% | B-2: 86% | B-2: 90% | B-2: 84% | B-2: 74% |
| Method C: 78% | Method C: 81% | Method C: 90% | Method C: 80% | Method C: 70% |

C. Differentiation from Vinyl and Aryl Halides and Other Groups

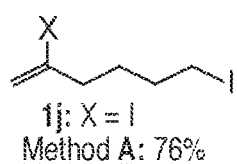
1j: X = I
Method A: 76%
Method B-1: 86%
B-2: 83%
Method C: 79%

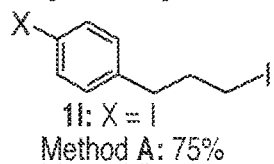
1l: X = I
Method A: 75%
Method B-1: 86%
B-2: 86%
Method C: 81%

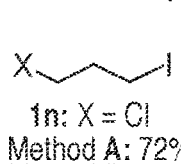
1n: X = Cl
Method A: 72%
Method B-1: 76%
B-2: 74%
Method C: 70%

1p: X = OH
Method A: 25%
Method B-1: 36%
B-2: 35%
Method C: 36%

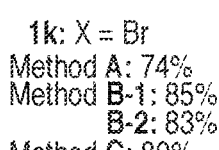
1k: X = Br
Method A: 74%
Method B-1: 85%
B-2: 83%
Method C: 80%

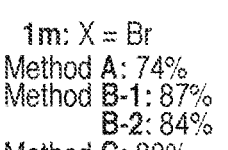
1m: X = Br
Method A: 74%
Method B-1: 87%
B-2: 84%
Method C: 80%

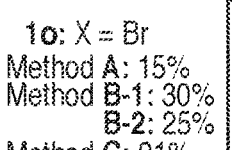
1o: X = Br
Method A: 15%
Method B-1: 30%
B-2: 25%
Method C: 21%

1q: R = −C≡C−TES
Method A: 75%
Method B-1: 86%
B-2: 82%
Method C: 78%

Figure 2

Coupling Condition:
9 or 12 (1.0 equiv.), 10 (1.2 equiv.), FeBr$_2$(SciOPP) (5 mol%), CuI (1.0 equiv.), ZrCp$_2$Cl$_2$ (1.0 equiv.), LiCl (3 equiv.), Mn (2.0 equiv.), DME (C 0.4 M), 0 °C, 15 hr

FE/CU-MEDIATED KETONE SYNTHESIS

RELATED APPLICATIONS

This application is a national stage filing under 35 U.S.C. § 371 of international PCT application, PCT/US2018/031765, filed May 9, 2018, which claims priority under 35 U.S.C. § 119(e) to U.S. Provisional Patent Applications, U.S. Ser. No. 62/529,326, filed Jul. 6, 2017, and U.S. Ser. No. 62/584,329, filed Nov. 10, 2017; and which also claims priority under 35 U.S.C. § 119(a) to Japanese Patent Application No. 2017-217255, filed Nov. 10, 2017; the entire contents of each of which is incorporated herein by reference.

BACKGROUND OF THE INVENTION

The addition of organometallic reagents to carboxylic acids or derivatives gives a simple solution for ketone synthesis. One drawback associated with this method is the fact that the desired ketones often react further with organometallic reagents. Weinreb ketone synthesis offers a solution to overcome this drawback. See, e.g., Nahm, S.; Weinreb, S. M. *Tetrahedron Lett.* 1981, 22, 3815. In recent years, it has been demonstrated that Ni- or Pd-mediated coupling of an activated form of carboxylic acid with organometallic offers an alternative solution. For a general review on ketone syntheses with organometallics, see, e.g., Dieter, R. K. *Tetrahedron* 1999, 55, 4177. For selected references for metal-catalyzed ketone syntheses, see: RMgX/Ni: Fiandanese, V.; Marchese, G.; Ronzini, L. *Tetrahedron Lett.* 1983, 24, 3677; RMgX/Ni and RMgX/Fe: Cardellicchio, C.; Fiandanese, V.; Marchese, G.; Ronzini, L. *Tetrahedron Lett.* 1985, 26, 3595 and references cited therein; RZnX/Pd: Negishi, E.-i.; Bagheri, V.; Chatterjee, S.; Luo, F.-T.; Miller, J. A.; Stoll, A. T. *Tetrahedron Lett.* 1983, 24, 5181; RSnX$_3$/Pd: Wittenberg, R.; Srogl, J.; Egi, M.; Liebeskind, L. S. *Org. Lett.* 2003, 5, 3033; RB(OH)$_2$/Pd: Liebeskind, L. S.; Srogl, J. *J. Am. Chem. Soc.* 2000, 122, 11260; RSnX$_3$/Cu: Li, H.; He, A.; Falck, J. R.; Liebeskind, L. S. *Org. Lett.* 2011, 13, 3682; R$_2$Zn/Ni: Zhang, Y.; Rovis, T. *J. Am. Chem. Soc.* 2004, 126, 15964.

New methods for the synthesis of ketones are needed, especially for use in the preparation of complex molecules, such as halichondrins and analogs thereof.

Halichondrins are polyether natural products, originally isolated from the marine scavenger Halichondria okadai by Uemura, Hirata, and coworkers. See, e.g., Uemura, D.; Takahashi, K.; Yamamoto, T.; Katayama, C.; Tanaka, J.; Okumura, Y.; Hirata, Y. *J. Am. Chem. Soc.* 1985, 107, 4796; Hirata, Y.; Uemura, D. *Pure Appl. Chem.* 1986, 58, 701. Several additional members, including halistatin, were isolated from various marine scavengers. This class of natural products displays interesting structural diversity, such as the oxidation state of the carbons of the C8-C14 polycycle, and the length of the carbon backbone. Thus, this class of natural products is sub-grouped into the norhalichondrin series (e.g., norhalichondrin A, B, and C), the halichondrin series (e.g., halichondrin A, B, C), and the homohalichondrin series (e.g., homohalichondrin A, B, C). Except halichondrin A, all the members have been isolated from natural sources. Due to their intriguing structural architecture and extraordinary antitumor activity, halichondrins have received much attention from the scientific community. The general structure of compounds in the halichondrin series (e.g., halichondrin A, B, C) is shown below. In the below structure, halichondrin A is when $R^Y$ and $R^X$ are both OH; halichondrin B is when $R^Y$ and $R^X$ are both hydrogen; and halichondrin C is when $R^X$ is OH, and $R^Y$ is hydrogen:

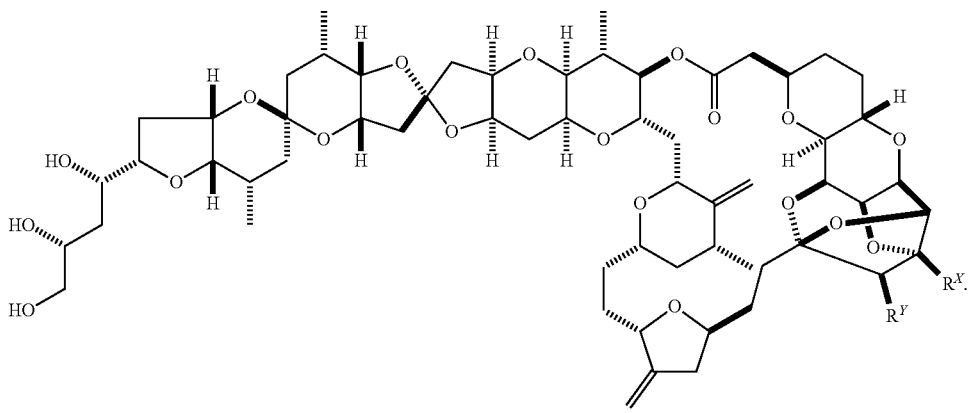

SUMMARY OF THE INVENTION

Provided herein are methods for preparing ketone-containing organic molecules. The methods are based on novel iron/copper-mediated ("Fe/Cu-mediated") coupling reactions. The Fe/Cu-mediated coupling reaction can be used in the preparation of complex molecules, such as halichondrins and analogs thereof. In particular, the Fe/Cu-mediated ketolization reactions described herein are useful in the preparation of intermediates en route to halichondrins. Therefore, the present invention also provides methods for the preparation of intermediates useful in the synthesis of halichondrins.

Additionally, provided herein are compounds, intermediates, reagents, ligands, catalysts, and kits useful in the coupling methods provided herein, as well as compounds (i.e., intermediates) useful in the preparation of halichondrins and analogs thereof.

In one aspect, the present invention provides methods for preparing ketones using a Fe/Cu-mediated coupling reaction, as outlined in Scheme 1A. The groups $R^A$, $X^1$, $X^2$, and $R^B$ are defined herein.

Scheme 1A

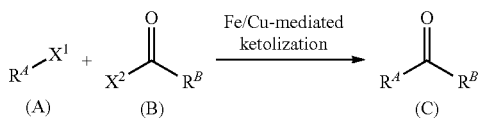

The coupling reactions provided herein can be used in the synthesis of ketone-containing compounds, such as intermediates en route to halichondrins (e.g., halichondrin A, B, C; homohalichondrin A, B, C; norhalichondrin A, B, C) and analogs thereof. Scheme 2 shows a Fe/Cu-mediated coupling reaction to yield a compound of Formula (I-13), which is an intermediate useful in the synthesis of halichondrins (e.g., halichondrin A, B, C), and analogs thereof. Groups $R^{P1}$, $R^{P2}$, $R^{P3}$, $R^{P5}$, $R^1$, $X^1$, $X^2$, $X^1$, $R^2$, $R^{P4}$, and $X^3$ are defined herein.

Scheme 2

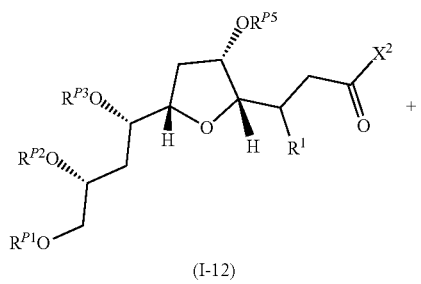

(I-12)

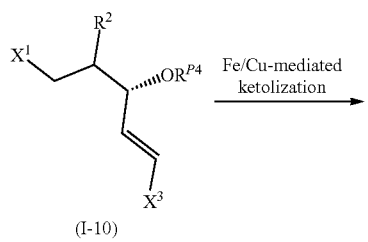

(I-10)

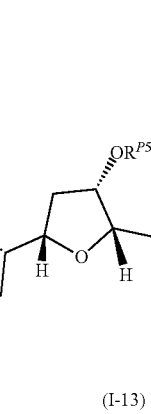

(I-13)

As another example, Scheme 3 shows a Fe/Cu-mediated coupling reaction to yield a compound of Formula (I-11), which is an intermediate useful in the synthesis of halichondrins and analogs thereof. Groups $R^{P6}$, $R^{P5}$, $R^1$, $X^2$, $X^1$, $R^2$, $R^{P4}$, $X^3$ are defined herein.

Scheme 3

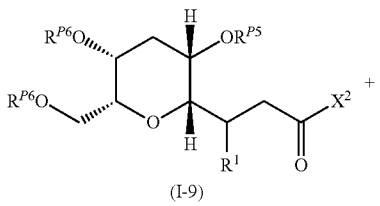

(I-9)

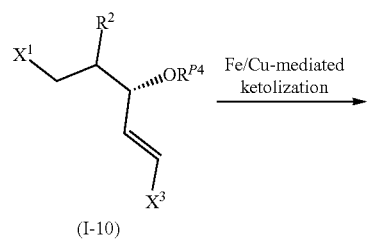

(I-10)

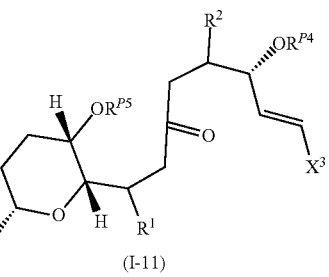

(I-11)

As yet another example, Scheme 4 shows a Fe/Cu-mediated coupling reaction to yield compounds of Formula (II-3), which are intermediates useful in the synthesis of halichondrins and analogs thereof (i.e., C20-C26 fragments of halichondrins). Groups $X^1$, $X^2$, $X^3$, $R^5$, and $R^8$ are as defined herein.

Scheme 4

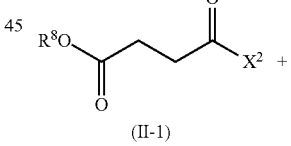

(II-1)

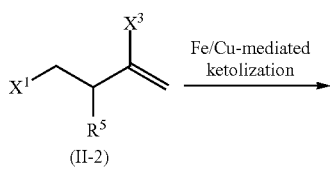

(II-2)

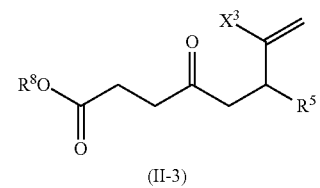

(II-3)

The C20-C26 carbons of compounds in the halichondrin series are denoted below.

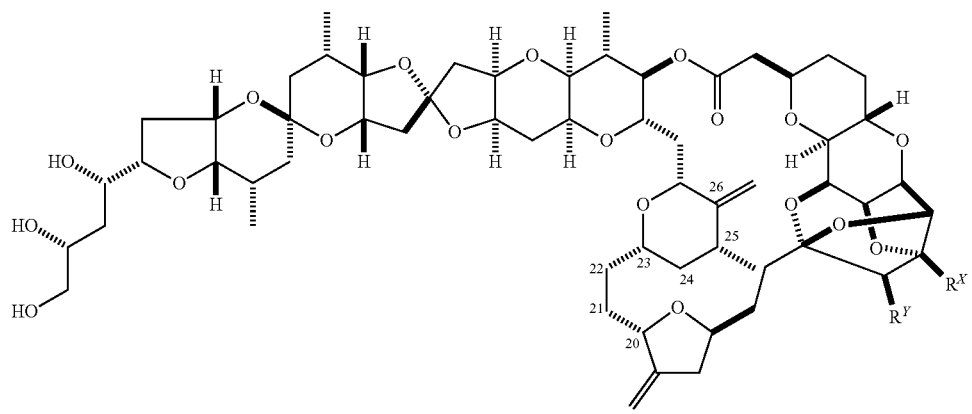

In certain embodiments, an advantage of the Fe/Cu-mediated couplings described herein over existing ketolization methods is that the novel Fe/Cu-mediated reactions allow for selective coupling of alkyl halides (e.g., alkyl iodides) in the presence of vinyl halides (e.g., vinyl iodides). Other ketone-forming coupling reactions, as well as methods for the synthesis of halichondrins, can be found in, for example, international PCT publications, WO 2016/176560, published Nov. 3, 2016, and WO 2016/003975, published Jan. 7, 2016; the entire contents of each of which is incorporated herein by reference.

One-pot ketone syntheses have been reported involving alkylzinc halides, prepared from alkyl halides via a single electron transfer (SET) process and were curious in extending this concept to the development of Cu-mediated one-pot ketone synthesis for two reasons. See, e.g., Lee, J. H.; Kishi, Y. *J. Am. Chem. Soc.*, 2016, 138, 7178. First, Cu-mediated one-pot ketone synthesis might exhibit a reactivity-profile different from Ni- and/or Pd-mediated one-pot ketone syntheses. Second, it is well recognized that over-addition of organometallic reagents is not the issue for cuprate-based ketone synthesis. For a review, see, e.g., Knochel, P.; Betzemeier, B. *Modern Organocopper Chemistry*, Wiley-VCH, 2002; Normant, J. F. Synthesis 1972, 63; Lipschutz, B. H. Synthesis 1987, 325.

The details of certain embodiments of the invention are set forth in the Detailed Description of Certain Embodiments, as described below. Other features, objects, and advantages of the invention will be apparent from the Definitions, Examples, Figures, and Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; *Smith and March, March's Advanced Organic Chemistry*, 5$^{th}$ Edition, John Wiley & Sons, Inc., New York, 2001; Larock, Comprehensive Organic Transformations, VCH Publishers, Inc., New York, 1989; and Carruthers, Some Modern Methods of Organic Synthesis, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., $CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., $CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include $CHF_2$, $CH_2F$, $CF_3$, $CH_2CF_3$, $CF_2CF_3$, $CF_2CF_2CF_3$, $CCl_3$, $CFCl_2$, $CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., $CH=CHCH_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —C$^A$H(C$^B$H$_2$C$^C$H$_3$)— includes one chain atom C$^A$, one hydrogen atom on C$^A$, and non-chain substituent —(C$^B$H$_2$C$^C$H$_3$). The term "C$_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

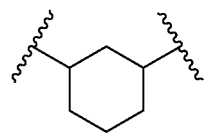 [SMILES: *C1CCCC(*)C1]

is a C$_3$ hydrocarbon chain. When a range of values is used, the meaning of the range is as described herein. For example, a C$_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C=C and/or C≡ bonds anywhere in the hydrocarbon chain. For instance, —CH=CH—(CH$_2$)$_2$—, —CH$_2$—C≡C—

CH$_2$—, and —C≡C—CH=CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

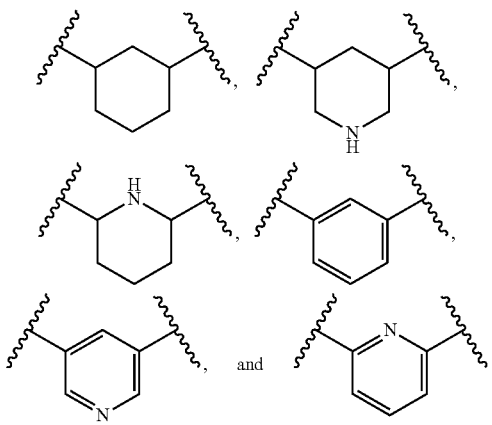

are all examples of a hydrocarbon chain. In contrast, in certain embodiments,

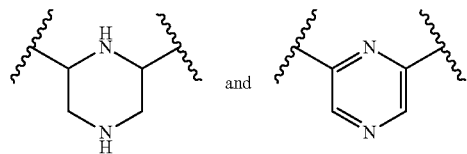 [SMILES: *C1CNCC(*)N1 ; *c1cncc(*)n1]

are not within the scope of the hydrocarbon chains described herein. When a chain atom of a C$_x$ hydrocarbon chain is replaced with a heteroatom, the resulting group is referred to as a C$_x$ hydrocarbon chain wherein a chain atom is replaced with a heteroatom, as opposed to a C$_{x-1}$ hydrocarbon chain. For example,

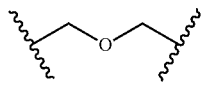

is a C$_3$ hydrocarbon chain wherein one chain atom is replaced with an oxygen atom.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 t electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$+X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S) SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N($R^{bb}$)$_2$)$_2$, —$NR^{bb}$P(=O)($R^{aa}$)$_2$, —$NR^{bb}$P(=O)(O$R^{cc}$)$_2$, —$NR^{bb}$P(=O)(N($R^{bb}$)$_2$)$_2$, —P($R^{cc}$)$_2$, —P(O$R^{cc}$)$_2$, —P($R^{cc}$)$_3$+X$^-$, —P(O$R^{cc}$)$_3$+X$^-$, —P($R^{cc}$)$_4$, —P(O$R^{cc}$)$_4$, —OP($R^{cc}$)$_2$, —OP($R^{cc}$)$_3$+X$^-$, —OP(O$R^{cc}$)$_2$, —OP(O$R^{cc}$)$_3$+X$^-$, —OP($R^{cc}$)$_4$, —OP(O$R^{cc}$)$_4$, —B($R^{aa}$)$_2$, —B(O$R^{cc}$)$_2$, —B$R^{aa}$(O$R^{cc}$), $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 Rdd groups; wherein X$^-$ is a counterion;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)($R^{aa}$)$_2$, —P(=O)(O$R^{cc}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein X$^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$+X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —NRfC(=O)$R^{ee}$, —NRCO$_2$Re$^e$, —N$R^{ff}$C(=O)N($R^{ff}$)$_2$, —C(=NRf)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)(O$R^{ee}$)$_2$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein X$^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2}$_6 alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3$+X$^-$, —NH($C_{1-6}$ alkyl)$_2$+X$^-$, —NH$_2$($C_{1-6}$ alkyl)+X$^-$, —NH$_3$+X$^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(=NH)NH($C_{1-6}$ alkyl), —OC(=NH)NH$_2$, —NHC(=NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$($C_{1-6}$ alkyl), —SO$_2$O($C_{1-6}$ alkyl), —OSO$_2$($C_{1-6}$ alkyl), —SO($C_{1-6}$ alkyl), —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_1$_6 alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

In certain embodiments, carbon atom substituents include: halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$+X$^-$, —NH(C$_{1-6}$ alkyl)$_2$+X$^-$, —NH$_2$(C$_{1-6}$ alkyl)+X$^-$, —NH$_3$+X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(=NH)NH(C$_{1-6}$ alkyl), —OC(=NH)NH$_2$, —NHC(=NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$(C$_{1-6}$ alkyl), —SO$_2$O(C$_{1-6}$ alkyl), —OSO$_2$(C$_{1-6}$ alkyl), —SO(C$_{1-6}$ alkyl), —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

In certain embodiments, substituents include: halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$+X$^-$, —NH(C$_{1-6}$ alkyl)$_2$+X$^-$, —NH$_2$(C$_{1-6}$ alkyl)+X$^-$, —NH$_3$+X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(=NH)NH(C$_{1-6}$ alkyl), —OC(=NH)NH$_2$, —NHC(=NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$(C$_{1-6}$ alkyl), —SO$_2$O(C$_{1-6}$ alkyl), —OSO$_2$(C$_{1-6}$ alkyl), —SO(C$_{1-6}$ alkyl), —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$+X$^-$, —OP(OR$^{cc}$)$_2$, —OP(OR$^{cc}$)$_3$+X$^-$, —OP(=O)(R$^{aa}$)$_2$, —OP(=O)(OR$^{cc}$)$_2$, and —OP(=O)(N(R$^{bb}$)$_2$)$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino.

In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$+X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, —C(=S)O(R$^{X1}$), —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO₂H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp² hybridized, and is substituted with an oxygen, nitrogen or sulfur atom, e.g., a group selected from ketones (e.g., —C(=O)$R^{aa}$), carboxylic acids (e.g., —CO₂H), aldehydes (—CHO), esters (e.g., —CO₂$R^{aa}$, —C(=O)$SR^{aa}$, —C(=S)$SR^{aa}$), amides (e.g., —C(=O)N($R^{bb}$)₂, —C(=O)$NR^{bb}SO_2R^{aa}$, —C(=S)N($R^{bb}$)₂), and imines (e.g., —C(=$NR^{bb}$)$R^{aa}$, —C(=$NR^{bb}$)$OR^{aa}$), —C(=$NR^{bb}$)N($R^{bb}$)₂), wherein $R^{aa}$ and $R^{bb}$ are as defined herein.

The term "silyl" refers to the group —Si($R^{aa}$)₃, wherein $R^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —N($R^{cc}$)₂, —CN, —C(=O)$R^{aa}$, —C(=O)N($R^{cc}$)₂, —CO₂$R^{aa}$, —SO₂$R^{aa}$, —C(=$NR^{bb}$)$R^{aa}$, —C(=$NR^{cc}$)$OR^{aa}$, —C(=$NR^{cc}$)N($R^{cc}$)₂, —SO₂N($R^{cc}$)₂, —SO₂$R^{cc}$, —SO₂OR, —$SOR^{aa}$, —C(=S)N($R^{cc}$)₂, —C(=O)$SR^{cc}$, —C(=S)$SR^{cc}$, —P(=O)(O$R^{cc}$)₂, —P(=O)($R^{aa}$)₂, —P(=O)(N($R^{cc}$)₂)₂, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —$OR^{aa}$, —N($R^{cc}$)₂, —C(=O)$R^{aa}$, —C(=O)N($R^{cc}$)₂, —CO₂$R^{aa}$, —SO₂$R^{aa}$, —C(=$NR^{cc}$)$R^{aa}$, —C(=$NR^{cc}$)$OR^{aa}$, —C(=$NR^{cc}$)N($R^{cc}$)₂, —SO₂N($R^{cc}$)₂, —SO₂$R^{cc}$, —SO₂$OR^{cc}$, —$SOR^{aa}$, —C(=S)N($R^{cc}$)₂, —C(=O)$SR^{cc}$, —C(=S)$SR^{cc}$, $C_{1-10}$ alkyl (e.g., aralkyl, heteroaralkyl), $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)$OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoboryl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$+X$^-$, —P(OR$^{cc}$)$_2$, —P(OR$^{cc}$)$_3$+X$^-$, —P(=O) (R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, o-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, —$R^{aa}$, —N($R^{bb}$)$_2$, —C(=O)S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P(Rcc)$_2$, —P($R^{cc}$)$_3$+X$^-$, —P(O$R^{cc}$)$_2$, —P(O$R^{cc}$)$_3$+X$^-$, —P(=O)($R^{aa}$)$_2$, —P(=O)(O$R^{cc}$)$_2$, and —P(=O)(N($R^{bb}$)$_2$)$_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference. In certain embodiments, a sulfur protecting group is acetamidomethyl, t-butyl, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate,—OTs), methanesulfonate (mesylate,—OMs), p-bromobenzenesulfonyloxy (brosylate,—OBs), —OS(=O)$_2$(CF$_2$)$_3$CF$_3$ (nonaflate,—ONf), or trifluoromethanesulfonate (triflate,—OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., —OC(=O)S$R^{aa}$, —OC(=O)$R^{aa}$, —OCO$_2R^{aa}$, —OC(=O)N($R^{bb}$)$_2$, —OC(=N$R^{bb}$)$R^{aa}$, —OC(=N$R^{bb}$)O$R^{aa}$, —OC(=N$R^{bb}$)N($R^{bb}$)$_2$, —OS(=O)$R^{aa}$, —OSO$_2R^{aa}$, —OP(RC)$_2$, —OP($R^{cc}$)$_3$, —OP(=O)$_2R^{aa}$, —OP(=O)($R^{aa}$)$_2$, —OP(=O)(O$R^{cc}$)$_2$, —OP(=O)$_2$N($R^{bb}$)$_2$, and —OP(=O)(N$R^{bb}$)$_2$, wherein $R^{aa}$, $R^{bb}$, and $R^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

The following definitions are more general terms used throughout the present application.

As used herein, the term "salt" refers to any and all salts, and encompasses pharmaceutically acceptable salts. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases.

Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium, and N+($C_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "small molecule" refers to molecules, whether naturally-occurring or artificially created (e.g., via chemical synthesis) that have a relatively low molecular weight.

Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)).

The term "catalysis," "catalyze," or "catalytic" refers to the increase in rate of a chemical reaction due to the participation of a substance called a "catalyst." In certain embodiments, the amount and nature of a catalyst remains essentially unchanged during a reaction. In certain embodiments, a catalyst is regenerated, or the nature of a catalyst is essentially restored after a reaction. A catalyst may participate in multiple chemical transformations. The effect of a catalyst may vary due to the presence of other substances known as inhibitors or poisons (which reduce the catalytic activity) or promoters (which increase the activity). Catalyzed reactions have lower activation energy (rate-limiting free energy of activation) than the corresponding uncatalyzed reaction, resulting in a higher reaction rate at the same temperature. Catalysts may affect the reaction environment favorably, bind to the reagents to polarize bonds, form specific intermediates that are not typically produced by a uncatalyzed reaction, or cause dissociation of reagents to reactive forms.

The term "solvent" refers to a substance that dissolves one or more solutes, resulting in a solution. A solvent may serve as a medium for any reaction or transformation described herein. The solvent may dissolve one or more reactants or reagents in a reaction mixture. The solvent may facilitate the mixing of one or more reagents or reactants in a reaction mixture. The solvent may also serve to increase or decrease the rate of a reaction relative to the reaction in a different solvent. Solvents can be polar or non-polar, protic or aprotic. Common organic solvents useful in the methods described herein include, but are not limited to, acetone, acetonitrile, benzene, benzonitrile, 1-butanol, 2-butanone, butyl acetate, tert-butyl methyl ether, carbon disulfide carbon tetrachloride, chlorobenzene, 1-chlorobutane, chloroform, cyclohexane, cyclopentane, 1,2-dichlorobenzene, 1,2-dichloroethane, dichloromethane (DCM), N,N-dimethylacetamide N,N-dimethylformamide (DMF), 1,3-dimethyl-3,4,5,6-tetrahydro-2-pyrimidinone (DMPU), 1,4-dioxane, 1,3-dioxane, diethylether, 2-ethoxyethyl ether, ethyl acetate, ethyl alcohol, ethylene glycol, dimethyl ether, heptane, n-hexane, hexanes, hexamethylphosphoramide (HMPA), 2-methoxyethanol, 2-methoxyethyl acetate, methyl alcohol, 2-methylbutane, 4-methyl-2-pentanone, 2-methyl-1-propanol, 2-methyl-2-propanol, 1-methyl-2-pyrrolidinone, dimethylsulfoxide (DMSO), nitromethane, 1-octanol, pentane, 3-pentanone, 1-propanol, 2-propanol, pyridine, tetrachloroethylene, tetrahyrdofuran (THF), 2-methyltetrahydrofuran, toluene, trichlorobenzene, 1,1,2-trichlorotrifluoroethane, 2,2,4-trimethylpentane, trimethylamine, triethylamine, N,N-diisopropylethylamine, diisopropylamine, water, o-xylene, and p-xylene.

BRIEF DESCRIPTION OF THE DRAWINGS

The accompanying drawings, which constitute a part of this specification, illustrate several embodiments of the invention and together with the description, serve to explain the principles of the invention.

FIG. 1A outlines exemplary coupling reactions to form ketones. FIG. 1B shows exemplary iron catalysts useful in the Fe/Cu-mediated coupling reactions described herein.

FIG. 2 shows exemplary Fe/Cu-mediated coupling reactions to form ketones using a wide array of substrates.

DETAILED DESCRIPTION OF CERTAIN EMBODIMENTS

Figure 1C:
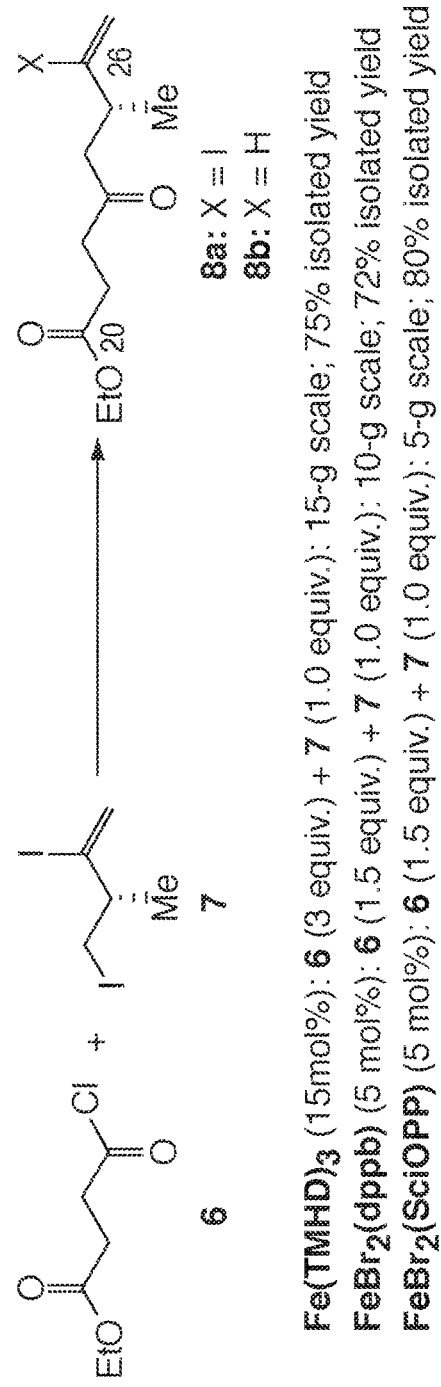
FIG. 1C shows exemplary Fe-mediated coupling reactions.

Provided herein are methods for preparing ketone-containing organic molecules. The methods are based on novel iron/copper-mediated ("Fe/Cu-medaited") coupling reactions. In certain embodiments, an advantage of the Fe/Cu-mediated couplings described herein over existing ketolization methods is that the Fe/Cu-mediated methods allow for selective coupling of alkyl halides in the presence of vinyl halides. The Fe/Cu-mediated coupling reactions can be used in the preparation of halichondrins and analogs thereof-specifically, in the preparation of intermediates en route to halichondrins and analogs thereof. The present invention also provides methods for the preparation of intermediates useful in the synthesis of halichondrins. In another aspect, the present invention provides compounds, reagents, ligands, catalysts, and kits useful in the coupling methods provided herein, as well as compounds (i.e., intermediates) useful in the preparation of halichondrins and analogs thereof.

Fe/Cu-Mediated Ketolization Reactions

Provided herein are methods for preparing ketones using a Fe/Cu-mediated coupling reaction, as outlined in Scheme 1A. As described herein, the ketolization reactions are carried out in the presence of iron and copper, e.g., in the presence of an iron complex and a copper salt. The ketolization reactions may be intermolecular or intramolecular (i.e., in Scheme 1A, $R^A$ and $R^B$ are optionally joined by a linker).

Scheme 1A

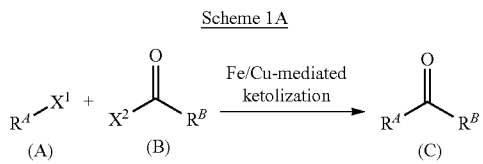

In certain embodiments, the compound of Formula (A) is a primary or secondary alkyl halide ($X^1$=halogen), and the compound of Formula (B) is an alkyl thioester or acid halide ($R^B$ is optionally substituted alkyl; and $X^2$ is halogen or —$SR^S$), as shown in Scheme 1B.

Scheme 1B

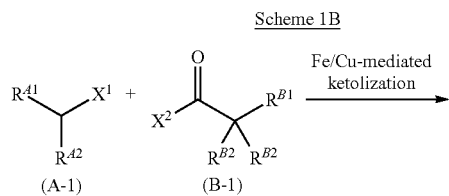

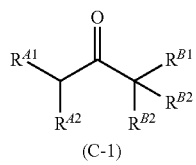

As shown in Scheme 1A, provided herein are methods for preparing a compound of Formula (C):

or a salt thereof, the methods comprising reacting a compound of Formula (A):

or a salt thereof, with a compound of Formula (B):

or a salt thereof, in the presence of iron and copper; wherein:

$X^1$ is halogen or a leaving group;

$X^2$ is halogen, a leaving group, or —$SR^S$;

$R^S$ is optionally substituted alkyl, optionally substituted carbocyclyl, optionally substituted aryl, optionally substituted heterocyclyl, or optionally substituted heteroaryl;

$R^A$ is optionally substituted alkyl; and $R^B$ is optionally substituted alkyl, optionally substituted alkenyl, optionally substituted alkynyl, optionally substituted aryl, optionally substituted carbocyclyl, optionally substituted heteroaryl, or optionally substituted heterocyclyl;

optionally, wherein $R^A$ and $R^B$ are joined together via a linker, wherein the linker is selected from the group consisting of optionally substituted alkylene, optionally substituted heteroalkylene, optionally substituted alkenylene, optionally substituted heteroalkenylene, optionally substituted alkynylene, optionally substituted heteroalkynylene, optionally substituted arylene, optionally substituted heteroarylene, optionally substituted carbocyclylene, optionally substituted heterocyclylene, optionally substituted acylene, and combinations thereof.

In certain embodiments, $R^A$ is part of a complex molecule, such as a natural product, pharmaceutical agent, fragment thereof, or intermediate thereto. In certain embodiments, $R^B$ is part of a complex molecule, such as a natural product, pharmaceutical agent, fragment thereof, or intermediate thereto.

As generally defined herein, in certain embodiments, a "linker" is a group comprising optionally substituted alkylene, optionally substituted heteroalkylene, optionally substituted alkenylene, optionally substituted heteroalkenylene, optionally substituted alkynylene, optionally substituted heteroalkynylene, optionally substituted arylene, optionally substituted heteroarylene, optionally substituted carbocyclylene, optionally substituted heterocyclylene, optionally substituted acylene, or any combination thereof. In certain embodiments, "linker" is an optionally substituted hydrocarbon chain.

In certain embodiments, the compound of Formula (A) is of Formula (A-1):

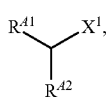

(A-1)

or a salt thereof; the compound of Formula (B) is of Formula (B-1):

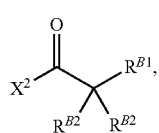

(B-1)

or a salt thereof; and the compound of Formula (C) is of Formula (C-1):

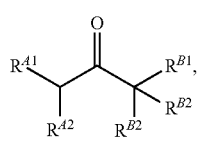

(C-1)

or a salt thereof, wherein:
  $X^1$ is halogen or a leaving group;
  $X^2$ is halogen, a leaving group, or —$SR^S$;
  $R^S$ is optionally substituted alkyl, optionally substituted carbocyclyl, optionally substituted aryl, optionally substituted heterocyclyl, or optionally substituted heteroaryl; and
  each instance of $R^{A1}$, $R^{A2}$, $R^{B1}$, and $R^{B2}$ is independently hydrogen, optionally substituted alkyl, optionally substituted alkenyl, optionally substituted alkynyl, optionally substituted aryl, optionally substituted carbocyclyl, optionally substituted heteroaryl, or optionally substituted heterocyclyl; optionally wherein $R^{A1}$ and $R^{B1}$ are joined together via a linker.

As defined herein, $R^{A1}$ is hydrogen, optionally substituted alkyl, optionally substituted alkenyl, optionally substituted alkynyl, optionally substituted aryl, optionally substituted carbocyclyl, optionally substituted heteroaryl, or optionally substituted heterocyclyl. In certain embodiments, $R^{A1}$ is hydrogen. In certain embodiments, $R^{A1}$ is optionally substituted alkyl. In certain embodiments, $R^{A1}$ is optionally substituted alkenyl. In certain embodiments, $R^{A1}$ is optionally substituted alkynyl. In certain embodiments, $R^{A1}$ is optionally substituted aryl. In certain embodiments, $R^{A1}$ is optionally substituted carbocyclyl. In certain embodiments, $R^{A1}$ is optionally substituted heteroaryl. In certain embodiments, $R^{A1}$ is optionally substituted heterocyclyl.

As defined herein, $R^{A2}$ is hydrogen, optionally substituted alkyl, optionally substituted alkenyl, optionally substituted alkynyl, optionally substituted aryl, optionally substituted carbocyclyl, optionally substituted heteroaryl, or optionally substituted heterocyclyl. In certain embodiments, $R^{A2}$ is hydrogen. In certain embodiments, $R^{A2}$ is optionally substituted alkyl. In certain embodiments, $R^{A2}$ is optionally substituted alkenyl. In certain embodiments, $R^{A2}$ is optionally substituted alkynyl. In certain embodiments, $R^{A2}$ is optionally substituted aryl. In certain embodiments, $R^{A2}$ is optionally substituted carbocyclyl. In certain embodiments, $R^{A2}$ is optionally substituted heteroaryl. In certain embodiments, $R^{A2}$ is optionally substituted heterocyclyl.

As defined herein, $R^{B1}$ is hydrogen, optionally substituted alkyl, optionally substituted alkenyl, optionally substituted alkynyl, optionally substituted aryl, optionally substituted carbocyclyl, optionally substituted heteroaryl, or optionally substituted heterocyclyl. In certain embodiments, $R^{B1}$ is hydrogen. In certain embodiments, $R^{B1}$ is optionally substituted alkyl. In certain embodiments, $R^{B1}$ is optionally substituted alkenyl. In certain embodiments, $R^{B1}$ is optionally substituted alkynyl. In certain embodiments, $R^{B1}$ is optionally substituted aryl. In certain embodiments, $R^{B1}$ is optionally substituted carbocyclyl. In certain embodiments, $R^{B1}$ is optionally substituted heteroaryl. In certain embodiments, $R^{B1}$ is optionally substituted heterocyclyl.

As defined herein, $R^{B2}$ is hydrogen, optionally substituted alkyl, optionally substituted alkenyl, optionally substituted alkynyl, optionally substituted aryl, optionally substituted carbocyclyl, optionally substituted heteroaryl, or optionally substituted heterocyclyl. In certain embodiments, $R^{B2}$ is hydrogen. In certain embodiments, $R^{B2}$ is optionally substituted alkyl. In certain embodiments, $R^{B2}$ is optionally substituted alkenyl. In certain embodiments, $R^{B2}$ is optionally substituted alkynyl. In certain embodiments, $R^{B2}$ is optionally substituted aryl. In certain embodiments, $R^{B2}$ is optionally substituted carbocyclyl. In certain embodiments, $R^{B2}$ is optionally substituted heteroaryl. In certain embodiments, $R^{B2}$ is optionally substituted heterocyclyl.

In certain embodiments, $R^{A1}$ and/or $R^{A2}$ is part of a complex molecule, such as a natural product, pharmaceutical agent, fragment thereof, or intermediate thereto. In certain embodiments, $R^{B1}$, $R^{B2}$, and/or $R^{B3}$ is part of a complex molecule, such as a natural product, pharmaceutical agent, fragment thereof, or intermediate thereto.

The Fe/Cu-mediated ketolization reactions provided herein may be performed in an intramolecular fashion to yield cyclic ketones as shown in Scheme 1C.

Scheme 1C

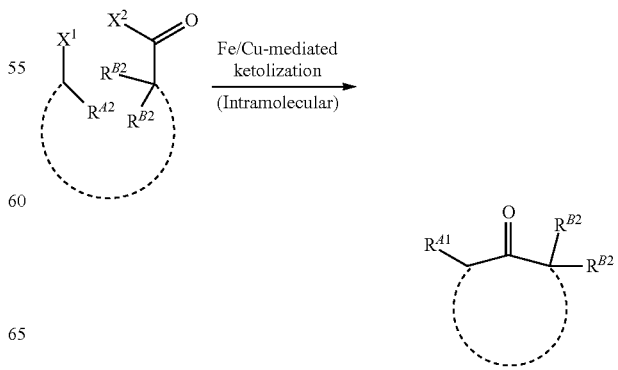

As shown in Scheme 1C, provided herein are methods for preparing a compound of Formula (C-2):

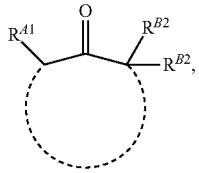
(C-2)

or salt thereof, comprising reacting a compound of Formula (A-B):

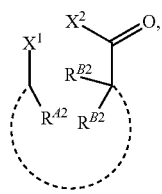
(A-B)

or a salt thereof, in the presence of iron and copper; wherein:
$X^1$ is halogen or a leaving group;
$X^2$ is halogen, a leaving group, or —$SR^S$;
$R^S$ is optionally substituted alkyl, optionally substituted carbocyclyl, optionally substituted aryl, optionally substituted heterocyclyl, or optionally substituted heteroaryl;
$R^{A2}$ and $R^{B2}$ are independently hydrogen, optionally substituted alkyl, optionally substituted alkenyl, optionally substituted alkynyl, optionally substituted aryl, optionally substituted carbocyclyl, optionally substituted heteroaryl, or optionally substituted heterocyclyl; and

represents a linker.

In certain embodiments, $X^1$ is a halogen (e.g., —I, —Br, —Cl, —F). In certain embodiments, $X^1$ is a halogen bonded to an alkyl group (i.e., an "alkyl halide"). In certain embodiments, the Fe/Cu-mediated ketolization reaction is selective for an alkyl halide over a vinyl halide. For example, when a reaction mixture or a compound comprises both an alkyl halide and a vinyl halide, the alkyl halide reacts at a faster rate than the vinyl halide. In certain embodiments, the Fe/Cu-mediated reactions described herein are selective for alkyl iodides over vinyl halides (e.g., vinyl iodides). In certain embodiments, the selectivity is greater than 2:1, 3:1, 4:1, 5:1, 10:1, 15:1, 20:1, 25:1, 30:1, 40:1, 50:1, 60:1, 70:1, 80:1, 90:1, 100:1, or 100:1.

In certain embodiments, $X^2$ is a halogen (e.g., —I, —Br, —Cl, —F). In certain embodiments, $X^2$ is —Cl. In other embodiments, $X^2$ is —$SR^S$, wherein $R^S$ is as defined herein. In certain embodiments, $X^2$ is —S-heteroaryl. In certain embodiments, $X^2$ is —S-pyridyl. In certain embodiments, $X^2$ is —S-2-pyridyl:

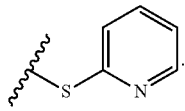

Fe/Cu-mediated ketolization reactions provided herein are carried out in the presence of iron. The iron source may be an iron complex, iron salt, iron catalyst, or pre-catalyst. In certain embodiments, the iron source is iron (II). In certain embodiments, the iron source is iron (III).

In certain embodiments, an iron complex is of the formula Fe(ligand)$_3$. In certain embodiments, "ligand" is TMHD, DBM, or acac. In certain embodiments, the iron complex is of the formula:

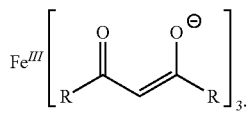

In certain embodiments, the iron complex is Fe(TMHD)$_3$, which is of the formula:

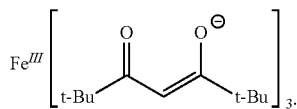

In certain embodiments, the iron complex is Fe(DBM)$_3$, which is of the formula:

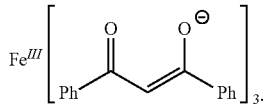

In certain embodiments, the iron complex is Fe(acac)$_3$, which is of the formula:

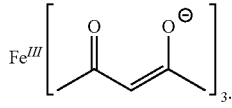

In certain embodiments, the iron complex comprises two phosphine ligands. In certain embodiments, the iron complex comprises a bisphosphine ligand. In certain embodiments, the iron complex is of the formula Fe(X)$_2$(ligand), wherein each instance of X is independently halogen (e.g., Cl, Br, I, or F), and "ligand" is a bisphosphine ligand. In certain embodiments, the bisphosphine ligand is dppb or SciOPP. In certain embodiments, the iron complex is of the formula:

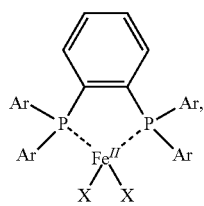

wherein each instance of Ar is independently optionally substituted aryl, and each instance of X is independently halogen (e.g., Cl, Br, I, or F). In certain embodiments, the iron complex is Fe(X)$_2$(dppb) (each instance of Ar is phenyl (Ph). In certain embodiments, the iron complex is Fe(Br)$_2$(dppb), which is of the formula:

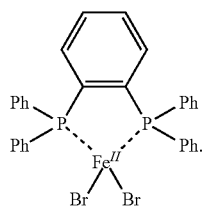

In certain embodiments, the iron complex is Fe(C$_1$)$_2$(dppb), which is of the formula:

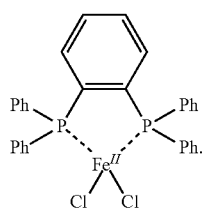

In certain embodiments, the iron complex is Fe(X)$_2$(Sci-OPP) (each instance of Ar is of the formula:

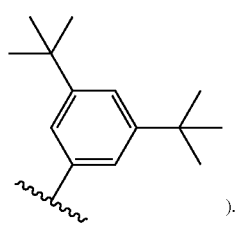 [SMILES: *c1cc(C(C)(C)C)cc(C(C)(C)C)c1]

).

In certain embodiments, the iron complex is Fe(Br)$_2$(Sci-OPP), which is of the formula:

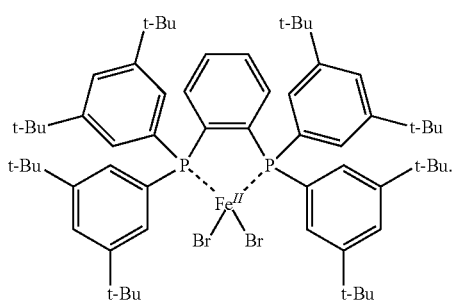

In certain embodiments, the iron complex is Fe(C$_1$)$_2$(Sci-OPP), which is of the formula:

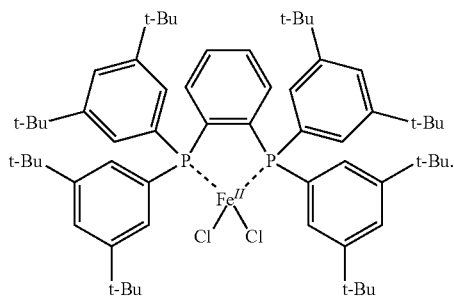

In certain embodiments, the iron complex is of the formula:

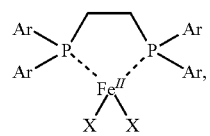

wherein each instance of Ar is independently optionally substituted aryl; and each instance of X is independently halogen (e.g., Cl, Br, I, or F). In certain embodiments, the iron complex is of the formula FeX$_2$(dppe), wherein each instance of X is independently halogen (e.g., Cl, Br, I, or F). In certain embodiments, the iron complex is FeBr$_2$(dppe), which is of the formula:

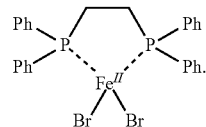

In certain embodiments, the iron complex is FeCl$_2$(dppe).
In certain embodiments, the iron complex is of the formula:

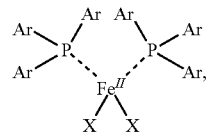

wherein each instance of Ar is independently optionally substituted aryl, and each instance of X is independently halogen (e.g., Cl, Br, I, or F). In certain embodiments, the iron complex is of the formula: FeX$_2$(PPh$_3$)$_2$, wherein each instance of X is independently halogen (e.g., Cl, Br, I, or F). In certain embodiments, the iron complex is of the formula: FeBr$_2$(PPh$_3$)$_2$ or FeCl$_2$(PPh$_3$)$_2$.

In certain embodiments, the iron is present in a catalytic amount. In certain embodiments, the iron is present at approximately 1-5 mol %, 5-10 mol %, 1-10 mol %, 5-20 mol %, 10-20 mol %, 20-30 mol %, 20-40 mol %, 30-40 mol %, 40-50 mol %, 50-60 mol %, 60-70 mol %, 70-80 mol %, or 80-90 mol % relative to a compound of Formula (A) or (B) in the reaction mixture. In certain embodiments, the iron is present in from 1-50 mol %. In certain embodiments, the iron is present in from 1-10 mol %. In certain embodiments, the iron is present in from 1-20 mol %. In certain embodiments, the iron is present in approximately 5 mol %. In certain embodiments, the iron is present in approximately 10 mol %. In certain embodiments, the iron is present in approximately 15 mol %. In certain embodiments, the iron is present in a stoichiometric or excess amount relative to a compound of Formula (A) or (B) in the reaction mixture.

Fe/Cu-mediated ketolization reactions provided herein are carried out in the presence of copper. The copper source may be a copper complex, copper salt, copper catalyst, or pre-catalyst. In certain embodiments, the copper source is copper(I). In certain embodiments, the copper source is copper(II). In certain embodiments, the copper source is a copper salt. In certain embodiments, the copper salt is selected from CuCl, CuBr, CuI, CuCN, CuTc, $CuBr_2$, and $CuCl_2$. In certain embodiments, the copper salt is $CuCl_2$. In certain embodiments, the copper salt is CuI.

In certain embodiments, the copper is present in a stoichiometric or excess amount relative to a compound of Formula (A) or (B) in the reaction mixture. In certain embodiments, approximately 1 equivalent of copper is present (i.e., stoichiometric). In other embodiments, greater than 1 equivalent of copper is present (i.e., excess). In certain embodiments, approximately 1.1, 1.2, 1.3, 1.4, 1.5, 1.6, 1.7, 1.8, 1.9, 2.0, 2.5, 3.0, 3.5, 4.0, 4.5, 5.0, 6.0, 7.0, 8.0, 9.0, or 10.0 equivalents of copper are present. In certain embodiments, the copper is present in a catalytic amount. In certain embodiments, the copper is present at approximately 1-5 mol %, 5-10 mol %, 1-10 mol %, 5-20 mol %, 10-20 mol %, 20-30 mol %, 20-40 mol %, 30-40 mol %, 40-50 mol %, 50-60 mol %, 60-70 mol %, 70-80 mol %, or 80-90 mol % relative to a compound of Formula (A) or (B) in the reaction mixture.

The Fe/Cu-mediated ketolization reactions may be carried out in the presence of one or more additional reagents or catalysts. In certain embodiments, the reaction is carried out in the presence of zirconium. In certain embodiments, the reaction is carried out in the presence of a zirconium complex. In certain embodiments, the zirconium complex is of the formula: (ligand)$_n$$ZrX_2$; wherein n is the number of ligands (e.g., 0, 1, 2, 3, 4), and X is halogen (e.g., Cl, Br, I, or F). In certain embodiments, n is 2, and the ligand is cyclopentadienyl. In certain embodiments, the zirconium source is $Cp_2ZrX_2$. In certain embodiments, the zirconium source is $Cp_2ZrCl_2$.

In certain embodiments, the zirconium is present in a catalytic amount. In certain embodiments, the zirconium is present in between 1-5 mol %, 5-10 mol %, 1-10 mol %, 5-20 mol %, 10-20 mol %, 20-30 mol %, 30-40 mol %, 40-50 mol %, 50-60 mol %, 60-70 mol %, 70-80 mol %, or 80-90 mol % relative to a compound of Formula (A) or (B) in the reaction mixture. In certain embodiments, the zirconium is present in a stoichiometric or excess amount relative to a compound of Formula (A) or (B) in the reaction mixture. In other embodiments, greater than 1 equivalent of zirconium is present (i.e., excess). In certain embodiments, approximately 1.1, 1.2, 1.3, 1.4, 1.5, 1.6, 1.7, 1.8, 1.9, 2, 2.5, 3, 3.5, 4, 4.5, 5, 6, 7, 8, 9, or 10 equivalents of zirconium are present. In certain embodiments, approximately 1 equivalent of zirconium is present (i.e., stoichiometric). In certain embodiments, a zirconium complex is employed in the reaction when a thioester is used as a coupling partner (e.g., when $X^2$ is —SR$^S$).

In certain embodiments, the reaction is carried out in the presence of a lithium salt. In certain embodiments, the lithium salt is LiCl, LiBr, or LiI. In certain embodiments, the lithium salt is LiCl. In certain embodiments, the lithium salt is present in catalytic amount. In certain embodiments, the lithium salt is present in a stoichiometric or excess amount relative to a compound of Formula (A) or (B) in the reaction mixture. In certain embodiments, approximately 1 equivalent of lithium salt is present (i.e., stoichiometric). In other embodiments, greater than 1 equivalent of lithium salt is present (i.e., excess). In certain embodiments, approximately 1.1, 1.2, 1.3, 1.4, 1.5, 1.6, 1.7, 1.8, 1.9, 2, 2.5, 3, 3.5, 4, 4.5, 5, 6, 7, 8, 9, or 10 equivalents of lithium salt are present. In certain embodiments, approximately 3 equivalents of lithium salt is present.

In certain embodiments, the reaction is carried out in the presence of a reducing metal. In certain embodiments, the reducing metal is zinc or manganese (e.g., zinc (0) or manganese (0)).

In certain embodiments, the zinc source is zinc powder, zinc foil, zinc beads, or any other form of zinc metal. The zinc may be present in a catalytic, stoichiometric, or excess amount. In certain embodiments, the zinc is present in excess (i.e., greater than 1 equivalent) relative to a compound of Formula (A) or Formula (B). In certain embodiments, between 1 and 10 equivalents of zinc are used. In certain embodiments, approximately 1.5, 2, 2.5, 3, 3.5, 4, 4.5, 5, 5.5, 6, 7, 8, 9, or 10 equivalents of zinc are present. In certain embodiments, approximately 2 equivalents of zinc are used.

In certain embodiments, the manganese source is manganese powder, manganese foil, manganese beads, or any other form of manganese metal. The manganese may be present in a catalytic, stoichiometric, or excess amount. In certain embodiments, the manganese is present in excess (i.e., greater than 1 equivalent) relative to a compound of Formula (A) or Formula (B). In certain embodiments, between 1 and 10 equivalents of manganese are used. In certain embodiments, approximately 1.5, 2, 2.5, 3, 3.5, 4, 4.5, 5, 5.5, 6, 7, 8, 9, or 10 equivalents of manganese are present. In certain embodiments, approximately 2 equivalents of manganese are used.

In certain embodiments, the Fe/Cu-mediated ketolization described herein is carried out in a solvent. Any solvent may be used, and the scope of the method is not limited to any particular solvent or mixture of solvents. The solvent may be polar or non-polar, protic or aprotic, or a combination of solvents (e.g., co-solvents). Examples of useful organic solvents are provided herein. In certain embodiments, the ketolization is carried out in a polar solvent, such as an ethereal solvent. In certain embodiments, the ketolization reaction is carried out in dimethoxyethane (DME).

The Fe/Cu-mediated ketolization reactions described herein may be carried out at any concentration in solvent. Concentration refers to the molar concentration (mol/L) of a coupling partners (e.g., compounds of Formula (A) or (B)) in a solvent. In certain embodiments, the concentration is approximately 0.5 M. In certain embodiments, the concentration is approximately 0.1, 0.2, 0.3, 0.4, 0.5, 0.6, 0.7, 0.8, or 0.9 M. In certain embodiments, the concentration is greater than 1 M. In certain embodiments, the concentration is less than 0.1 M.

The Fe/Cu-mediated ketolization reactions described herein can be carried out at any temperature. In certain embodiments, the reaction is carried out at around room temperature (i.e., between 18 and 24° C.). In certain embodiments, the reaction is carried out below room temperature (e.g., between 0° C. and room temperature). In certain embodiments, the reaction is carried out at above room temperature (e.g., between room temperature and 100° C.). In certain embodiments, the reaction is carried out at approximately 0° C.

A reaction described herein may be carried out over any amount of time. In certain embodiments, a reaction is allowed to run for seconds, minutes, hours, or days.

In certain embodiments, the Fe/Cu-mediated ketolization is carried out in the presence of an iron complex, a copper salt, a lithium salt, and a reducing metal. In certain embodiments, the ketolization is carried out in the presence of Fe(TMHD)$_3$, CuCl$_2$, LiCl, and Mn. In certain embodiments, the ketolization is carried out in the presence of FeBr$_2$(dppb), CuCl$_2$, LiCl, and Mn metal. In certain embodiments, the reaction is carried out in a polar solvent. In certain embodiments, the polar solvent is an ethereal solvent, such as DME. In certain embodiments, the reaction is carried out at or below room temperature. In certain embodiments, the reaction is carried out at a temperature around 0° C.

For example, in certain embodiments, the coupling may be carried out under the following conditions: Fe(TMHD)$_3$ (10 mol %), CuCl$_2$ (1.0 equiv.), Mn (2 equiv.), LiCl (3 equiv.), DME, 0° C., for 10-20 hours. As another example, in certain embodiments, the coupling may be carried out under the following conditions: FeBr$_2$(dppb) (5 mol %), CuCl$_2$ (1.0 equiv.), LiCl (3 equiv.), Mn (2 equiv.), DME, 0° C., for 10-20 hours.

In certain embodiments, the Fe/Cu-mediated ketolization is carried out in the presence of an iron complex, a copper salt, a zirconium complex, a lithium salt, and a reducing metal. In certain embodiments, the ketolization is carried out in the presence of FeBr$_2$(dppb), CuI, ZrCp$_2$Cl$_2$, LiCl, and Mn metal. In certain embodiments, the reaction is carried out in a polar solvent. In certain embodiments, the polar solvent is an ethereal solvent, such as DME. In certain embodiments, the reaction is carried out at or below room temperature. In certain embodiments, the reaction is carried out at a temperature around 0° C.

For example, in certain embodiments, the coupling may be carried out under the following conditions: FeBr$_2$(dppb) (5 mol %), CuI (1.0 equiv.), ZrCp$_2$Cl$_2$ (1.0 equiv), LiCl (3 equiv.), Mn (2 equiv.), DME, 0° C., for 10-20 hours.

Synthesis of Halichondrins and Intermediates

The Fe/Cu-mediated ketolization reactions provided herein can be applied to the synthesis of complex molecules, such intermediates en route to halichondrins and analogs thereof. For example, Scheme 2 shows that a compound of Formula (I-13) can be prepared via Fe/Cu-mediated coupling of a compound of Formula (I-12) with a compound of Formula (I-10). In Scheme 2, compounds of Formula (I-13) are useful intermediates in the synthesis of halichondrins (e.g., halichondrin A, B, C), and analogs thereof.

Scheme 2

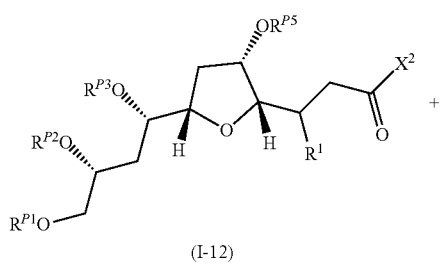
(I-12)

+

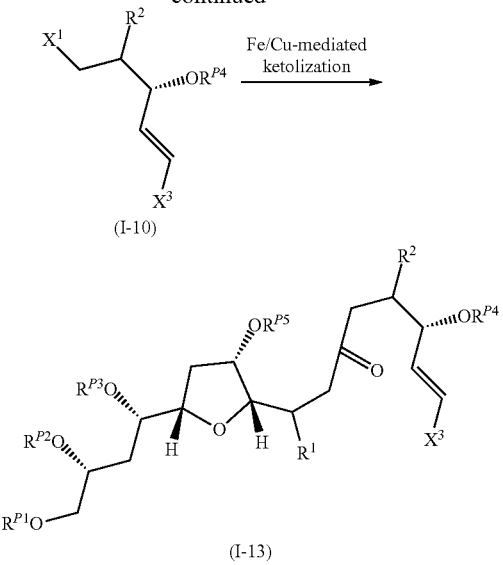
(I-10)

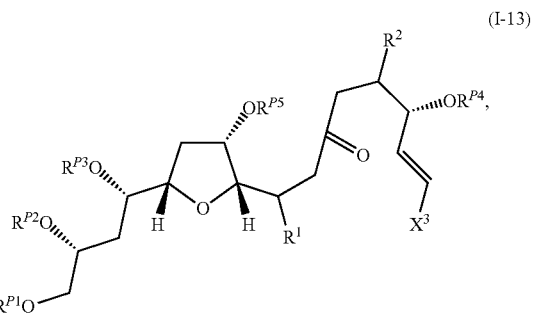
(I-13)

As shown in Scheme 2, provided herein is a method of preparing a compound of Formula (I-13):

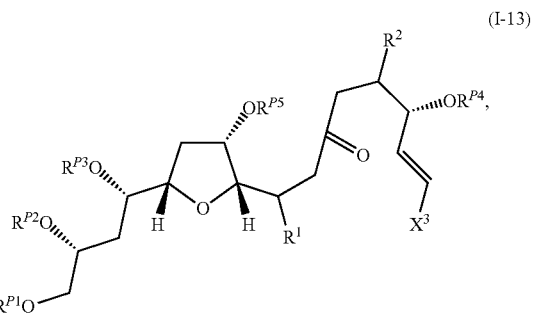
(I-13)

or a salt thereof, the method comprising coupling a compound of Formula (I-12):

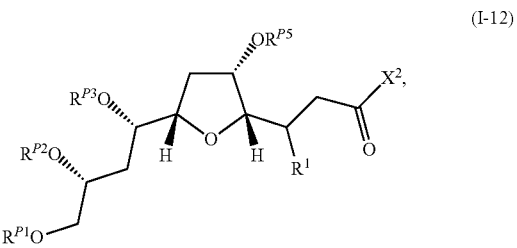
(I-12)

or a salt thereof, with a compound of Formula (I-10):

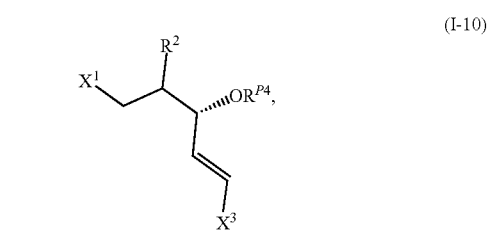
(I-10)

or a salt thereof, wherein:
X$^1$ and X$^3$ are each independently a halogen or a leaving group;

X is halogen, a leaving group, or —SR$^S$;

R$^1$ and R$^2$ are each independently hydrogen, halogen, or optionally substituted alkyl; and R$^{P1}$, R$^{P2}$, R$^{P3}$, R$^{P4}$, and R$^{P5}$ are each independently hydrogen, optionally substituted alkyl, optionally substituted acyl, or an oxygen protecting group.

In certain embodiments, the compound of Formula (I-12) is a compound of Formula (I-12-S):

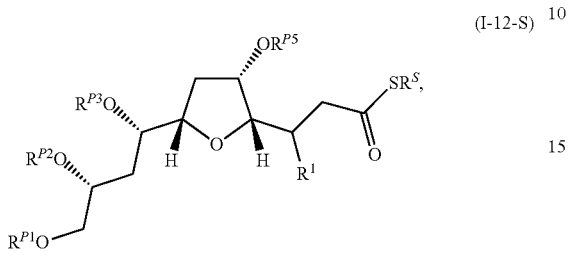

(I-12-S)

or a salt thereof, wherein:

R$^S$ is optionally substituted alkyl, optionally substituted carbocyclyl, optionally substituted aryl, optionally substituted heterocyclyl, or optionally substituted heteroaryl.

In certain embodiments, the step of coupling a compound of Formula (I-12), or a salt thereof, with a compound of Formula (I-10), or a salt thereof, involves a Fe/Cu-mediated ketolization reaction as described herein (e.g., carried out in the presence of iron and copper).

Any reagents or conditions described for the Fe/Cu-mediated ketolizations described herein can be used in the coupling step.

As described herein, the Fe/Cu-mediated ketolizations are selective for alkyl halides in the presence of vinyl halides. Therefore, in certain embodiments, when X$^1$ and X$^3$ are both halogen, the reaction occurs selectively at X$^1$ rather than X$^3$, yielding a compound of Formula (I-13) as the major product. In certain embodiments, when X$^1$ is —I, and X$^3$ is halogen, the reaction occurs selectively at X$^1$ rather than X$^3$, yielding a compound of Formula (I-13) as the major product. In certain embodiments, the selectivity is greater than 2:1, 3:1, 4:1, 5:1, 10:1, 15:1, 20:1, 25:1, 30:1, 40:1, 50:1, 60:1, 70:1, 80:1, 90:1, 100:1, or 100:1.

In certain embodiments, R$^{P1}$, R$^{P2}$, R$^{P3}$, R$^{P4}$, and R$^{v5}$ are each optionally substituted silyl protecting groups. In certain embodiments, R$^{P1}$, R$^{P2}$, R$^{P3}$, R$^{P4}$, and R$^{v5}$ are each trialkylsilyl protecting groups. In certain embodiments, R$^{P1}$ and R$^{P4}$ are TBS protecting groups, and R$^{P2}$, R$^{P3}$, and R$^{v5}$ are TES protecting groups.

In certain embodiments, the coupling to form a compound of Formula (I-13), or a salt thereof, is carried out in the presence of an iron complex, a copper salt, a lithium salt, a zirconium complex, and a reducing metal. In certain embodiments, the coupling is carried out in the presence of FeBr$_2$(SciOPP), CuI, ZrCp$_2$Cl$_2$, LiCl, and Mn metal. In certain embodiments, the reaction is carried out in a polar solvent. In certain embodiments, the polar solvent is an ethereal solvent, such as DME. In certain embodiments, the reaction is carried out at or below room temperature. In certain embodiments, the reaction is carried out at a temperature around 0° C.

For example, in certain embodiments, the coupling may be carried out under the following conditions: FeBr$_2$(SciOPP) (5 mol %), CuI (1.0 equiv.), ZrCp$_2$Cl$_2$ (1.0 equiv.), LiCl (3 equiv.), and Mn (2.0 equiv), DME, 0° C., 10-20 hours.

Ketolization reactions provided herein can be applied to the preparation of other intermediates useful in the synthesis of halichondrins and analogs thereof. For example, as shown in Scheme 3, a compound of Formula (I-11) can be prepared via Fe/Cu-mediated coupling of a compound of Formula (I-9) with a compound of Formula (I-10). Compounds of Formula (I-11) are useful intermediates in the synthesis of halichondrins and analogs thereof.

Scheme 3

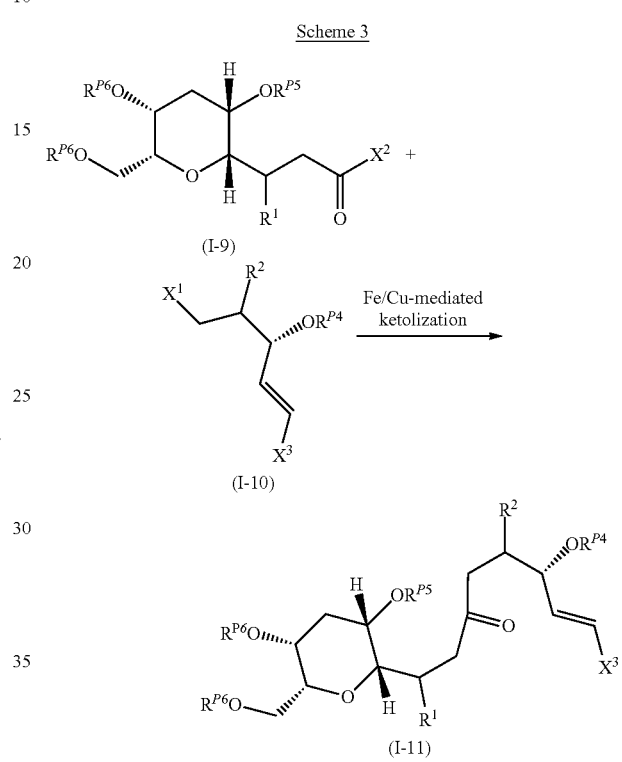

As shown in Scheme 3, provided herein is a method of preparing a compound of Formula (I-11):

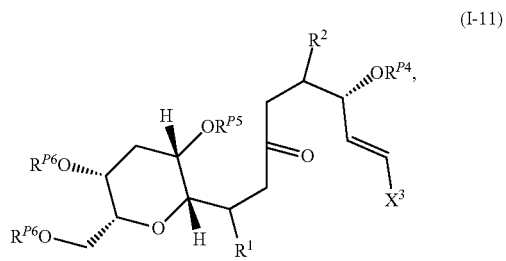

(I-11)

or a salt thereof, the method comprising coupling a compound of Formula (I-9):

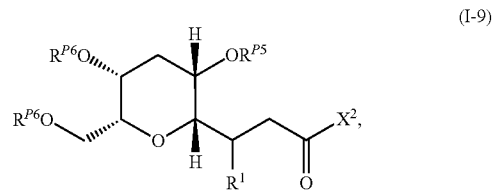

(I-9)

or a salt thereof, with a compound of Formula (I-10):

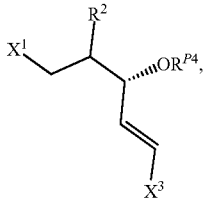
(I-10)

or a salt thereof, wherein:
X$^1$ and X$^3$ are each independently a halogen or a leaving group;
X$^2$ is halogen, a leaving group, or —SR$^S$;
R$^1$ and R$^2$ are each independently hydrogen, halogen, or optionally substituted alkyl; and
R$^{P4}$, R$^{P5}$, and R$^{P6}$ are independently hydrogen, optionally substituted alkyl, optionally substituted acyl, or an oxygen protecting group; optionally wherein two R$^{P6}$ are joined with the intervening atoms to form optionally substituted heterocyclyl.

In certain embodiments, a compound of Formula (I-9) is of Formula (I-9-S): or a salt thereof, wherein:

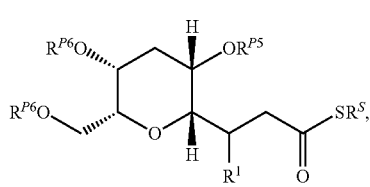
(I-9-S)

or a salt thereof, wherein:
R$^S$ is optionally substituted alkyl, optionally substituted carbocyclyl, optionally substituted aryl, optionally substituted heterocyclyl, or optionally substituted heteroaryl.

In certain embodiments, the step of coupling a compound of Formula (I-9), or a salt thereof, with a compound of Formula (I-10), or a salt thereof, is a Fe/Cu-mediated ketolization described herein (e.g., carried out in the presence of iron and copper). Any reagents or conditions described for the Fe/Cu-mediated ketolizations described herein can be used in the coupling step.

As described herein, the Fe/Cu-mediated ketolizations are selective for alkyl halides over vinyl halides. Therefore, in certain embodiments, when X$^1$ and X$^3$ are both halogen, the reaction occurs selectively at X$^1$ rather than X$^3$, yielding a compound of Formula (I-11) as the major product. In certain embodiments, when X$^1$ is —I, and X$^3$ is halogen, the reaction occurs selectively at X$^1$ rather than X$^3$, yielding a compound of Formula (I-11) as the major product. In certain embodiments, the selectivity is greater than 2:1, 3:1, 4:1, 5:1, 10:1, 15:1, 20:1, 25:1, 30:1, 40:1, 50:1, 60:1, 70:1, 80:1, 90:1, 100:1, or 100:1.

In certain embodiments, R$^{P4}$, R$^{P5}$, and R$^{P6}$ are each silyl protecting groups. In certain embodiments, R$^{P4}$ and R$^{P5}$ are trialkylsilyl protecting groups, and the two R$^{P6}$ groups are joined together to form:

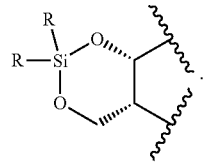

In certain embodiments, R$^{P4}$ is a TBS protecting group, R$^{P5}$ is a TES protecting group, and the two R$^{P6}$ groups are joined together to form:

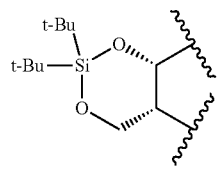

In certain embodiments, the coupling to yield a compound of Formula (I-11) is carried out in the presence of an iron complex, a copper salt, a lithium salt, a zirconium complex, and a reducing metal. In certain embodiments, the coupling is carried out in the presence of FeBr$_2$(SciOPP), CuI, ZrCp$_2$Cl$_2$, LiCl, and Mn metal. In certain embodiments, the reaction is carried out in a polar solvent. In certain embodiments, the polar solvent is an ethereal solvent such as DME. In certain embodiments, the reaction is carried out at or below room temperature. In certain embodiments, the reaction is carried out at a temperature around 0° C.

For example, in certain embodiments, the coupling may be carried out under the following conditions: FeBr$_2$(SciOPP) (5 mol %), CuI (1.0 equiv.), ZrCp$_2$Cl$_2$ (1.0 equiv.), LiCl (3 equiv.), and Mn (2.0 equiv), DME, 0° C., 10-20 hours.

Methods described herein can be used to prepare compounds in any chemical yield. In certain embodiments, a compound is produced in from 1-10%, 10-20% 20-30%, 30-40%, 40-50%, 50-60%, 60-70%, 70-80%, 80-90%, or 90-100% yield. In certain embodiments, the desired product is obtained in greater than 10%, 20%, 30%, 40%, 50%, 60%, 70%, 80%, or 90% yield. In certain embodiments, it is greater than 50% yield. In certain embodiments, it is greater than 70% yield. In certain embodiments, the yield is the percent yield after one synthetic step. In certain embodiments, the yield is the percent yield after more than one synthetic step (e.g., 2, 3, 4, or 5 synthetic steps).

As described herein, the Fe/Cu-mediated ketolizations are selective for alkyl halides over vinyl halides. Therefore, in certain embodiments, when X$^1$ and X$^3$ are both halogen, the reaction occurs selectively at X$^1$ rather than X$^3$. In certain embodiments, the selectivity is approximately 2:1, 3:1, 4:1, 5:1, 10:1, 15:1, 20:1, 25:1, 30:1, 40:1, 50:1, 60:1, 70:1, 80:1, 90:1, 100:1, or greater than 100:1. In certain embodiments, the selectivity is greater than 2:1, 3:1, 4:1, 5:1, 10:1, 15:1, 20:1, 25:1, 30:1, 40:1, 50:1, 60:1, 70:1, 80:1, 90:1, 100:1, or 100:1.

Methods described herein may further comprise one or more purification steps. For example, in certain embodiments, a compound produced by a method described herein may be purified by chromatography, extraction, filtration, precipitation, crystallization, or any other method known in the art. In certain embodiments, a compound or mixture is carried forward to the next synthetic step without purification (i.e., crude).

Scheme 4 shows that a compound of Formula (II-3) can be prepared via Fe/Cu-mediated coupling of a compound of Formula (II-1) with a compound of Formula (II-2). In Scheme 4, compounds of Formula (II-3) are useful intermediates in the synthesis of compounds in the halichondrin series (e.g., halichondrin A, B, C), and analogs thereof. In particular, compounds of Formula (II-3) are useful as the C20-C26 fragments (i.e., building blocks) of halichondrins.

Scheme 4

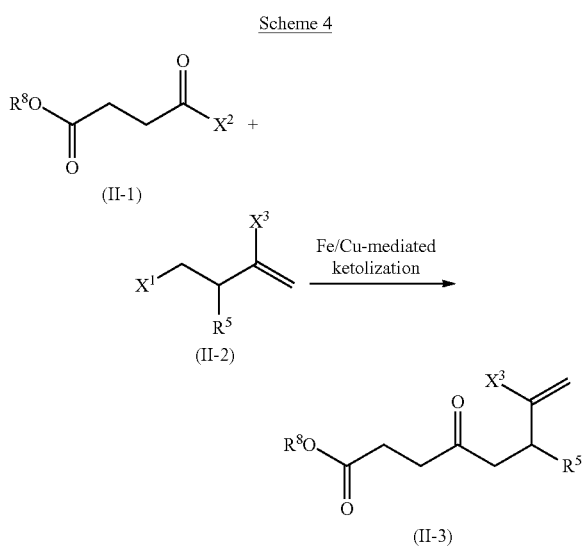

As shown in Scheme 4, provided herein is a method of preparing a compound of Formula (II-3):

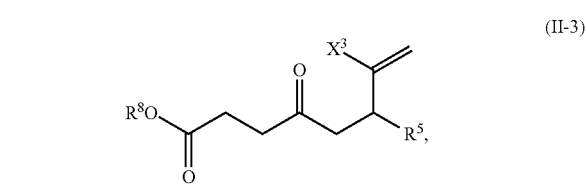

or a salt thereof, the method comprising coupling a compound of Formula (II-1):

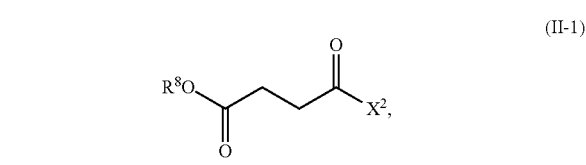

or a salt thereof, with a compound of Formula (II-2):

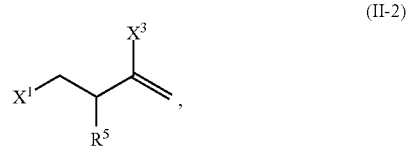

or a salt thereof, wherein:
  $X^1$ and $X^3$ are each independently a halogen or a leaving group;
  $X^2$ is halogen, a leaving group, or —$SR^S$;
  $R^5$ is hydrogen, halogen, or optionally substituted alkyl; and $R^8$ is alkyl, optionally substituted carbocyclyl, optionally substituted aryl, optionally substituted heterocyclyl, optionally substituted heteroaryl, optionally substituted acyl, or an oxygen protecting group.

In certain embodiments, the compound of Formula (II-1) is a compound of Formula (II-1-Cl):

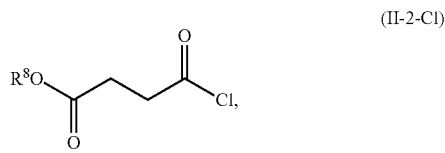

or a salt thereof.

In certain embodiments, the compound of Formula (II-1) is the following:

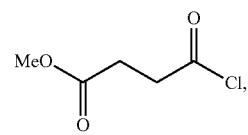

or a salt thereof.

In certain embodiments, the compound of Formula (II-1) is the following:

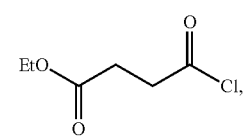

or a salt thereof.

In certain embodiments, the compound of Formula (II-2) is a compound of Formula (II-1-I):

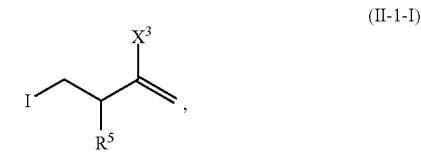

or a salt thereof.

In certain embodiments, the compound of Formula (II-2) is the following:

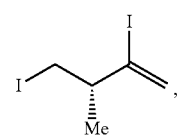

or a salt thereof.

In certain embodiments, the compound of Formula (II-3) is the following:

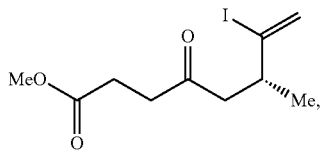

or a salt thereof.

In certain embodiments, the compound of Formula (II-3) is the following:

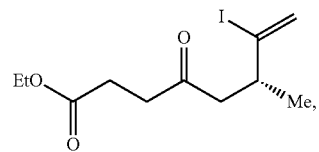

or a salt thereof

In certain embodiments, the step of coupling a compound of Formula (II-1), or a salt thereof, with a compound of Formula (II-2), or a salt thereof, involves a Fe/Cu-mediated ketolization reaction as described herein (e.g., carried out in the presence of iron and copper).

Any reagents or conditions described for the Fe/Cu-mediated ketolizations described herein can be used in the coupling step.

As described herein, the Fe/Cu-mediated ketolizations are selective for alkyl halides in the presence of vinyl halides. Therefore, in certain embodiments, when $X^1$ and $X^3$ are both halogen, the reaction occurs selectively at $X^1$ rather than $X^3$, yielding a compound of Formula (II-3) as the major product. In certain embodiments, when $X^1$ is —I, and $X^3$ is halogen, the reaction occurs selectively at $X^1$ rather than $X^3$, yielding a compound of Formula (II-3) as the major product. In certain embodiments, the selectivity is greater than 2:1, 3:1, 4:1, 5:1, 10:1, 15:1, 20:1, 25:1, 30:1, 40:1, 50:1, 60:1, 70:1, 80:1, 90:1, 100:1, or 100:1. In certain embodiments, $X^1$ is —I; $X^3$ is —I; and $X^2$ is —Cl.

In certain embodiments, $R^8$ is ethyl; and $R^5$ is methyl. In certain embodiments, $R^8$ is methyl; and $R^5$ is methyl.

In certain embodiments, the Fe/Cu-mediated ketolization is carried out in the presence of an iron complex, a copper salt, a lithium salt, and a reducing metal. In certain embodiments, the ketolization is carried out in the presence of Fe(TMHD)$_3$, CuCl$_2$, LiCl, and Mn. In certain embodiments, the ketolization is carried out in the presence of FeBr$_2$(dppb), CuCl$_2$, LiCl, and Mn metal. In certain embodiments, the reaction is carried out in a polar solvent. In certain embodiments, the polar solvent is an ethereal solvent, such as DME. In certain embodiments, the reaction is carried out at or below room temperature. In certain embodiments, the reaction is carried out at a temperature around 0° C.

For example, in certain embodiments, the coupling may be carried out under the following conditions: FeBr$_2$(dppb) (5 mol %), CuCl$_2$ (20 mol %), LiCl (3 equiv.), Mn (2 equiv.), DME, approximately 0° C. (e.g., about 0-5° C.), for 10-30 hours.

In certain embodiments, the method further comprises a step of reacting the compound of Formula (II-3):

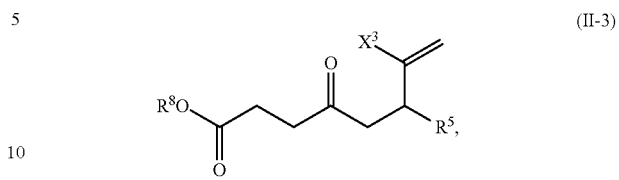

or a salt thereof, in the presence of a reagent of Formula R$^{P9}$OH, to yield a compound of Formula (III-1):

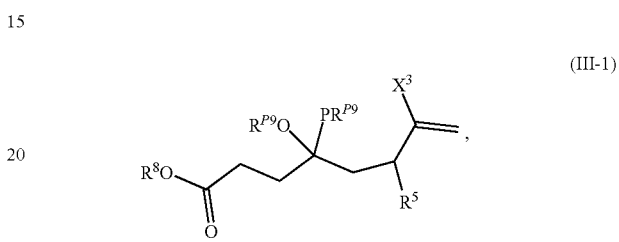

or a salt thereof; wherein:

$X^3$ is halogen;

$R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group; and each $R^{P9}$ is independently hydrogen, optionally substituted alkyl, optionally substituted acyl, or an oxygen protecting group; optionally wherein two $R^{P9}$ groups are joined together with the intervening atoms.

In certain embodiments, the reaction is carried out in the presence of an acid. In certain embodiments, the acid is a sulfonic acid. In certain embodiments, the acid is p-toluenesulfonic acid. In certain embodiments, the reaction is carried out in the presence of an orthoformate. In certain embodiments, the reaction is carried out in the presence of trimethyl orthoformate.

In certain embodiments, the reagent of formula R$^{P9}$OH is a diol; and two R$^{P9}$ are joined together with the intervening atoms. In these embodiments, in the compound of Formula (III-1), two R$^{P9}$ are taken together with the intervening atoms to form optionally substituted heterocyclyl. In certain embodiments, the reagent is an 1,3-diol. In certain embodiments, the reagent R$^{P9}$OH is of the formula:

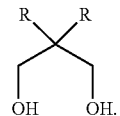

In certain embodiments, the reagent is 2,2-dimethyl-1,3-propanediol, having the structure:

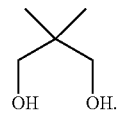

In certain embodiments, the compound of Formula (II-3) is of the formula:

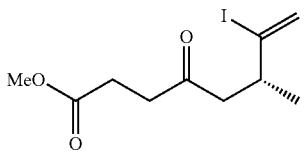

or a salt thereof.

In certain embodiments, the compound of Formula (II-1) is of the formula:

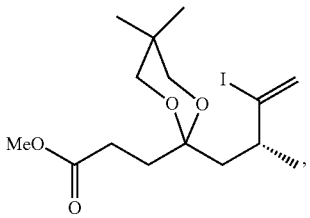

or a salt thereof.

In certain embodiments, the reaction to yield a compound of Formula (III-1) is carried out in the presence of a diol and an acid. In certain embodiments, the reaction is carried out in the presence of 2,2-dimethyl-1,3-propanediol and an acid. In certain embodiments, the reaction is carried out in the presence of 2,2-dimethyl-1,3-propanediol and p-toluenesulfonic acid. In certain embodiments, the reaction to yield a compound of Formula (III-1) is carried out in the presence of a diol, an acid, and an orthoformate. In certain embodiments, the reaction is carried out in the presence of 2,2-dimethyl-1,3-propanediol, p-toluenesulfonic acid, and trimethyl orthoformate. In certain embodiments, the reaction is carried out in a polar solvent such as acetonitrile. For example, in certain embodiments, the reaction is carried out in the presence of 2,2-dimethyl-1,3-propanediol (5 equiv.), p-toluenesulfonic acid hydrate (2 mol %), and trimethyl orthoformate (1.5 equiv), in MeCN, at room temperature (e.g., for approximately 20 hours).

Compounds

Also provided herein are compounds which are useful intermediates in the synthesis of halichondrins (e.g., halichondrins A, B, C), and analogs thereof. For example, provided herein are compounds of Formula (I-13):

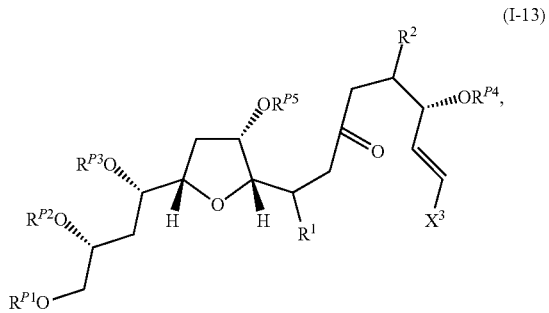

(I-13)

and salts thereof, wherein:
  $X^3$ is halogen or a leaving group;
  $R^1$ and $R^2$ are each independently hydrogen, halogen, or optionally substituted alkyl; and
  $R^{P1}$, $R^{P2}$, $R^{P3}$, $R^{P4}$, and $R^{P5}$ are each independently hydrogen, optionally substituted alkyl, optionally substituted acyl, or an oxygen protecting group.

Also provided herein are compounds of Formula (I-12):

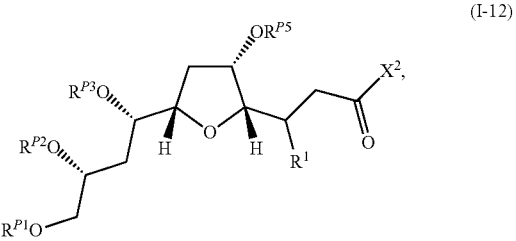

(I-12)

and salts thereof, wherein:
  $X^2$ is halogen, a leaving group, or —$SR^S$;
  $R^1$ and $R^2$ are each independently hydrogen, halogen, or optionally substituted alkyl; and
  $R^{P1}$, $R^{P2}$, $R^{P3}$, $R^{P4}$, and $R^{P5}$ are each independently hydrogen, optionally substituted alkyl, optionally substituted acyl, or an oxygen protecting group.

In certain embodiments, the compound of Formula (I-12) is a compound of Formula (I-12-S):

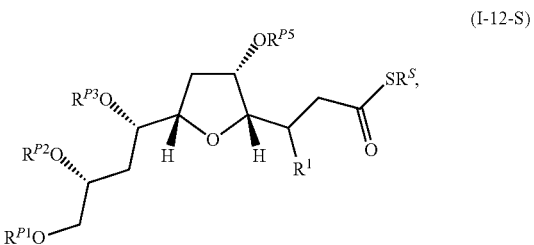

(I-12-S)

or a salt thereof, wherein:
  $R^S$ is optionally substituted alkyl, optionally substituted carbocyclyl, optionally substituted aryl, optionally substituted heterocyclyl, or optionally substituted heteroaryl.

Also provided herein are compounds of Formula (I-10):

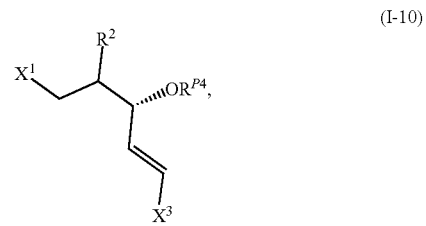

(I-10)

and salts thereof, wherein:
  $X^1$ and $X^3$ are each independently a halogen or a leaving group;
  $R^2$ is hydrogen, halogen, or optionally substituted alkyl; and
  $R^{P4}$ is hydrogen, optionally substituted alkyl, optionally substituted acyl, or an oxygen protecting group.

Provided herein are compounds of Formula (I-11):

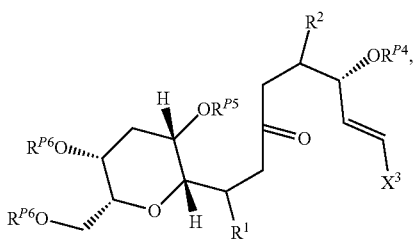

(I-11)

and salts thereof, wherein:

X³ is halogen or a leaving group;

R¹ and R² are each independently hydrogen, halogen, or optionally substituted alkyl; and $R^{P4}$, $R^{P}$, and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl.

Also provided herein are compound of Formula (I-9):

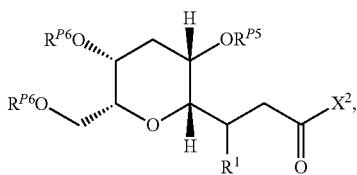

(I-9)

and salts thereof, wherein:

X² is halogen, a leaving group, or —SR$^S$;

R¹ and R² are each independently hydrogen, halogen, or optionally substituted alkyl; and $R^{P5}$ and $R^{P6}$ are independently hydrogen, optionally substituted alkyl, optionally substituted acyl, or an oxygen protecting group; optionally wherein two $R^{P6}$ are joined with the intervening atoms to form optionally substituted heterocyclyl.

In certain embodiments, a compound of Formula (I-9) is of Formula (I-9-S):

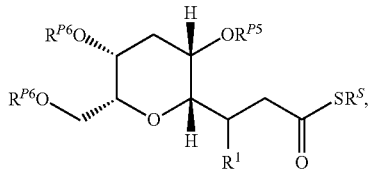

(I-9-S)

or a salt thereof, wherein:

R$^S$ is optionally substituted alkyl, optionally substituted carbocyclyl, optionally substituted aryl, optionally substituted heterocyclyl, or optionally substituted heteroaryl.

In another aspect, provided herein is a compound of the formula:

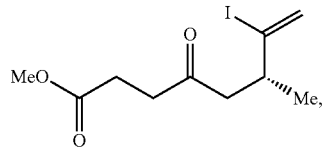

or a salt thereof.

In yet another aspect, provided herein is a compound of the formula:

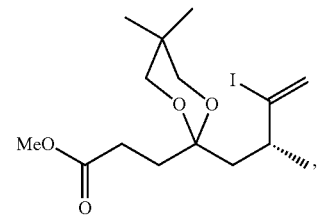 [SMILES: C=C(I)[C@H](C)CC1(CCC(=O)OC)OCC(C)(C)CO1]

or a salt thereof.

Groups X¹, X², X³

As defined herein, X¹ is halogen or a leaving group. In certain embodiments, X¹ is a halogen. In certain embodiments, X¹ is —Cl (i.e., chloride). In certain embodiments, X¹ is —Br (i.e., bromide). In certain embodiments, X¹ is —I (i.e., iodide). In certain embodiments, X¹ is —F (i.e., fluoride). In certain embodiments, X¹ is a leaving group.

As defined herein, X² is halogen, a leaving group, or —SR$^S$. In certain embodiments, X² is a halogen. In certain embodiments, X² is —Cl. In certain embodiments, X² is —Br. In certain embodiments, X² is —I. In certain embodiments, X² is —F. In certain embodiments, X² is a leaving group. In certain embodiments, X² is —SR$^S$.

As defined herein, R$^S$ is optionally substituted alkyl, optionally substituted carbocyclyl, optionally substituted aryl, optionally substituted heterocyclyl, or optionally substituted heteroaryl. In certain embodiments, R$^S$ is optionally substituted alkyl. In certain embodiments, R$^S$ is optionally substituted $C_{1-6}$ alkyl. In certain embodiments, R$^S$ is unsubstituted $C_{1-6}$ alkyl. In certain embodiments, R$^S$ is selected from the group consisting of methyl, ethyl, n-propyl, iso-propyl, n-butyl, iso-butyl, sec-butyl, and tert-butyl. In certain embodiments, R$^S$ is optionally substituted carbocyclyl. In certain embodiments, R$^S$ is optionally substituted aryl. In certain embodiments, R$^S$ is optionally substituted heterocyclyl. In certain embodiments, R$^S$ is optionally substituted heteroaryl. In certain embodiments, R$^S$ is optionally substituted 6-membered heteroaryl. In certain embodiments, R$^S$ is optionally substituted 6-membered heteroaryl comprising 1, 2, or 3 nitrogen atoms. In certain embodiments, R$^S$ is optionally substituted pyridyl. In certain embodiments, R$^S$ is unsubstituted pyridyl (Py). In certain embodiments, R$^S$ is optionally substituted 2-pyridyl. In certain embodiments, R$^S$ is unsubstituted 2-pyridyl (2-Py). In certain embodiments, R$^S$ is selected from the group consisting of:

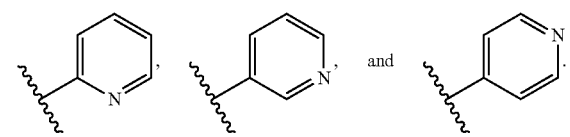 [SMILES: *c1ccccn1 ; *c1cccnc1 ; *c1ccncc1]

In certain embodiments, $R^S$ is

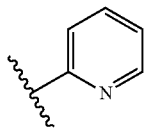 [SMILES: *c1ccccn1]

(2-Py).

As defined herein, $X^3$ is halogen or a leaving group. In certain embodiments, $X^3$ is a halogen. In certain embodiments, $X^3$ is —Cl. In certain embodiments, $X^3$ is —Br. In certain embodiments, $X^3$ is —I. In certain embodiments, $X^3$ is —F. In certain embodiments, $X^3$ is a leaving group.

Groups R, Ar, $R^1$, $R^2$, $R^5$, and $R^8$

As defined herein, R is optionally substituted alkyl, optionally substituted carbocyclyl, optionally substituted aryl, optionally substituted heteroaryl, or optionally substituted heterocyclyl. In certain embodiments, R is optionally substituted alkyl. In certain embodiments, R is optionally substituted $C_{1-6}$ alkyl. In certain embodiments, R is unsubstituted $C_{1-6}$ alkyl. In certain embodiments, R is optionally substituted $C_{1-3}$ alkyl. In certain embodiments, R is unsubstituted $C_{1-3}$ alkyl. In certain embodiments, R is selected from the group consisting of methyl, ethyl, n-propyl, iso-propyl, n-butyl, iso-butyl, sec-butyl, and tert-butyl. In certain embodiments, R is methyl. In certain embodiments, R is optionally substituted aryl. In certain embodiments, R is optionally substituted phenyl. In certain embodiments, R is phenyl (-Ph).

As defined herein, Ar is optionally substituted aryl or optionally substituted heteroaryl. In certain embodiments, Ar is optionally substituted aryl. In certain embodiments, Ar is optionally substituted phenyl. In certain embodiments, Ar is unsubstituted phenyl (-Ph).

As defined herein, $R^1$ is hydrogen, halogen, or optionally substituted alkyl. In certain embodiments, $R^1$ is hydrogen. In certain embodiments, $R^1$ is halogen. In certain embodiments, $R^1$ is optionally substituted alkyl. In certain embodiments, $R^1$ is optionally substituted $C_{1-6}$ alkyl. In certain embodiments, $R^1$ is unsubstituted $C_{1-6}$ alkyl. In certain embodiments, $R^1$ is optionally substituted $C_{1-3}$ alkyl. In certain embodiments, $R^1$ is unsubstituted $C_{1-3}$ alkyl. In certain embodiments, $R^1$ is selected from the group consisting of methyl, ethyl, n-propyl, iso-propyl, n-butyl, iso-butyl, sec-butyl, and tert-butyl. In certain embodiments, $R^1$ is methyl.

As defined herein, $R^2$ is hydrogen, halogen, or optionally substituted alky. In certain embodiments, $R^2$ is hydrogen. In certain embodiments, $R^2$ is halogen. In certain embodiments, $R^2$ is optionally substituted alkyl. In certain embodiments, $R^2$ is optionally substituted $C_{1-6}$ alkyl. In certain embodiments, $R^2$ is unsubstituted $C_{1-6}$ alkyl. In certain embodiments, $R^2$ is optionally substituted $C_{1-3}$ alkyl. In certain embodiments, $R^2$ is unsubstituted $C_{1-3}$ alkyl. In certain embodiments, $R^2$ is selected from the group consisting of methyl, ethyl, n-propyl, iso-propyl, n-butyl, iso-butyl, sec-butyl, and tert-butyl. In certain embodiments, $R^2$ is methyl.

As defined herein, $R^8$ is hydrogen, optionally substituted alkyl, optionally substituted carbocyclyl, optionally substituted aryl, optionally substituted heterocyclyl, optionally substituted heteroaryl, optionally substituted acyl, or an oxygen protecting group. In certain embodiments, $R^8$ is hydrogen. In certain embodiments, $R^8$ is optionally substituted alkyl. In certain embodiments, In certain embodiments, $R^8$ is optionally substituted $C_{1-6}$ alkyl. In certain embodiments, R is unsubstituted $C_{1-6}$ alkyl. In certain embodiments, $R^8$ is optionally substituted $C_{1-3}$ alkyl. In certain embodiments, $R^8$ is unsubstituted $C_{1-3}$ alkyl. In certain embodiments, $R^8$ is selected from the group consisting of methyl, ethyl, n-propyl, iso-propyl, n-butyl, iso-butyl, sec-butyl, and tert-butyl. In certain embodiments, $R^8$ is methyl. In certain embodiments, $R^8$ is ethyl. In certain embodiments, $R^8$ is benzyl (—$CH_2Ph$; "Bn").

As defined herein, $R^5$ is hydrogen, halogen, or optionally substituted alkyl. In certain embodiments, $R^5$ is hydrogen. In certain embodiments, $R^5$ is halogen. In certain embodiments, $R^3$ is optionally substituted alkyl. In certain embodiments, $R^5$ is optionally substituted $C_{1-6}$ alkyl. In certain embodiments, $R^5$ is unsubstituted $C_{1-6}$ alkyl. In certain embodiments, $R^5$ is optionally substituted $C_{1-3}$ alkyl. In certain embodiments, $R^5$ is unsubstituted $C_{1-3}$ alkyl. In certain embodiments, $R^5$ is selected from the group consisting of methyl, ethyl, n-propyl, iso-propyl, n-butyl, iso-butyl, sec-butyl, and tert-butyl. In certain embodiments, $R^5$ is methyl.

Groups $R^{P1}$, $R^{P2}$, $R^{P3}$, $R^{P4}$, $R^{P5}$, and $R^{P6}$

As defined herein, $R^{P1}$ is hydrogen, optionally substituted alkyl, optionally substituted acyl, or an oxygen protecting group. In certain embodiments, $R^{P1}$ is hydrogen. In certain embodiments, $R^{P1}$ is optionally substituted alkyl. In certain embodiments, In certain embodiments, $R^{P1}$ is optionally substituted $C_{1-6}$ alkyl. In certain embodiments, $R^{P1}$ is unsubstituted $C_{1-6}$ alkyl. In certain embodiments, $R^{P1}$ is optionally substituted $C_{1-3}$ alkyl. In certain embodiments, $R^{P1}$ is unsubstituted $C_{1-3}$ alkyl. In certain embodiments, $R^{P1}$ is selected from the group consisting of methyl, ethyl, n-propyl, iso-propyl, n-butyl, iso-butyl, sec-butyl, and tert-butyl. In certain embodiments, $R^{P1}$ is optionally substituted acyl. In certain embodiments, $R^{P1}$ is an oxygen protecting group. In certain embodiments, $R^{P1}$ is optionally substituted allyl. In certain embodiments, $R^{P1}$ is allyl. In certain embodiments, $R^{P1}$ is optionally substituted silyl. In certain embodiments, $R^{P1}$ is trialkylsilyl. In certain embodiments, $R^{P1}$ is triethylsilyl (—$SiEt_3$; "TES"). In certain embodiments, $R^{P1}$ is trimethylsilyl (—$SiMe_3$; "TMS"). In certain embodiments, $R^{P1}$ is tert-butyl dimethylsilyl (—$Sit\text{-}BuMe_2$; "TBS"). In certain embodiments, $R^{P1}$ is tert-butyl diphenylsilyl (—$Sit\text{-}BuPh_2$; "TBDPS"). In certain embodiments, $R^{P1}$ is an optionally substituted benzyl protecting group. In certain embodiments, $R^{P1}$ is benzyl (—$CH_2Ph$; "Bn"). In certain embodiments, $R^{P1}$ is a methoxybenzyl protecting group. In certain embodiments, $R^{P1}$ is para-methoxybenzyl:

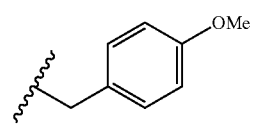 [SMILES: *Cc1ccc(OC)cc1]

("MPM" or "PMB").

In certain embodiments, $R^{P1}$ and $R^{P2}$ are joined with the intervening atoms to form optionally substituted heterocyclyl.

As defined herein, $R^{P2}$ is hydrogen, optionally substituted alkyl, optionally substituted acyl, or an oxygen protecting group. In certain embodiments, $R^{P2}$ is hydrogen. In certain embodiments, $R^{P2}$ is optionally substituted alkyl. In certain embodiments, $R^{P2}$ is optionally substituted $C_{1-6}$ alkyl. In certain embodiments, $R^{P2}$ is unsubstituted $C_{1-6}$ alkyl. In certain embodiments, $R^{P2}$ is optionally substituted $C_{1-3}$ alkyl. In certain embodiments, $R^{P2}$ is unsubstituted $C_{1-3}$ alkyl. In certain embodiments, $R^{P2}$ is selected from the group consisting of methyl, ethyl, n-propyl, iso-propyl, n-butyl, iso-butyl, sec-butyl, and tert-butyl. In certain embodiments, $R^{P2}$ is optionally substituted acyl. In certain embodiments, $R^{P2}$ is an oxygen protecting group. In certain embodiments, $R^{P2}$ is optionally substituted allyl. In certain embodiments, $R^{P2}$ is allyl. In certain embodiments, $R^{P2}$ is optionally substituted silyl. In certain embodiments, $R^{P2}$ is trialkylsilyl. In certain embodiments, $R^{P2}$ is triethylsilyl (—SiEt$_3$; "TES"). In certain embodiments, $R^{P2}$ is trimethylsilyl (—SiMe$_3$; "TMS"). In certain embodiments, $R^{P2}$ is tert-butyl dimethylsilyl (—Sit-BuMe$_2$; "TBS"). In certain embodiments, $R^{P2}$ is tert-butyl diphenylsilyl (—Sit-BuPh$_2$; "TBDPS"). In certain embodiments, $R^{P2}$ is an optionally substituted benzyl protecting group. In certain embodiments, $R^{P2}$ is benzyl (—CH$_2$Ph; "Bn"). In certain embodiments, $R^{P2}$ is a methoxybenzyl protecting group. In certain embodiments, $R^{P2}$ is para-methoxybenzyl:

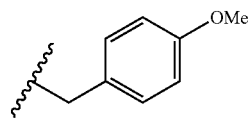 [SMILES: *Cc1ccc(OC)cc1]

("MPM" or "PMB").

In certain embodiments, $R^{P3}$ and $R^{P3}$ are joined with the intervening atoms to form optionally substituted heterocyclyl.

As defined herein, $R^{P3}$ is hydrogen, optionally substituted alkyl, optionally substituted acyl, or an oxygen protecting group. In certain embodiments, $R^{P3}$ is hydrogen. In certain embodiments, $R^{P3}$ is optionally substituted alkyl. In certain embodiments, $R^{P3}$ is optionally substituted $C_{1-6}$ alkyl. In certain embodiments, $R^{P3}$ is unsubstituted $C_{1-6}$ alkyl. In certain embodiments, $R^{P3}$ is optionally substituted $C_{1-3}$ alkyl. In certain embodiments, $R^{P3}$ is unsubstituted $C_{1-3}$ alkyl. In certain embodiments, $R^{P3}$ is selected from the group consisting of methyl, ethyl, n-propyl, iso-propyl, n-butyl, iso-butyl, sec-butyl, and tert-butyl. In certain embodiments, $R^{P3}$ is optionally substituted acyl. In certain embodiments, $R^{P3}$ is an oxygen protecting group. In certain embodiments, $R^{P3}$ is optionally substituted allyl. In certain embodiments, $R^{P3}$ is allyl. In certain embodiments, $R^{P3}$ is optionally substituted silyl. In certain embodiments, $R^{P3}$ is trialkylsilyl. In certain embodiments, $R^{P3}$ is triethylsilyl (—SiEt$_3$; "TES"). In certain embodiments, $R^{P3}$ is trimethylsilyl (—SiMe$_3$; "TMS"). In certain embodiments, $R^{P3}$ is tert-butyl dimethylsilyl (—Sit-BuMe$_2$; "TBS"). In certain embodiments, $R^{P3}$ is tert-butyl diphenylsilyl (—Sit-BuPh$_2$; "TBDPS"). In certain embodiments, $R^{P3}$ is an optionally substituted benzyl protecting group. In certain embodiments, $R^{P3}$ is benzyl (—CH$_2$Ph; "Bn"). In certain embodiments, $R^{P3}$ is a methoxybenzyl protecting group. In certain embodiments, $R^{P3}$ is para-methoxybenzyl:

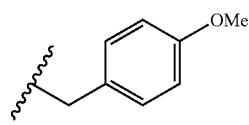 [SMILES: *Cc1ccc(OC)cc1]

("MPM" or "PMB").

As defined herein, $R^{P4}$ is hydrogen, optionally substituted alkyl, optionally substituted acyl, or an oxygen protecting group. In certain embodiments, $R^{P4}$ is hydrogen. In certain embodiments, $R^{P4}$ is optionally substituted alkyl. In certain embodiments, $R^{P4}$ is optionally substituted $C_{1-6}$ alkyl. In certain embodiments, $R^{P4}$ is unsubstituted $C_{1-6}$ alkyl. In certain embodiments, $R^{P4}$ is optionally substituted $C_{1-3}$ alkyl. In certain embodiments, $R^{P4}$ is unsubstituted $C_{1-3}$ alkyl. In certain embodiments, $R^{P4}$ is selected from the group consisting of methyl, ethyl, n-propyl, iso-propyl, n-butyl, iso-butyl, sec-butyl, and tert-butyl. In certain embodiments, $R^{P4}$ is optionally substituted acyl. In certain embodiments, $R^{P4}$ is an oxygen protecting group. In certain embodiments, $R^{P4}$ is optionally substituted allyl. In certain embodiments, $R^{P4}$ is allyl. In certain embodiments, $R^{P4}$ is optionally substituted silyl. In certain embodiments, $R^{P4}$ is trialkylsilyl. In certain embodiments, $R^{P4}$ is triethylsilyl (—SiEt$_3$; "TES"). In certain embodiments, $R^{P4}$ is trimethylsilyl (—SiMe$_3$; "TMS"). In certain embodiments, $R^{P4}$ is tert-butyl dimethylsilyl (—Sit-BuMe$_2$; "TBS"). In certain embodiments, $R^{P4}$ is tert-butyl diphenylsilyl (—Sit-BuPh$_2$; "TBDPS"). In certain embodiments, $R^{P4}$ is an optionally substituted benzyl protecting group. In certain embodiments, $R^{P4}$ is benzyl (—CH$_2$Ph; "Bn"). In certain embodiments, $R^{P4}$ is a methoxybenzyl protecting group. In certain embodiments, $R^{P4}$ is para-methoxybenzyl:

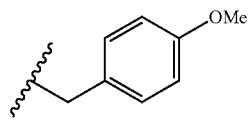 [SMILES: *Cc1ccc(OC)cc1]

("MPM" or "PMB").

As defined herein, $R^{P5}$ is hydrogen, optionally substituted alkyl, optionally substituted acyl, or an oxygen protecting group. In certain embodiments, $R^{P5}$ is hydrogen. In certain embodiments, $R^{P5}$ is optionally substituted alkyl. In certain embodiments, $R^{P5}$ is optionally substituted $C_{1-6}$ alkyl. In certain embodiments, $R^{P5}$ is unsubstituted $C_{1-6}$ alkyl. In certain embodiments, $R^{P5}$ is optionally substituted $C_{1-3}$ alkyl. In certain embodiments, $R^{P5}$ is unsubstituted $C_{1-3}$ alkyl. In certain embodiments, $R^{P5}$ is selected from the group consisting of methyl, ethyl, n-propyl, iso-propyl, n-butyl, iso-butyl, sec-butyl, and tert-butyl. In certain embodiments, $R^{P5}$ is optionally substituted acyl. In certain embodiments, $R^{P5}$ is an oxygen protecting group. In certain embodiments, $R^{P5}$ is optionally substituted allyl. In certain embodiments, $R^{P5}$ is allyl. In certain embodiments, $R^{P5}$ is optionally substituted silyl. In certain embodiments, $R^{P5}$ is trialkylsilyl. In certain embodiments, $R^{P5}$ is triethylsilyl (—SiEt$_3$; "TES"). In certain embodiments, $R^{P5}$ is trimethylsilyl (—SiMe$_3$; "TMS"). In certain embodiments, $R^{P5}$ is tert-butyl dimethylsilyl (—Sit-BuMe$_2$; "TBS"). In certain embodiments, $R^{P5}$ is tert-butyl diphenylsilyl (—Sit-BuPh$_2$; "TBDPS"). In certain embodiments, $R^{P5}$ is an optionally substituted benzyl protecting group. In certain embodiments, $R^{P5}$ is benzyl (—CH$_2$Ph; "Bn"). In certain embodiments, $R^{P5}$ is a methoxybenzyl protecting group. In certain embodiments, $R^{P5}$ is para-methoxybenzyl:

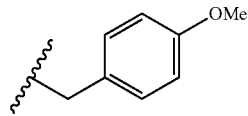 [SMILES: *Cc1ccc(OC)cc1]

("MPM" or "PMB").

As defined herein, $R^{P6}$ is hydrogen, optionally substituted alkyl, optionally substituted acyl, or an oxygen protecting group; optionally wherein two $R^{P6}$ are joined with the intervening atoms to form optionally substituted heterocyclyl. In certain embodiments, $R^{P6}$ is hydrogen. In certain embodiments, $R^{P6}$ is optionally substituted alkyl. In certain embodiments, $R^{P6}$ is optionally substituted $C_{1-6}$ alkyl. In certain embodiments, $R^{P6}$ is unsubstituted $C_{1-6}$ alkyl. In certain embodiments, $R^{P6}$ is optionally substituted $C_{1-3}$ alkyl. In certain embodiments, $R^{P6}$ is unsubstituted $C_{1-3}$ alkyl. In certain embodiments, $R^{P6}$ is selected from the group consisting of methyl, ethyl, n-propyl, iso-propyl, n-butyl, iso-butyl, sec-butyl, and tert-butyl. In certain embodiments, $R^{P6}$ is optionally substituted acyl. In certain embodiments, $R^{P6}$ is an oxygen protecting group. In certain embodiments, $R^{P6}$ is optionally substituted allyl. In certain embodiments, $R^{P6}$ is allyl. In certain embodiments, $R^{P6}$ is optionally substituted silyl. In certain embodiments, $R^{P6}$ is trialkylsilyl. In certain embodiments, $R^{P6}$ is triethylsilyl (—SiEt$_3$; "TES"). In certain embodiments, $R^{P6}$ is trimethylsilyl (—SiMe$_3$; "TMS"). In certain embodiments, $R^{P6}$ is tert-butyl dimethylsilyl (—Sit-BuMe$_2$; "TBS"). In certain embodiments, $R^{P6}$ is tert-butyl diphenylsilyl (—Sit-BuPh$_2$; "TBDPS"). In certain embodiments, $R^{P6}$ is an optionally substituted benzyl protecting group. In certain embodiments, $R^{P6}$ is benzyl (—CH$_2$Ph; "Bn"). In certain embodiments, $R^{P6}$ is a methoxybenzyl protecting group. In certain embodiments, $R^{P6}$ is para-methoxybenzyl:

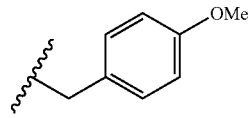

("MPM" or "PMB"). In certain embodiments, two $R^{P6}$ are joined with the intervening atoms to form optionally substituted heterocyclyl. In certain embodiments, two $R^{P6}$ are joined with the intervening atoms to form optionally substituted six-membered heterocyclyl. In certain embodiments, two $R^{P6}$ are joined with the intervening atoms to form a ring of the formula:

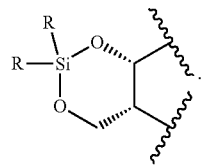

In certain embodiments, two $R^{P6}$ are joined with the intervening atoms to form a ring of the formula:

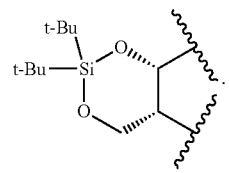

As defined herein, $R^{P9}$ is hydrogen, optionally substituted alkyl, optionally substituted acyl, or an oxygen protecting group. In certain embodiments, $R^{P9}$ is hydrogen. In certain embodiments, $R^{P9}$ is optionally substituted alkyl. In certain embodiments, $R^{P9}$ is optionally substituted $C_{1-6}$ alkyl. In certain embodiments, $R^{P9}$ is unsubstituted $C_{1-6}$ alkyl. In certain embodiments, $R^{P9}$ is optionally substituted $C_{1-3}$ alkyl. In certain embodiments, $R^{P9}$ is unsubstituted $C_{1-3}$ alkyl. In certain embodiments, $R^{P9}$ is selected from the group consisting of methyl, ethyl, n-propyl, iso-propyl, n-butyl, iso-butyl, sec-butyl, and tert-butyl. In certain embodiments, $R^{P9}$ is optionally substituted acyl. In certain embodiments, $R^{P9}$ is an oxygen protecting group. In certain embodiments, $R^{P9}$ is optionally substituted allyl. In certain embodiments, $R^{P9}$ is allyl. In certain embodiments, $R^{P9}$ is optionally substituted silyl. In certain embodiments, $R^{P9}$ is trialkylsilyl. In certain embodiments, $R^{P9}$ is triethylsilyl (—SiEt$_3$; "TES"). In certain embodiments, $R^{P9}$ is trimethylsilyl (—SiMe$_3$; "TMS"). In certain embodiments, $R^{P9}$ is tert-butyl dimethylsilyl (—Sit-BuMe$_2$; "TBS"). In certain embodiments, $R^{P9}$ is tert-butyl diphenylsilyl (—Sit-BuPh$_2$; "TBDPS"). In certain embodiments, $R^{P9}$ is an optionally substituted benzyl protecting group. In certain embodiments, $R^{P9}$ is benzyl (—CH$_2$Ph; "Bn"). In certain embodiments, $R^{P9}$ is a methoxybenzyl protecting group. In certain embodiments, $R^{P9}$ is para-methoxybenzyl:

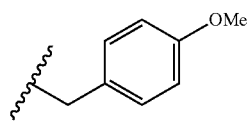 [SMILES: *Cc1ccc(OC)cc1]

("MPM" or "PMB"). In certain embodiments, two $R^{P9}$ are joined together with the intervening atoms. In certain embodiments, two $R^{P9}$ are joined together with the intervening atoms to form:

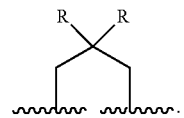

In certain embodiments, two $R^{P9}$ are joined together with the intervening atoms to form:

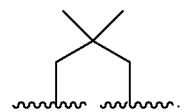

In certain embodiments, two $R^{P9}$ are joined together with the intervening atoms to form optionally substituted heterocyclyl. In certain embodiments, two $R^{P9}$ are joined together to form

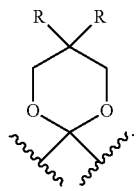

In certain embodiments, two $R^{P9}$ are joined together to form

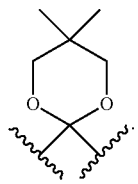 [SMILES: *C1(*)OCC(C)(C)CO1]

Group R is as defined herein.

EXAMPLES

Fe/Cu-Mediated Ketolization Reactions

For a feasibility study of the reductive-coupling, the substrates shown in FIG. 1A were chosen to begin with. The first attempt under the arbitrarily chosen condition [2a (5 equiv.), 1a (1 equiv.), MnPc (10 mol %), CuCN (1 equiv.), LiCl (3 equiv.), THF (C=0.2 M), rt, 6 hr] gave 3 in 35% isolated yield. The coupling conditions were optimized, including (1) radical initiator and loading (Relative reactivity of radical initiators tested was roughly in the following order: Fe(TMHD)$_3$>Fe(DBM)$_3$>CoPc>Fe(acac)$_3$~ZnPc> MnPc~FePc), (2) copper source (several Cu(I) salts were examined: CuCl, CuBr, CuI, CuCN, and CuTc gave 62%, 20%, 58%, 12%, and 10% yields, respectively; also, replacement of Cu(I) salts with Cu(II) salts was studied: CuCl$_2$ and CuBr$_2$ yielded 2a in 76% and 32%, respectively), (3) LiCl effect (LiCl, LiBr, and LiI were tested), (4) 1a:2a molar ratio (The molar ratios of 1a:2a=1.0:1.5, 1.0:2.0, 1.0:3.0 were tested), (5) reducing metal (Mn- and Zn-powders were tested), (6) solvent and concentration (concentration effects were studied with C=0.2M, 0.3M and 0.4M, but no significant difference was noticed. Thus, C=0.4M was chosen for the study), and (7) additives. Through this study, as an example, the condition of [1a (1.0 equiv.), 2a (3.0 equiv.), Fe(TMHD)$_3$ (10 mol %; 4 in FIG. 1B), CuCl$_2$ (1.0 equiv.), Mn (2 equiv.), LiCl (3 equiv.), DME (C 0.4 M), 0° C., 15 h] was found effective for the (1a+2a)-coupling (76% isolated yield). See Method A in FIG. 2.

This Fe/Cu-mediated method exhibited one appealing reactivity-profile; that was, unlike other state of the art methods, this Fe/Cu-mediated method allowed selectively to activate an alkyl iodide over a vinyl or aryl iodide, e.g., compounds 1j-m. This selectivity is of great importance to the synthesis of complex molecules. In particular, this opened up the possibility of synthesizing 8a, the C20-C26 building block of halichondrins, via the coupling of 6 with 7. Previously, this coupling was done in multiple steps, i.e., Co/Cr-mediated coupling, followed by oxidation: Kim, D.—S.; Dong, C.-G.; Kim, J. T.; Guo, H.; Huang, J.; Tiseni, P. S.; Kishi, Y. *J. Am. Chem. Soc.* 2009, 131, 15636; Dong, C.-G.; Henderson, J. A.; Kaburagi, Y.; Sasaki, T.; Kim, D.—S.; Kim, J. T.; Urabe, D.; Guo, H.; Kishi, Y. *J. Am. Chem. Soc.* 2009, 131, 15642.

Under the condition of Method A (FIG. 2), the one-pot ketone coupling gave the desired product 8a. The coupling was then further optimized. The activation rate of alkyl iodide in 7 was slower than that in the model 1j. With a higher loading of Fe(TMHD)$_3$, the coupling rate was accelerated as expected. With 13~15 mol % catalyst, the (6+7)-coupling gave the desired ketone 8a (75% isolated yield), along with a trace amount of 8b (<1% yield), in 15 g-scale experiments. Similarly, the Fe/Cu-mediated coupling with the vinylbromide corresponding to 7 gave the desired product in a comparable yield.

As illustrated in the transformation of 6+7→8a, the Fe/Cu-mediated one-pot ketone synthesis, initiated with Fe(TMHD)$_3$, exhibited a profile of reactivity, which might be difficult to achieve by other state of the art ketone syntheses.

During further optimization, it was recognized that in order for Fe(TMHD)$_3$ to function as a radical initiator, Fe(III) should be reduced to Fe(II) by Mn metal. The reduction released one molecule of β-diketone, which consumed some of 6 in a non-productive manner. This side-reaction could be avoided with use of a Fe(II)-initiator. For this reason, various radical initiators were screened for the Cu-mediated ketone coupling. Among them, FeBr$_2$(dppb) was found to promote the (1a+2a)-coupling well. Phosphine complexes FeBr$_2$(dppb), FeCl$_2$(dppb), FeBr$_2$(dppe), FeCl$_2$(dppe), and FeBr$_2$(PPh$_3$)$_2$ gave product 3a in 90%, 79%, 54%, 46% and 48%, respectively, under the coupling condition Method B-1 (FIG. 2). Through optimization, it was found that the coupling was effectively achieved, for example, under the condition: FeBr$_2$(dppb) (5 mol %), acid chloride (1.0 equiv.), iodide (1.2 equiv.), CuCl$_2$ (1.0 equiv.), LiCl (3 equiv.), Mn (2 equiv.), DME (C=0.4 M), 0° C., 15 hr. See, e.g., Britovsek, G. J. P.; England, J.; Spitzmesser, S. K.; White, A. J. P.; Williams, D. J. *Dalton Trans.* 2005, 945, and references cited therein. Under the optimized condition, the coupling was tested with the molar ratio of 1a/2a being 1.2/1.0 and 1.0/1.2, to give 3a in 90% and 87% isolated yield, respectively. With 1.2/1.0 and 1.0/1.2 ratios of nucleophile and electrophile, the coupling efficiency was studied for the substrates listed in Method B-1 and B-2 in FIG. 2.

The FeBr$_2$(dppb)-condition was applied for the (6+7)-coupling, to give 8a in 72% isolated yield. The coupling yield was further improved up to 80% yield, by replacing FeBr$_2$(dppb) for FeBr$_2$-complex prepared from SciOPP-ligand, recently reported by Nakamura and coworkers. See, e.g., Hatakeyama, T.; Fujiwara, Y.; Okada, Y.; Itoh, T.; Hashimoto, T.; Kawamura, S.; Ogata, K. Takaya, H.; Nakamura, M. *Chem. Lett.* 2011, 40, 1030.

Phosphine-based FeBr$_2$-catalysts allowed an efficient one-pot ketone synthesis, even with a near 1:1 molar ratio of nucleophiles and electrophiles. This approach was applied to a synthesis of vinyl iodide 13, a left half "building block" in the halichondrin series, as well as related vinyl iodide 11. In the 9-series, we were able to prepare the acid chloride and showed that the coupling gave the desired product 11 in 20-25% overall yield from the carboxylic acid. With FeBr$_2$(dppb) and FeBr$_2$(SciOPP), 11 was obtained in 20% and 25% yields, respectively. Under these circumstances, a 2-thiopyridine ester as used as an alternative electrophile, because it was proved to be an effective electrophile in the Zr/Ni-mediated one-pot ketone synthesis. See, e.g., Araki, M.; Sakata, S.; Takei, H.; Mukaiyama, T. *Bull. Chem. Soc. Jpn.* 1974, 47, 1777; Onaka, M.; Matsuoka, Y.; Mukaiyama, T. *Chem. Lett.* 1981, 531.

With this background, the (1a+2b→3a)-coupling under the condition of Method B-1 was carried out, and the desired product was obtained in ~15% yield. The 2-thiopyridine ester was found to be stable in the presence of CuI, suggesting the coupling in the presence of CuI, instead of CuCl$_2$ (Method C). The coupling efficiency under this condition was studied for each substrate listed in FIG. 2.

Figure 3:
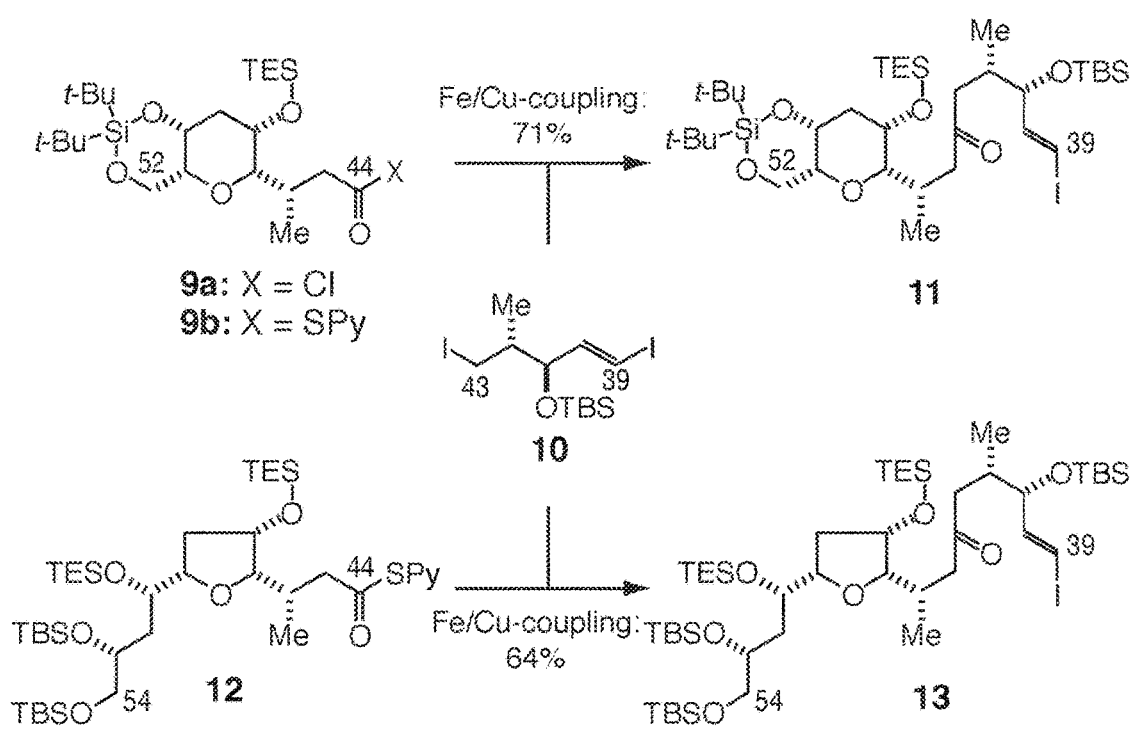
FIG. 3 shows exemplary Fe/Cu-mediated coupling reactions forming intermediates useful in the synthesis of halichondrins and analogs thereof (compounds 11 and 13).

The Fe/Cu-mediated one-pot ketone synthesis under the condition of Method C furnished vinyl iodide 13, the "left half" building block in the halichondrin series, as well as closely related vinyl iodide 11, with a 1.0:1.2 molar ratio of electrophile and nucleophile (FIG. 3). The new route had a few appealing aspects, including (1) a higher degree of convergence, and (2) introduction of the C39 vinyl group before the ketone coupling via a standard transformation of terminal acetylene to trans-vinyl iodide. In the previous synthesis, trans-vinyl iodide at C39 was introduced via Takai trans-iodoolefination; see: Takai, K.; Nitta, K.; Utimoto, K. *J. Am. Chem. Soc.* 1986, 108, 7408. (b) Takai, K.; Ichiguchi, T.; Hikasa, S. *Synlett* 1999, 1268.

Figure 4:
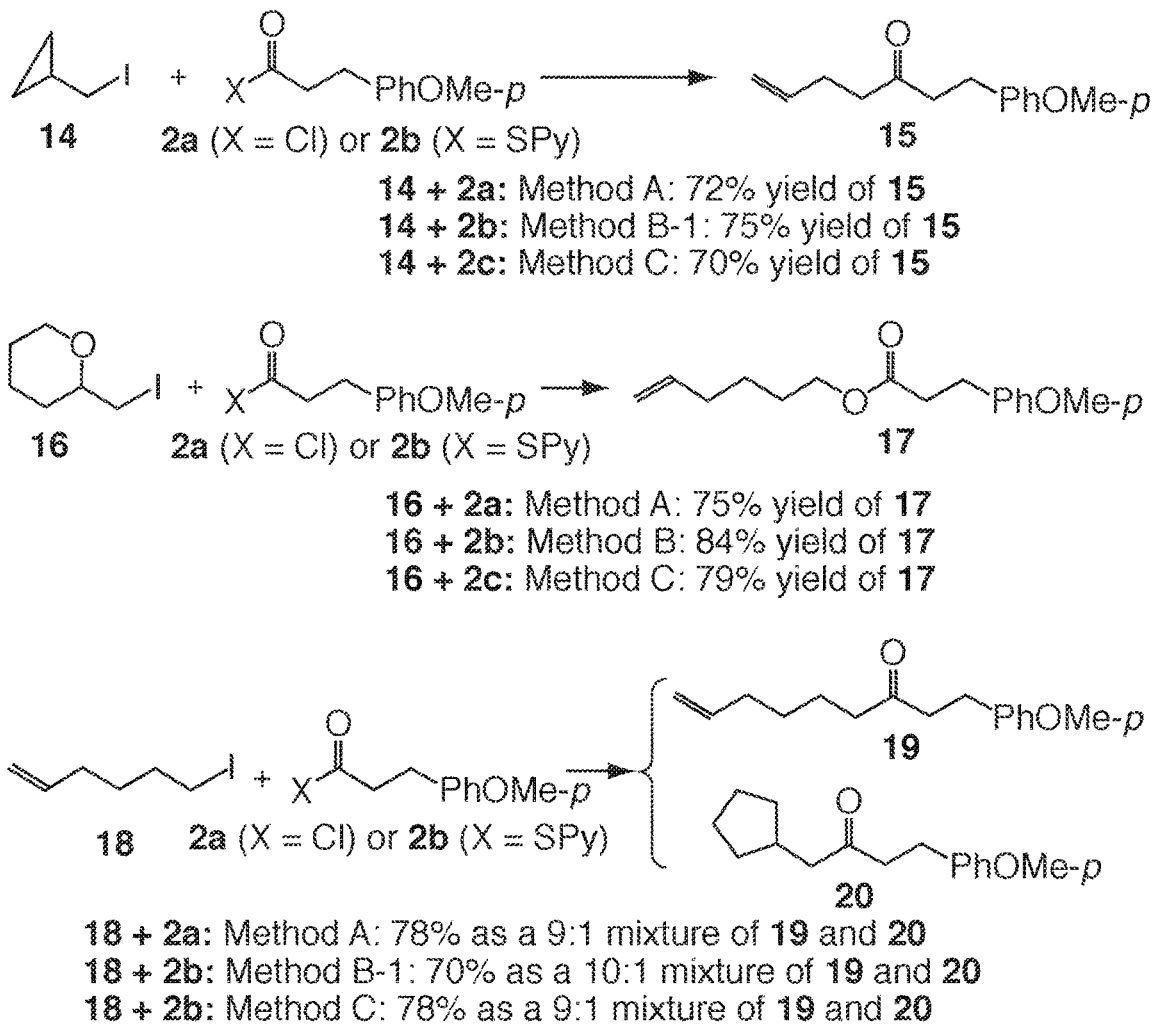
FIG. 4 outlines the Fe/Cu-mediated coupling reactions with common radical probes.
Figure 5:
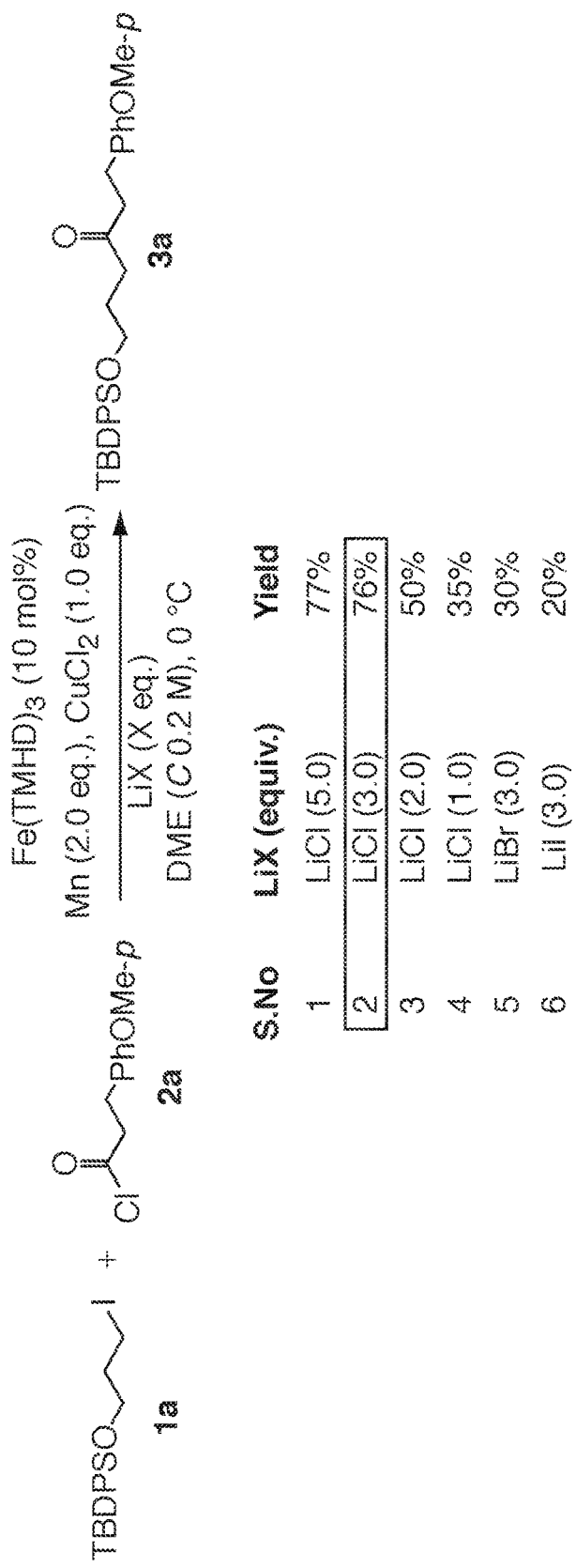
FIG. 5 outlines the results of lithium halide screening. LiCl, LiBr, and LiI were found to be useful in the coupling reactions described herein.
Figure 6:
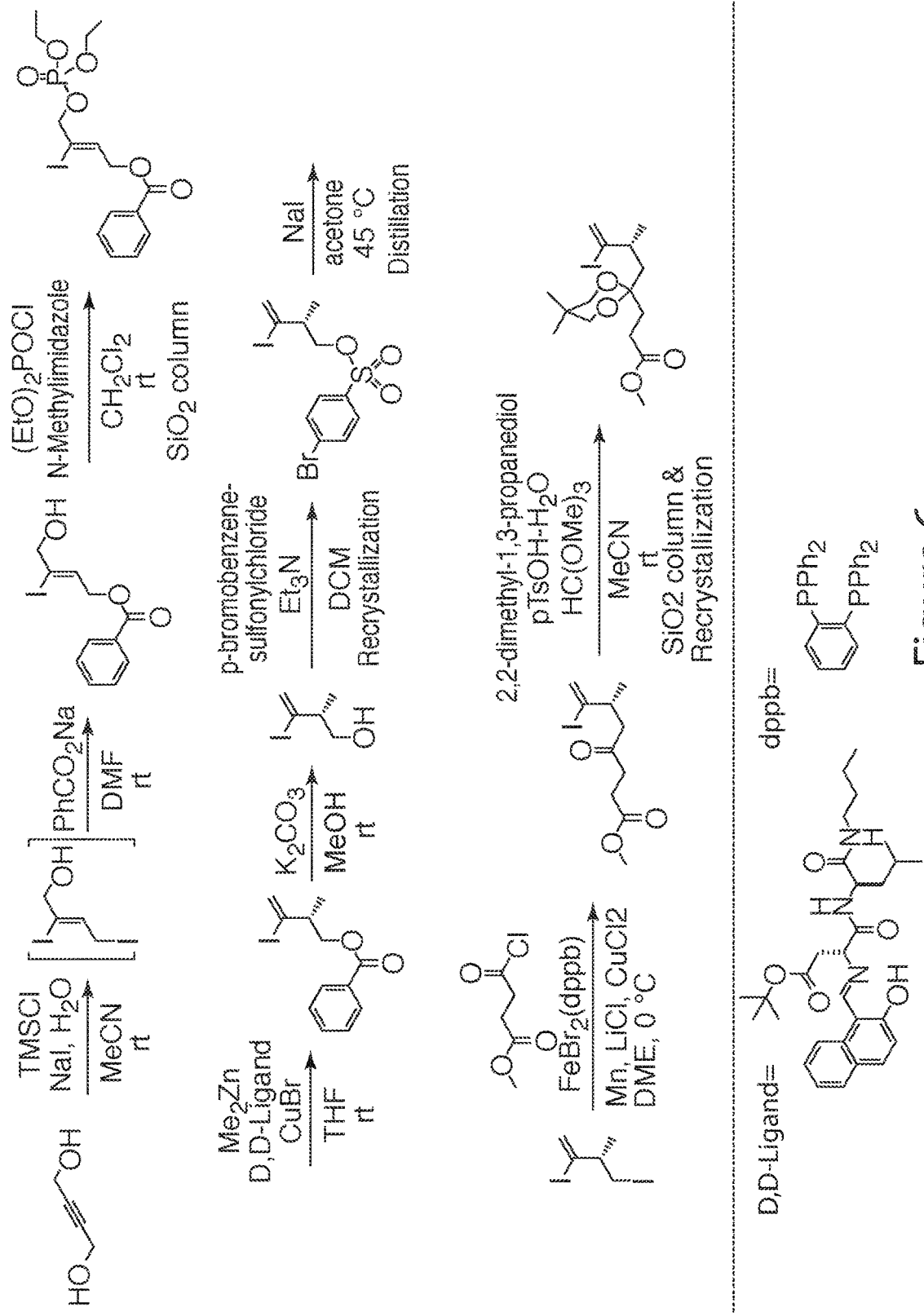
FIG. 6 shows an exemplary synthesis of a C20-C26 building block of halichondrins.

Lastly, the behavior of common radical probes was tested under the three coupling conditions (FIG. 4). As expected, the observed results demonstrated that a radical intermediate(s) was involved in all the three coupling methods.

The Fe/Cu-mediated one-pot ketone syntheses exemplified herein, in some instances, allowed selectively to activate alkyl iodides over vinyl iodides for one-pot ketone synthesis. The newly developed method was applied to the synthesis of vinyl iodide/ketone 8a, the C20-C26 building block of halichondrins, as well as vinyl iodide/ketone 13, the "left half" of halichondrins.

General Procedures

NMR spectra were recorded on a Varian Inova 600 MHz, 500 MHz, or 400 MHz spectrometer. Chemical shifts are reported in parts per million (ppm). For $^1$H NMR spectra ($CDCl_3$ and $C_6D_6$), the residual solvent peak was used as the internal reference (7.26 ppm in $CDCl_3$; 7.16 ppm in $C_6D_6$), while the central solvent peak as the reference (77.0 ppm in $CDCl_3$; 128.0 ppm in $C_6D_6$) for $^{13}$C NMR spectra. In reporting spectral data, the following abbreviations were used: s=singlet, d=doublet, t=triplet, q=quartet, m=multiplet, dd=doublet, td=triplet doublet, qd=quartet doublet. High resolution mass spectra (HRMS) were obtained on an Agilent 6210 Time-of-Flight LC/MC Machine and were reported in units of m/z. Optical rotations were measured at 20° C. using a Perkin-Elmer 241 polarimeter. IR spectra were recorded on a Bruker Alpha FT-IR spectrometer. Analytical and semi-preparative thin layer chromatography (TLC) was performed with E. Merck pre-coated TLC plates, silica gel 60 F254, layer thickness 0.25 and 1.00 mm, respectively. TLC plates were visualized by staining with p-anisaldehyde or phosphomolybdic acid stain. Flash chromatography separations were performed on E. Merck Kieselgel 60 (230-400 mesh) silica gel. All moisture sensitive reactions were conducted under an inert atmosphere.

Experimental Materials

Bis(diphenylphosphino)benzene (98%, Strem Chemimcals), 1,2-Bis[bis[3,5-di(t-butyl)phenyl]phosphino] benzene (97%+, Wako Pure Chemicals), Iron (II) bromide ($FeBr_2$, ~10 mesh, 99.999%, Sigma-Aldrich), Ethyl 4-chloro-4-oxobutyrate (97%, Alfa Aesar), Lithium Chloride (>99%, Sigma-Aldrich), Manganese (>99.9%, Sigma-Aldrich), Copper (II) chloride ($CuCl_2$, 99%, Sigma-Aldrich), Copper (I) iodide (CuI, >99.5%, Sigma-Aldrich), Bis(cyclopentadienyl)zirconium(IV) dichloride ($Cp_2ZrCl_2$, >98%, Sigma-Aldrich), 2,2,6,6-tetramethyl-3,5-heptanedionate (95%, Oakwood Chemical), 1,2-1,2-Dimethoxy ethane (DME, 99.5%, inhibitor-free, Sigma-Aldrich) were purchased as indicated and used without further purification. Others were commercial grade and were used as supplied.

Synthesis of Iron Complexes

Synthesis of Iron (III) tris(2,2,6,6-tetramethyl-3,5-heptanedionate) ($Fe(TMHD)_3$) 4

An oven dried 500 mL two-necked flask equipped with a Teflon-coated egg shaped magnetic stirring bar (2.5 cm) and a reflux condenser was charged with a solution of Iron(III) chloride hexahydrate (10 g, 36.9 mmol) in ethanol (100 mL) and followed by water (100 mL), 2,2,6,6-tetramethyl-3,5-heptanedionate (20.04 g, 110.1 mmol) and sodium acetate (15.0 g, 110.1 mmol) was charged. The reaction flask was heated to 60° C. for 3 hours, at this time the orange colored precipitate was formed. The reaction mixture was cooled to room temperature, 100 mL of water was introduced to the reaction mixture. Filtered the orange solid and was washed with 200 mL of ethanol. The resulting orange solid (19.3 g) was dried under high vacuum for 12 hours. Recrystallization: The above obtained orange solid (19.3 g) was dissolved in 300 mL of ethyl acetate upon heating to 60° C. Filtered the ethyl acetate solution through a filter paper and the resulting filtrate (ethyl acetate) was concentrated under reduced pressure afforded pure crystalline orange solid 4 (18.3 g) in 82% yield.

Synthesis of $FeBr_2$(dppb) 5a

An oven dried 200 mL two-necked flask equipped with a magnetic stirring bar and a reflux condenser was charged with a solution of anhydrous Iron (II) bromide (1.5 g, 6.95 mmol) and 1,2-bis (diphenylphosphino) benzene (3.41 g, 7.65 mmol) in ethanol (70 mL). The reaction flask was heated to 80° C. for 18 hours, at this time pale brown colored precipitate was formed. The reaction mixture was cooled to room temperature. Filtered the brown solid and was washed with 100 mL of hot ethanol. The resulting yellowish brown solid 5a (3.54 g, 77%) was dried under high vacuum for 12 hours.

Synthesis of $FeBr_2$(SciOPP) 5b

See, e.g., Takaya, H.; Nakajima, S.; Nakagawa, N.; Isozaki, K.; Iwamoto, T.; Imayoshi, R.; Gower, N. J.; Adak, L.; Hatakeyama, T.; Honma, T.; Takagaki, M.; Sunada, Y.; Nagashima, H.; Hashizume, D.; Takahashi, O.; Nakamura, M. Bull. Chem. Soc. Jpn. 2015, 88, 410-418. An oven dried 200 mL two-necked flask equipped with a magnetic stirring bar and a reflux condenser was charged with a solution of anhydrous iron (II) bromide (1.5 g, 6.95 mmol) and 1,2-bis (bis(3,5-di-tert-butylphenyl)phosphino)benzene (6.84 g, 7.65 mmol) in ethanol (70 mL). The reaction flask was heated to 80° C. for 18 hours, at this time pale brown colored precipitate was formed. The reaction mixture was cooled to room temperature. Filtered the brown solid and was washed with 50 mL of hot ethanol. The resulting pale brown solid 5b (5.01 g, 65%) was dried under high vacuum for 12 hours.

Synthesis of Substrates

Compounds Id, Im were prepared following literature procedures. See, e.g., Lee, J. H.; Kishi, Y. J. Am. Chem. Soc. 2016, 138, 7178-7186; Thornton, A. R.; Martin, V. I.; Blakey, A. B. J. Am. Chem. Soc. 2009, 131, 2434-2435.

General procedure A

To a stirred solution of alcohol (1.0 equiv.) in $CH_2Cl_2$ (10 mL) at 0° C. were added silyl chloride (1.1 equiv.) and imidazole (1.5 equiv.). The reaction mixture was allowed to room temperature, stirred until starting material was consumed. The reaction mixture was quenched by addition of saturated $NaHCO_3$ (10 mL). The aqueous layer was extracted with $CH_2Cl_2$ (3×10 mL) and the organic extracts were washed with $H_2O$ (2×10 mL) and brine. The washed organic layers were dried over $Na_2SO_4$, filtered, concentrated, and purified by a silica gel column chromatography to yield pure product.

General procedure B

To a stirred solution of alcohol (1.0 equiv.) in $CH_2Cl_2$ (10 mL) at 0° C. were added $PPh_3$ (1.1 equiv.), imidazole (1.2 equiv.) and iodine (1.1 equiv.). The reaction mixture was stirred at room temperature until the disappearance of starting material on TLC plate. The reaction was quenched by addition of aqueous hypo solution (10 mL) and stirred for 30 min. The organic layer was separated and the aqueous phase was extracted with $CH_2Cl_2$ (2×10 mL). The combined organics were dried, concentrated and purified by a silica gel column chromatography to afford pure alkyl iodide.

Synthesis of Substrates: Alkyl Halides

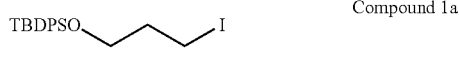
Compound 1a 1a was prepared from 3-iodo-propan-1-ol, according to general procedure A. 1H NMR (500 MHz, Benzene-d$_6$) δ 7.73-7.65 (m, 4H), 7.23-7.18 (m, 6H), 3.48 (t, J=5.7 Hz, 2H), 2.94 (t, J=6.8 Hz, 2H), 1.68-1.58 (m, 2H), 1.10 (s, 9H); $^{13}$C NMR (125 MHz, Benzene-d$_6$) δ 135.6, 133.6, 129.7, 127.7, 63.0, 35.9, 26.7, 26.7, 19.1, 2.7; IR (neat) v 2929, 2856, 1426, 1104, 822, 686, 488; HRMS (ESI) calcd. for C$_{19}$H$_{25}$INaOSi [M+Na]$^+$: 460.0612, found 447.0600.

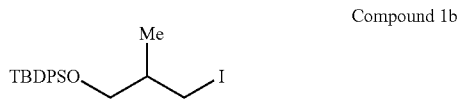
Compound 1b 1a was prepared from 3-iodo-2-methylpropan-1-ol (See, e.g., Fleming, F. F.; Gudipati, S.; Vu, V. A.; Mycka, R. J.; Knochel, P. *Org. Lett.* 2007, 9, 4507-4509), according to general procedure A. 1H NMR (500 MHz, Benzene-d$_6$): δ 7.76-7.68 (m, 4H), 7.24-7.18 (m, 6H), 3.43 (dd, J=10.1, 5.1 Hz, 1H), 3.36 (dd, J=10.1, 6.7 Hz, 1H), 3.06-3.00 (m, 2H), 1.42-1.35 (m, 1H), 1.11 (s, 9H), 0.68 (d, J=6.7 Hz, 3H); $^{13}$C NMR (125 MHz, Benzene-d$_6$) δ 135.7, 135.6, 133.6, 133.5, 129.7, 129.7, 127.7, 67.2, 37.3, 26.7, 19.1, 16.8, 12.8; IR (neat) v 2958, 2929, 2856, 1426, 1104, 848, 698, 484; HRMS (ESI) calcd. for C$_{20}$H$_{28}$IOSi [M+H]$^+$: 439.0949, found 439.0932.

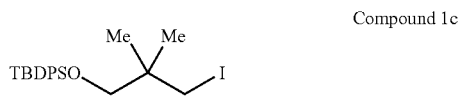
Compound 1c 1c was prepared from 2,2-dimethyl-butane-1,3-diol, according to general procedure A followed by general procedure B. 1H NMR (500 MHz, Benzene-d$_6$) δ 7.79-7.71 (m, 4H), 7.27-7.17 (m, 6H), 3.35 (s, 2H), 3.06 (s, 2H), 1.13 (s, 9H), 0.80 (s, 6H); $^{13}$C NMR (125 MHz, Benzene-d$_6$) δ 135.8, 133.4, 129.7, 127.7, 70.3, 35.8, 26.8, 23.6, 20.0, 19.2; IR (neat) v 2958, 2929, 2856, 1427, 1105, 823, 699, 503, 487; HRMS (ESI) calcd. for C$_{21}$H$_{30}$IOSi [M+H]$^+$: 453.1105, found 453.1127.

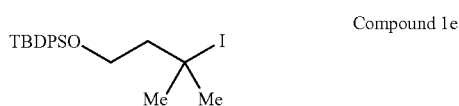
Compound 1e 1e was prepared from 3-iodo-3-methylbutan-1-ol (See, e.g., Turhanen, P. A.; Vepsalainen, J. J. *RSC Adv.* 2015, 5, 26218-26222), according to general procedure A. 1H NMR (500 MHz, Benzene-d$_6$) δ 7.79-7.72 (m, 4H), 7.24-7.19 (m, 6H), 3.90 (t, J=6.6 Hz, 2H), 1.81 (t, J=6.7 Hz, 2H), 1.64 (s, 6H), 1.14 (s, 9H); $^{13}$C NMR (125 MHz, Benzene-d$_6$) δ 135.6, 133.6, 129.7, 127.8, 64.3, 51.9, 47.6, 38.3, 26.7, 19.0; IR (neat) v 2954, 2930, 2854, 1428, 1107, 824, 701, 502, 485; HRMS (ESI) calcd. for C$_{21}$H$_{30}$IOSi [M+H]$^+$: 453.1105, found 453.1122.

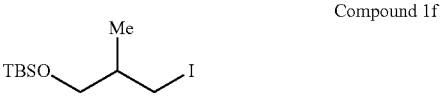 [SMILES: CC(CI)CO[Si](C)(C)C(C)(C)C]
Compound 1f 1f was prepared from 3-iodo-2-methylpropan-1-ol, according to general procedure A. $^1$H NMR (500 MHz, Benzene-d$_6$) δ 3.29 (dd, J=9.9, 5.0 Hz, 1H), 3.21 (dd, J=9.9, 6.7 Hz, 1H), 3.02-2.94 (m, 2H), 1.36-1.27 (m, 1H), 0.91 (s, 9H), 0.71 (d, J=6.7 Hz, 3H), 0.01 (s, 3H), −0.00 (s, 3H); $^{13}$C NMR (125 MHz, Benzene-d$_6$) δ 66.4, 37.1, 25.7, 18.1, 16.8, 13.0, −5.6; IR (neat) v 2954, 2928, 2856, 1470, 1250, 1097, 833, 773; HRMS (ESI) calcd. for C$_{10}$H$_{23}$INaOSi [M+Na]$^+$: 337.0455, found 337.0450.

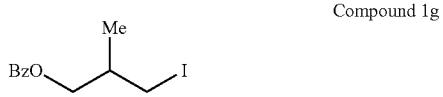
Compound 1g

Benzoyl chloride (1.2 equiv.) was added to a stirred solution of 3-iodo-2-methylpropan-1-ol (1.0 equiv.) and Et$_3$N (2.0 equiv.) in CH$_2$Cl$_2$ (10 mL) at 0° C. After being stirred at 0° C. for 1 h and at room temperature for 6 h, the reaction mixture was poured into water. The aqueous layer was extracted with CH$_2$Cl$_2$ (2×10 mL), and the combined organic layers were dried over Na$_2$SO$_4$ and evaporated. Purification of the crude product by silica gel column chromatography gave the title compound 1g in 95% yield. $^1$H NMR (500 MHz, Benzene-d$_6$) δ 8.08-8.03 (m, 2H), 7.12-7.06 (m, 1H), 7.05-6.98 (m, 2H), 3.98 (dd, J=11.0, 5.7 Hz, 1H), 3.90 (dd, J=11.1, 6.9 Hz, 1H), 2.76 (dd, J=9.9, 5.0 Hz, 1H), 2.71 (dd, J=10.0, 6.1 Hz, 1H), 1.50-1.41 (m, 1H), 0.65 (d, J=6.7 Hz, 3H); $^{13}$C NMR (125 MHz, Benzene-d$_6$) δ 165.5, 132.6, 130.4, 129.5, 128.2, 67.8, 34.2, 17.0, 11.1; IR (neat) v 2964, 2887, 1715, 1450, 1266, 1108, 706; HRMS (ESI) calcd. for C$_{11}$H$_{13}$INaO$_2$ [M+Na]: 326.9852, found 326.9851.

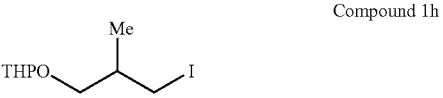
Compound 1h

A solution of 3-iodo-2-methylpropan-1-ol (1.0 equiv.) in anhydrous CH$_2$Cl$_2$ (10 mL) was charged with 3,4-dihydro-2H-pyrane (2.0 equiv.) and PTSA (10 mol %) at 0° C. and then stirred for 2 h at room temperature. The reaction mixture was then washed with aqueous NaHCO$_3$ solution (10 mL) and water (3×30 mL). The combined organic phases were dried with Na$_2$SO$_4$ and concentrated in vacuum gave THP product 1h as a 1:1 mixture of diastereomers. 1H NMR (500 MHz, Benzene-d$_6$) δ 4.49-4.42 (m, 1H), 3.78-3.65 (m, 1H), 3.55 (dd, J=9.7, 5.4 Hz, 0.5H), 3.50 (dd, J=9.7, 7.1 Hz, 0.5H), 3.41-3.30 (m, 1H), 3.07-2.95 (m, 3H), 1.69-1.57 (m, 1H), 1.52-1.44 (m, 3H), 1.40-1.26 (m, 1H), 1.25-1.16 (m, 2H), 0.77 (d, J=6.7 Hz, 1.5H), 0.75 (d, J=6.7 Hz, 1.5H); $^{13}$C NMR (125 MHz, Benzene-d$_6$) 6 (98.6, 98.0) (THP), (71.0, 70.6) (—CH$_2$—O), (61.4, 61.2) (THP), (35.2, 35.1) (—CH—) (—CH—CH$_3$), (30.5, 30.5) (THP), (25.5, 25.5)

(THP), (19.3, 19.1) (THP), (17.4, 17.2) (—CH—CH$_3$), (13.4, 13.1) (—CH$_2$—I); IR (neat) v 2939, 2868, 1453, 1199, 1031, 884, 869; HRMS (ESI) calcd. for C$_9$H$_{17}$INaO$_2$ [M+Na]$^+$: 307.0165, found 307.0164.

Compound 1i

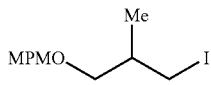

Pyridinium p-toluenesulfonate (10 mol %) was added to a solution of 3-iodo-2-methylpropan-1-ol (1.0 equiv.) and 4-methoxybenzoyl trichloroacetimidate (1.2 equiv.) in CH$_2$Cl$_2$ (10 mL). The mixture was stirred overnight before the reaction was quenched with saturated aqueous NaHCO$_3$ solution. The aqueous phase was extracted with CH$_2$Cl$_2$ (2×10 mL) and the combined organic extracts were dried over Na$_2$SO$_4$ and evaporated. The residue was purified by flash chromatography to give product 1i as a colorless oil. $^1$H NMR (500 MHz, Benzene-d$_6$) δ 7.17-7.13 (m, 2H), 6.80-6.76 (m, 2H), 4.22 (s, 2H), 3.28 (s, 3H), 3.09-3.02 (m, 2H), 3.02-2.96 (m, 2H), 1.49-1.40 (m, 1H), 0.73 (d, J=6.7 Hz, 3H); $^{13}$C NMR (125 MHz, Benzene-d$_6$) δ 159.4, 130.6, 129.1, 113.7, 73.4, 72.6, 54.5, 35.1, 17.3, 13.5; IR (neat) v 2958, 2855, 1611, 1510, 1243, 1086, 1033, 816, 579; HRMS (ESI) calcd. for C$_{12}$H$_{17}$INaO$_2$ [M+Na]$^+$: 343.0165, found 343.0168.

Compound 1j

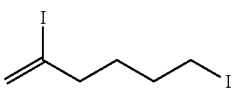

1j was prepared from 5-iodohex-5-en-1-ol (See, e.g., Johannes, J. W.; Wenglowsky, S.; Kishi, Y. *Org. Lett.* 2005, 7, 3997-4000), using general procedure B. $^1$H NMR (500 MHz, Benzene-d$_6$) δ 5.52-5.49 (m, 1H), 5.45 (s, 1H), 2.56-2.50 (m, 2H), 1.87 (td, J=7.0, 1.3 Hz, 2H), 1.28-1.13 (m, 4H); $^{13}$C NMR (125 MHz, Benzene-d$_6$) 125.4, 111.4, 43.7, 31.6, 29.5, 5.3; IR (neat) v 2934, 2832, 1614, 1425, 1165, 1154, 890, 723, 492; HRMS (ESI) calcd. for C$_6$H$_{11}$I$_2$ [M+H]$^+$: 336.8944, found 336.8938.

Compound 1k

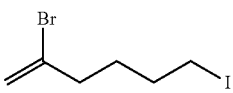

1k was prepared from 5-bromohex-5-en-1-ol (See, e.g., Ruscoe, R. E.; Fazakerley, N. J.; Huang, H.; Flitsch, S.; Procter, D. J. *Chem. Eur. J.* 2016, 22, 116-119), using general procedure B. 1H NMR (600 MHz, Benzene-d$_6$) δ 5.15 (d, J=1.6 Hz, 1H), 5.05-5.03 (m, 1H), 2.52 (t, J=6.7 Hz, 2H), 1.89 (t, J=7.3 Hz, 2H), 1.29-1.15 (m, 4H); $^{13}$C NMR (150 MHz, Benzene-d$_6$) δ 136.5, 119.1, 42.5, 34.5, 31.0, 7.9; IR (neat) v 2938, 2859, 1627, 1426, 1212, 1167, 885, 737, 518; HRMS (ESI) calcd. for C$_6$H$_{10}$IBrNa [M+Na]$^+$: 310.8903, found 310.8895.

Compound 1l

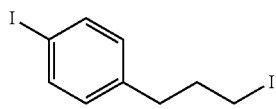

1l was prepared from 3-(4-iodophenyl)propan-1-ol (See, e.g., Miyajima, D.; Araoka, F.; Takezoe, H.; Kim, J.; Kato, K.; Takata, M.; Aida, T. *Angew. Chem., Int. Ed.* 2011, 50, 7865-7869), using general procedure B. $^1$H NMR (500 MHz, Benzene-d$_6$) δ 7.37 (d, J=8.3 Hz, 2H), 6.41 (d, J=8.5 Hz, 2H), 2.56 (t, J=6.8 Hz, 2H), 2.12 (d, J=7.2 Hz, 2H), 1.56-1.47 (m, 2H); $^{13}$C NMR (125 MHz, Benzene-d$_6$) δ 139.7, 137.4, 130.4, 91.3, 35.3, 34.3, 5.5; IR (neat) v 2934, 1483, 1398, 1209, 1005, 830, 507, 495; HRMS (ESI) calcd. for C$_9$H$_{11}$I$_2$[M+H]$^+$: 372.8945, found 372.8938.

Compound 1q

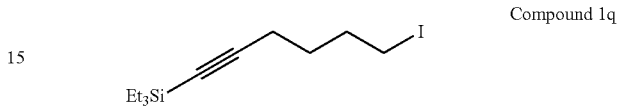

1l was prepared from 6-(triethylsilyl)hex-5-yn-1-ol, using general procedure A. $^1$H NMR (500 MHz, Benzene-d$_6$) δ 2.60 (t, J=7.0 Hz, 2H), 1.85 (t, J=6.9 Hz, 2H), 1.51 (p, J=7.1 Hz, 2H), 1.20 (p, J=7.1 Hz, 2H), 1.08 (t, J=7.9 Hz, 9H), 0.62 (q, J=7.9 Hz, 6H); $^{13}$C NMR (125 MHz, Benzene-d$_6$) δ 107.6, 82.0, 32.3, 29.1, 18.6, 7.5, 5.2, 4.6; IR (neat) v 2952, 2910, 2872, 2171, 1457, 1210, 1017, 687; HRMS (ESI) calcd. for C$_{12}$H$_{24}$ISi [M+H]$^+$: 323.0687, found 323.0680.

General Procedures for Ketone Synthesis

Method A

To alkyl iodide 1a~q (1.0 equiv.), acid chloride 2a (3.0 equiv.) in 1,2-dimethoxyethane (C 0.4 M) were added manganese (2.0 equiv.), copper (II) chloride (1.0 equiv.), lithium chloride (3.0 equiv.) and Iron (III) tris(2,2,6,6-tetramethyl-3,5-heptanedionate) 4 (10 mol %). The reaction mixture was cooled to 0° C. and stirred vigorously for 15 h at the same temperature. Upon completion of reaction, florosil was added and stirred for 30 min at 0° C. and filtered through a pad of Celite, washed with ethyl acetate (10 mL) and the filtrate was dried over anhydrous Na$_2$SO$_4$, filtered and concentrated under rotary evaporator. After concentration, purification through a silica gel column chromatography yields the desired ketone 3 a~q.

Method B-1

To alkyl iodide 1a~q (1.2 equiv.), acid chloride 2a (1.0 equiv.) in 1,2-dimethoxyethane (C 0.4 M) were added manganese (2.0 equiv.), copper (II) chloride (1.0 equiv.), lithium chloride (3.0 equiv.) and FeBr$_2$(dppb) 5a (5 mol %). The reaction mixture was cooled to 0° C. and stirred vigorously for 15 h at the same temperature. Upon completion of reaction, florosil was added and stirred for 30 min at 0° C. and filtered through a pad of Celite, washed with ethyl acetate (10 mL) and the filtrate was dried over anhydrous Na$_2$SO$_4$, filtered and concentrated under rotary evaporator. After concentration, purification through a basic alumina column chromatography yields the desired ketone 3 a~q.

Method B-2

To alkyl iodide 1a~q (1.0 equiv.), acid chloride 2a (1.2 equiv.) in 1,2-dimethoxyethane (C 0.4 M) were added manganese (2.0 equiv.), copper (II) chloride (1.0 equiv.), lithium chloride (3.0 equiv.) and FeBr$_2$(dppb) 5a (5 mol %). The reaction mixture was cooled to 0° C. and stirred vigorously for 15 h at the same temperature. Upon completion of reaction, florosil was added and stirred for 30 min at 0° C. and filtered through a pad of Celite, washed with ethyl acetate (10 mL) and the filtrate was dried over anhydrous Na$_2$SO$_4$, filtered and concentrated under rotary evaporator. After concentration, purification through a silica gel column chromatography yields the desired ketone 3 a~q.

Method C

To alkyl iodide 1a~q (1.0 equiv.), thioester 2b (1.2 equiv.) in 1,2-dimethoxyethane (C 0.4 M) were added manganese (2.0 equiv.), copper (I) iodide (1.0 equiv.), lithium chloride (3.0 equiv.), Cp$_2$ZrCl$_2$ (1.0 equiv.) and FeBr$_2$(dppb) 5a (5 mol %). The reaction mixture was cooled to 0° C. and stirred vigorously for 15 h at the same temperature. Upon completion of reaction, florosil was added and stirred for 30 min at 0° C. and filtered through a pad of Celite, washed with ethyl acetate (10 mL) and the filtrate was dried over anhydrous Na$_2$SO$_4$, filtered and concentrated under rotary evaporator. After concentration, purification through a silica gel column chromatography yields the desired ketone 3 a~q.

Compound 3a

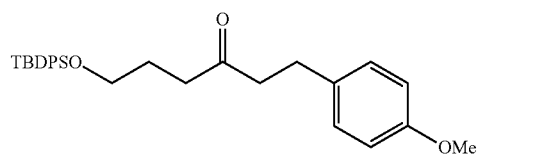

Yield: 76% (Method A), 90% (Method B-1), 87% (Method B-2), 80% (Method C); $^1$H NMR (600 MHz, Benzene-d$_6$) δ 7.73-7.68 (m, 4H), 7.22-7.17 (m, 6H), 6.94-6.90 (m, 2H), 6.74-6.70 (m, 2H), 3.54 (t, J=6.2 Hz, 2H), 3.29 (s, 3H), 2.74 (t, J=7.5 Hz, 2H), 2.24 (td, J=7.6, 1.2 Hz, 2H), 2.08-2.03 (m, 2H), 1.78-1.72 (m, 2H), 1.12 (s, 9H); IR (neat) v 2953, 2930, 1712, 1511, 1244, 1105, 1035, 822, 700, 503; HRMS (ESI) calcd. for C$_{29}$H$_{37}$O$_3$Si [M+H]$^+$: 461.2506, found 461.2508. See, e.g., Lee, J. H.; Kishi, Y. *J. Am. Chem. Soc.* 2016, 138, 7178-7186.

Compound 3b

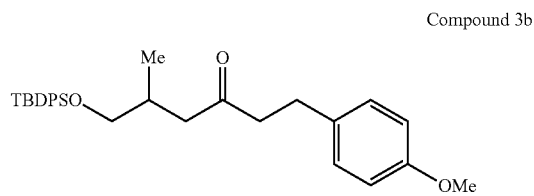

Yield: 74% (Method A), 86% (Method B-1), 83% (Method B-2), 78% (Method C); $^1$H NMR (500 MHz, Benzene-d$_6$) δ 7.76-7.72 (m, 4H), 7.24-7.19 (m, 6H), 6.95 (d, J=8.6 Hz, 2H), 6.75 (d, J=8.6 Hz, 2H), 3.48-3.39 (m, 2H), 3.30 (s, 3H), 2.81-2.75 (m, 2H), 2.36-2.23 (m, 4H), 1.88-1.79 (m, 1H), 1.14 (s, 9H), 0.83 (d, J=6.7 Hz, 3H); IR (neat) v 2956, 2930, 1711, 1512, 1245, 1110, 1036, 823, 701, 504; HRMS (ESI) calcd. for C$_{30}$H$_{39}$O$_3$Si [M+H]$^+$: 475.2663, found 475.2675. Lee, J. H.; Kishi, Y. *J. Am. Chem. Soc.* 2016, 138, 7178-7186.

Compound 3c

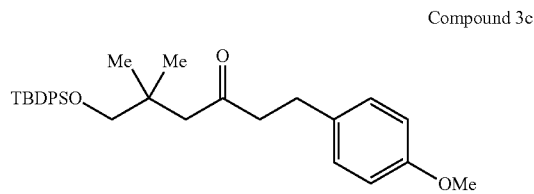

Yield: 72% (Method A), 80% (Method B-1), 80% (Method B-2), 72% (Method C); $^1$H NMR (600 MHz, Benzene-d$_6$) δ 7.76-7.70 (m, 4H), 7.24-7.16 (m, 6H), 6.97-6.90 (m, 2H), 6.75-6.71 (m, 2H), 3.47 (s, 2H), 3.28 (s, 3H), 2.77 (t, J=7.5 Hz, 2H), 2.34 (t, J=7.0 Hz, 2H), 2.15 (s, 2H), 1.13 (s, 9H), 0.94 (s, 6H); IR (neat) v 2955, 2930, 2587, 1712, 1512, 1246, 1111, 1037, 824, 701; HRMS (ESI) calcd. for C$_{31}$H$_{41}$O$_3$Si [M+H]$^+$: 489.2819, found 489.2842. Lee, J. H.; Kishi, Y. *J. Am. Chem. Soc.* 2016, 138, 7178-7186.

Compound 3d

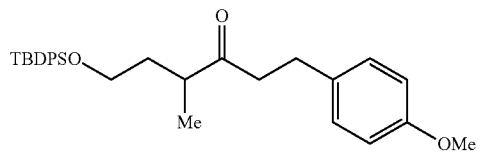

Yield: 74% (Method A), 80% (Method B-1), 80% (Method B-2), 74% (Method C); 1H NMR (500 MHz, Benzene-d$_6$) δ 7.72-7.67 (m, 4H), 7.22-7.16 (m, 6H), 6.97-6.93 (m, 2H), 6.75-6.70 (m, 2H), 3.59-3.50 (m, 2H), 3.28 (s, 3H), 2.81 (t, J=7.4 Hz, 2H), 2.48 (q, J=6.9 Hz, 1H), 2.45-2.41 (m, 2H), 1.95-1.86 (m, 1H), 1.38-1.31 (m, 1H), 1.11 (s, 9H), 0.80 (d, J=7.0 Hz, 3H); IR (neat) v 2956, 2930, 1709, 1512, 1245, 1109, 822, 701, 503; HRMS (ESI) calcd. for C$_{30}$H$_{39}$O$_3$Si [M+H]$^+$: 475.2663, found 475.2680. Lee, J. H.; Kishi, Y. *J. Am. Chem. Soc.* 2016, 138, 7178-7186.

Compound 3f

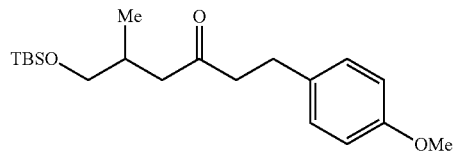

Yield: 78% (Method A), 90% (Method B-1), 86% (Method B-2), 81% (Method C); $^1$H NMR (500 MHz, Benzene-d$_6$) δ 6.97-6.93 (m, 2H), 6.76-6.73 (m, 2H), 3.33 (dd, J=9.7, 5.4, 1H), 3.31 (s, 3H), 3.25 (dd, J=9.7, 6.0, 1H), 2.79 (t, J=7.5 Hz, 2H), 2.40-2.24 (m, 3H), 2.24-2.16 (m, 1H), 1.88-1.85 (dd, J=15.8, 7.0, 1H), 0.93 (d, J=0.8 Hz, 9H), 0.82 (d, J=6.7 Hz, 3H), 0.01 (s, 3H), 0.00 (s, 3H); $^{13}$C NMR (125 MHz, Benzene-d$_6$) δ 207.4, 158.2, 133.3, 129.2, 113.8, 67.4, 54.4, 46.2, 44.7, 31.7, 28.9, 25.8, 18.1, 16.6, −5.7; HRMS (ESI) calcd. for C$_{20}$H$_{34}$NaO$_3$Si [M+Na]$^+$: 373.2169, found 373.2169.

Compound 3g

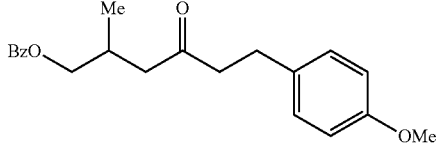

Yield: 81% (Method A), 90% (Method B-1), 90% (Method B-2), 90% (Method C); $^1$H NMR (500 MHz, Benzene-d$_6$) δ 8.14-8.09 (m, 2H), 7.11-7.01 (m, 3H), 6.93 (d, J=8.6 Hz, 2H), 6.77-6.71 (m, 2H), 4.03 (dd, J=10.8, 6.0 Hz, 1H), 3.96 (dd, J=10.8, 6.4 Hz, 1H), 3.29 (s, 3H), 2.82-2.68 (m, 2H), 2.44-2.33 (m, 1H), 2.28-2.15 (m, 2H), 2.02 (dd, J=16.9, 5.8 Hz, 1H), 1.74 (dd, J=16.9, 7.6 Hz, 1H), 0.76 (d, J=6.8 Hz, 3H); IR (neat) v 2958, 2935, 1711, 1511, 1270, 1109, 828, 710, 544, 519; HRMS (ESI) calcd. for C$_{21}$H$_{24}$NaO$_4$ [M+Na]+: 363.1567, found 363.1575. Lee, J. H.; Kishi, Y. *J. Am. Chem. Soc.* 2016, 138, 7178-7186.

Compound 3h

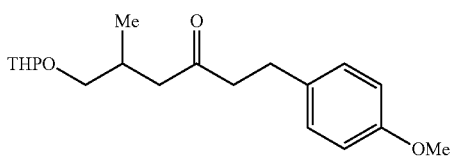

Yield: 75% (Method A), 85% (Method B-1), 84% (Method B-2), 80% (Method C); $^1$H NMR (500 MHz, Benzene-d$_6$) δ 6.99-6.94 (m, 2H), 6.78-6.72 (m, 2H), 4.50-4.45 (m, 1H), 3.77-3.69 (m, 1H), 3.60 (dd, J=9.4, 5.9 Hz, 0.5H), 3.51 (dd, J=9.4, 6.9 Hz, 0.5H), 3.39-3.32 (m, 1H), 3.30 (s, 3H), 3.12 (dd, J=9.4, 5.3 Hz, 0.5H), 3.04 (dd, J=9.3, 6.5 Hz, 0.5H), 2.84-2.77 (m, 2H), 2.41-2.29 (m, 4.5H), 2.25 (dd, J=16.3, 6.1 Hz, 0.5H), 1.90 (dd, J=7.3, 3.0 Hz, 0.5H), 1.87 (dd, J=7.3, 3.3 Hz, 0.5H), 1.73-1.62 (m, 1H), 1.57-1.50 (m, 2H), 1.37-1.28 (m, 1H), 1.28-1.17 (m, 1H), 0.86 (d, J=6.8 Hz, 1.5H), 0.84 (d, J=6.6 Hz, 1.5H); $^{13}$C NMR (125 MHz, Benzene-d$_6$) δ (207.35, 207.27) (—C=O), 158.23 (MPM-CH—), 133.37 (MPM-CH—), 129.26 (MPM-CH—), 113.84 (MPM-CH—), (98.55, 98.27), (71.88, 71.67), (61.44, 61.41), 54.40, 46.88, (44.69, 44.64), 30.60, (29.76, 29.64), 28.89, 25.54, (19.41, 19.37), (17.09, 17.02); IR (neat) v 2937, 2872, 1710, 1512, 1244, 1177, 1032, 904, 545, 521; HRMS (ESI) calcd. for C$_{19}$H$_{28}$NaO$_4$ [M+Na]$^+$: 343.1880, found 343.1892.

Compound 3i

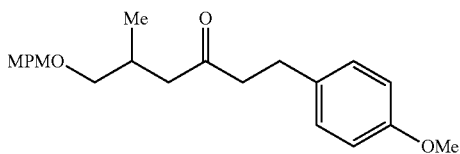

Yield: 71% (Method A), 78% (Method B-1), 74% (Method B-2), 70% (Method C); $^1$H NMR (600 MHz, Benzene-d$_6$) δ 7.16 (dd, J=7.5, 1.3 Hz, 2H), 6.94-6.90 (m, 2H), 6.79-6.75 (m, 2H), 6.74-6.70 (m, 2H), 4.22 (m, 2H), 3.28 (s, 3H), 3.26 (s, 3H), 3.12 (dd, J=9.0, 5.3 Hz, 1H), 3.03 (dd, J=9.0, 6.7 Hz, 1H), 2.76 (t, J=7.5 Hz, 2H), 2.39-2.32 (m, 2H), 2.32-2.25 (m, 2H), 1.86 (dd, J=16.3, 7.2 Hz, 1H), 0.82 (d, J=6.7 Hz, 3H); IR (neat) v 2954, 2932, 1710, 1512, 1245, 11177, 1034, 819; HRMS (ESI) calcd. for C$_{22}$H$_{27}$O$_3$[M+H—H$_2$O]$^+$: 339.1955, found 339.1969. Lee, J. H.; Kishi, Y. J. Am. Chem. Soc. 2016, 138, 7178-7186.

Compound 3j

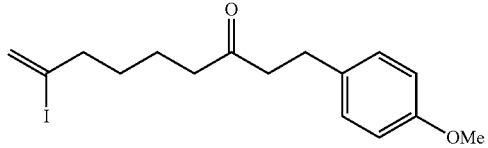

Yield: 76% (Method A), 86% (Method B-1), 83% (Method B-2), 79% (Method C); $^1$H NMR (500 MHz, Benzene-d$_6$) δ 6.96 (d, J=8.5 Hz, 2H), 6.76 (d, J=8.6 Hz, 2H), 5.62-5.60 (m, 1H), 5.50 (s, 1H), 3.31 (s, 3H), 2.76 (t, J=7.5 Hz, 2H), 2.21 (t, J=7.4 Hz, 2H), 2.03 (td, J=7.1, 1.3 Hz, 2H), 1.78 (t, J=7.2 Hz, 2H), 1.34-1.26 (m, 2H), 1.25-1.17 (m, 2H); $^{13}$C NMR (125 MHz, Benzene-d$_6$) δ207.3, 158.3, 133.2, 129.3, 125.2, 113.9, 112.1, 54.4, 44.9, 44.1, 42.0, 29.0, 28.5, 22.0; IR (neat) v 2932, 2859, 2833, 1710, 1611, 1510, 1242, 1176, 1033, 824, 542; HRMS (ESI) calcd. for C$_{16}$H$_{21}$INaO$_2$ [M+Na]$^+$: 395.0478, found 395.0468.

Compound 3k

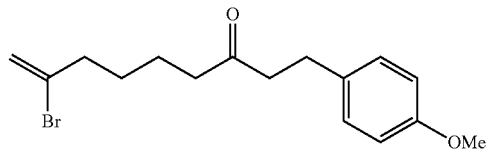

Yield: 74% (Method A), 85% (Method B-1), 83% (Method B-2), 80% (Method C); $^1$H NMR (500 MHz, Benzene-d$_6$) δ 6.98-6.94 (m, 2H), 6.78-6.74 (m, 2H), 5.23 (d, J=1.6 Hz, 1H), 5.18-5.16 (m, 1H), 3.31 (s, 3H), 2.76 (t, J=7.4 Hz, 2H), 2.22 (t, J=7.5 Hz, 2H), 2.07 (td, J=7.1, 1.1 Hz, 2H), 1.79 (t, J=7.0 Hz, 2H), 1.36-1.23 (m, 4H); $^{13}$C NMR (125 MHz, Benzene-d$_6$) δ 207.3, 158.3, 134.3, 133.2, 129.3, 116.3, 113.9, 54.4, 44.1, 41.9, 41.0, 28.9, 27.3, 22.2; IR (neat) v 2937, 2834, 1712, 1512, 1245, 1178, 1035, 826; HRMS (ESI) calcd. for C$_{16}$H$_{21}$BrNaO$_2$ [M+Na]$^+$: 347.0617, found 347.0615.

Compound 3l

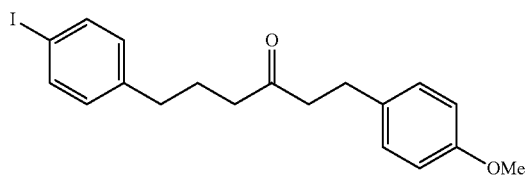

Yield: 75% (Method A), 86% (Method B-1), 86% (Method B-2), 81% (Method C); $^1$H NMR (500 MHz, Benzene-d$_6$) δ 7.42 (d, J=8.0 Hz, 2H), 6.95 (d, J=8.1 Hz, 2H), 6.75 (d, J=8.4 Hz, 2H), 6.48 (d, J=8.1 Hz, 2H), 3.31 (s, 3H), 2.75 (t, J=7.4 Hz, 2H), 2.19 (t, J=7.4 Hz, 2H), 2.14 (t, J=7.6 Hz, 2H), 1.79 (t, J=7.2 Hz, 2H), 1.64-1.55 (m, 2H); $^{13}$C NMR (125 MHz, Benzene-d$_6$) δ207.3, 158.3, 141.2, 137.3, 133.2, 130.4, 129.3, 113.9, 90.9, 54.4, 44.1, 41.3, 34.2, 28.9, 24.7; IR (neat) v 2940, 2865, 1701, 1510, 1240, 1178, 1028, 1006, 816, 794, 508; HRMS (ESI) calcd. for C$_{19}$H$_{22}$IO$_2$ [M+H]$^+$: 409.0659, found 409.0662.

Compound 3m

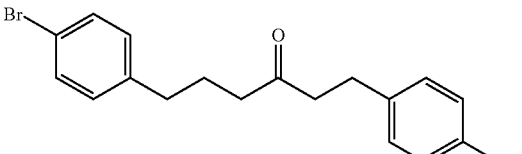

Yield: 74% (Method A), 87% (Method B-1), 84% (Method B-2), 80% (Method C); 1H NMR (500 MHz, Benzene-d$_6$) δ 7.24-7.20 (m, 2H), 6.97-6.93 (m, 2H), 6.77-6.73 (m, 2H), 6.61-6.57 (m, 2H), 3.30 (s, 3H), 2.75 (t, J=7.4 Hz, 2H), 2.19 (t, J=7.4 Hz, 2H), 2.17-2.13 (m, 2H), 1.79 (t, J=7.2 Hz, 2H), 1.63-1.56 (m, 2H); $^{13}$C NMR (125 MHz, Benzene-d$_6$) δ 207.3, 158.3, 140.6, 133.2, 131.3, 130.1, 129.3, 119.6, 113.9, 54.4, 44.1, 41.3, 34.1, 28.9, 24.7; IR (neat) v 2933, 2834, 1709, 1511, 1242, 1176, 1033, 818, 513; HRMS (ESI) calcd. for C$_{19}$H$_{21}$BrNaO$_2$ [M+Na]$^+$: 383.0617, found 383.0609.

Compound 3n

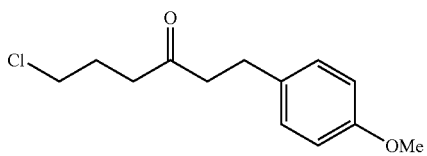

Yield: 72% (Method A), 76% (Method B-1), 74% (Method B-2), 70% (Method C); 1H NMR (500 MHz, Benzene-$d_6$) δ 6.92 (d, J=8.6 Hz, 2H), 6.75 (d, J=8.6 Hz, 2H), 3.30 (s, 3H), 3.07 (t, J=6.3 Hz, 2H), 2.70 (t, J=7.5 Hz, 2H), 2.15 (t, J=7.5 Hz, 2H), 1.90 (t, J=7.0 Hz, 2H), 1.69-1.61 (m, 2H); $^{13}$C NMR (125 MHz, Benzene-$d_6$) δ 206.7, 158.3, 133.0, 129.2, 113.9, 54.4, 44.1, 44.0, 38.9, 28.8, 26.2; IR (neat) ν 2955, 2835, 1712, 1512, 1245, 1178, 1034, 827; HRMS (ESI) calcd. for $C_{13}H_{17}C_1NaO_2$ [M+Na]$^+$: 263.0809, found 263.0813.

Compound 3o

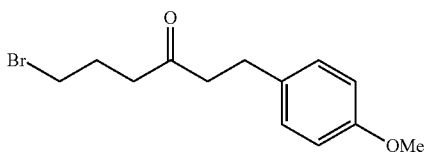

Yield: 15% (Method A), 30% (Method B-1), 25% (Method B-2), 21% (Method C); 1H NMR (500 MHz, Benzene-$d_6$) δ 6.94-6.90 (m, 2H), 6.78-6.73 (m, 2H), 3.30 (s, 3H), 2.92 (t, J=6.4 Hz, 2H), 2.70 (t, J=7.5 Hz, 2H), 2.14 (t, J=7.5 Hz, 2H), 1.89 (t, J=7.0 Hz, 2H), 1.76-1.68 (m, 2H); $^{13}$C NMR (125 MHz, Benzene-$d_6$) δ 206.5, 158.3, 133.0, 129.2, 113.9, 54.4, 44.0, 40.2, 33.1, 28.8, 26.3; IR (neat) ν 2954, 2934, 1711, 1511, 1243, 1177, 1034, 827, 552, 521; HRMS (ESI) calcd. for $C_{13}H_{18}BrO_2$ [M+H]$^+$: 285.0485, found 285.0478.

Compound 3p

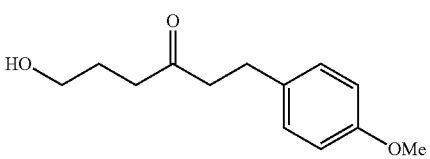

Yield: 25% (Method A), 36% (Method B-1), 35% (Method B-2), 36% (Method C); 1H NMR (500 MHz, Benzene-$d_6$) δ 6.97-6.91 (m, 2H), 6.78-6.72 (m, 2H), 3.33 (dd, J=10.0, 4.2 Hz, 2H), 3.31 (s, 3H), 2.74 (t, J=7.5 Hz, 2H), 2.26 (t, J=7.5 Hz, 2H), 2.03 (t, J=7.0 Hz, 2H), 1.84 (bs, 1H), 1.65-1.57 (m, 2H); $^{13}$C NMR (125 MHz, Benzene-$d_6$) δ 208.9, 158.2, 133.2, 129.3, 113.9, 61.6, 54.4, 44.2, 39.1, 28.9, 26.6; IR (neat) ν 3409, 2933, 2835, 1707, 1511, 1242, 1177, 1056, 826, 542, 520; HRMS (ESI) calcd. for $C_{13}H_{17}O_2$[M+H—$H_2O$]$^+$: 205.1233, found 205.1219.

Compound 3q

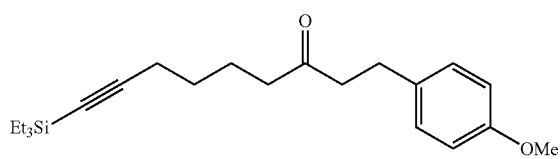

Yield: 75% (Method A), 86% (Method B-1), 82% (Method B-2), 78% (Method C); $^1$H NMR (500 MHz, Benzene-$d_6$) δ 6.95 (d, J=8.7 Hz, 2H), 6.76 (d, J=8.7 Hz, 2H), 3.31 (s, 3H), 2.75 (t, J=7.5 Hz, 2H), 2.21 (t, J=7.5 Hz, 2H), 1.99 (t, J=7.1 Hz, 2H), 1.82 (t, J=7.3 Hz, 2H), 1.56-1.49 (m, 2H), 1.29-1.22 (m, 2H), 1.09 (t, J=7.9 Hz, 9H), 0.64 (q, J=7.9 Hz, 6H); $^{13}$C NMR (125 MHz, Benzene-$d_6$) δ 207.2, 158.3, 133.3, 129.2, 113.9, 108.3, 81.7, 54.4, 44.0, 41.7, 28.9, 28.1, 22.6, 19.6, 7.5, 4.7; IR (neat) ν 2951, 2910, 2170, 1713, 1512, 1244, 1035, 825, 723; HRMS (ESI) calcd. for $C_{22}H_{34}NaO_2Si$ [M+Na]$^+$: 381.2220, found 381.2208.

Compound 15

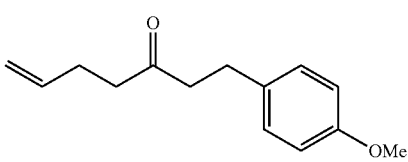

Yield: 72% (Method A), 75% (Method B-1), 70% (Method C); $^1$H NMR (400 MHz, Benzene-$d_6$) δ 6.99-6.89 (m, 2H), 6.78-6.69 (m, 2H), 5.63 (ddt, J=16.9, 10.3, 6.6 Hz, 1H), 4.94-4.84 (m, 2H), 3.27 (s, 3H), 2.73 (t, Jd=7.5 Hz, 2H), 2.16 (t, J=7.5 Hz, 4H), 1.90 (t, J=7.4 Hz, 2H); $^{13}$C NMR (125 MHz, Benzene-$d_6$) δ 206.7, 158.3, 137.3, 133.2, 129.2, 114.7, 113.9, 54.4, 44.1, 41.5, 28.8, 27.6; HRMS (ESI) calcd. for $C_{14}H_{19}O_2$[M+H]$^+$: 219.1380, found 219.1387.

Compound 17

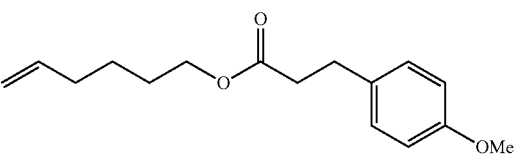

Yield: 75% (Method A), 84% (Method B-1), 79% (Method C); $^1$H NMR (500 MHz, Benzene-$d_6$) δ 6.96-6.92 (m, 2H), 6.74-6.70 (m, 2H), 5.68-5.59 (m, 1H), 4.97-4.90 (m, 2H), 3.93 (t, J=6.6 Hz, 2H), 3.28 (s, 3H), 2.80 (t, J=7.6 Hz, 2H), 2.40 (t, J=7.6 Hz, 2H), 1.81 (dd, d=14.3, 7.3 Hz, 2H), 1.39-1.30 (m, 2H), 1.22-1.12 (m, 2H); $^{13}$C NMR (125 MHz, Benzene-$d_6$) δ 171.9, 158.3, 138.2, 132.6, 129.2, 114.5, 113.8, 63.8, 54.4, 36.0, 33.2, 30.2, 28.1, 25.1; IR (neat) ν 2934, 2859, 1730, 1612, 1512, 1244, 1175, 1035, 823, 544, 520; HRMS (ESI) calcd. for $C_{16}H_{22}NaO_3$ [M+Na]$^+$: 285.1461, found 285.1460.

Compound 19/20

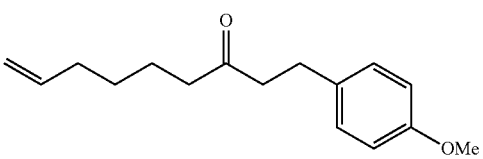

Yield: 78% (Method A), 70% (Method B-1), 78% (Method C); $^1$H NMR (500 MHz, Benzene-$d_6$) δ 7.00-6.93 (m, 2H), 6.79-6.72 (m, 2H), 5.69 (ddt, J=16.9, 10.1, 6.7 Hz, 1H), 5.02-4.90 (m, 2H), 3.30 (s, 3H), 2.77 (t, J=7.5 Hz, 2H), 2.24 (t, J=7.5 Hz, 2H), 1.87 (t, J=7.4 Hz, 2H), 1.42 (dt, J=15.3, 7.3 Hz, 2H), 1.21-1.10 (m, 4H); $^{13}$C NMR (125

MHz, Benzene-d$_6$) δ 207.5, 158.3, 138.4, 133.3, 129.3, 114.4, 113.8, 54.4, 44.1, 42.3, 33.5, 28.9, 28.3, 23.0; IR (neat) ν 2933, 2859, 2835, 1710, 1511, 1243, 1176, 1034, 824, 545, 521; HRMS (ESI) calcd. for C$_{16}$H$_{22}$NaO$_2$ [M+Na]$^+$: 269.1512, found 269.1500.

(R)-2,4-diiodo-3-methylbut-1-ene (7)

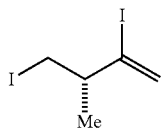

Compound 7 was synthesized, according to the literature procedure (See, e.g., Kim, D.—S.; Dong, C.-G.; Kim, J. T.; Guo, H.; Huang, J.; Tiseni, P. S.; Kishi, Y. *J. Am. Chem. Soc.* 2009, 131, 15636-15641.). MP: 20° C.; [α]$_D^{23}$ −19.2 (c 0.5, CHCl$_3$); 1H NMR (500 MHz, Benzene-d$_6$) δ 5.65-5.59 (m, 1H), 5.51 (dd, J=1.8, 0.6 Hz, 1H), 2.73 (dd, J=10.0, 7.3 Hz, 1H), 2.65 (dd, J=10.0, 6.0 Hz, 1H), 1.71-1.62 (m, 1H), 0.71 (d, J=6.6 Hz, 3H); $^{13}$C NMR (125 MHz, Benzene-d$_6$) δ 126.0, 117.7, 48.2, 20.6, 12.1; IR (neat) ν 2966, 2926, 1607, 1370, 1200, 1166, 896, 783, 614, 541; HRMS (ESI) calcd. for C$_5$H$_8$I$_2$ [M]$^+$: 321.8721, found 321.8715.

(S)-2-bromo-4-iodo-3-methylbut-1-ene (S-1)

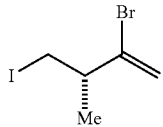

Compound S-1 was synthesized, according to the modified literature procedure (Kim, D.—S.; Dong, C.-G.; Kim, J. T.; Guo, H.; Huang, J.; Tiseni, P. S.; Kishi, Y. *J. Am. Chem. Soc.* 2009, 131, 15636-15641). [α]$_D^{23}$ −17.8 (c 1.3, CHCl$_3$); 1H NMR (500 MHz, Benzene-d$_6$) δ 5.21 (d, J=2.1 Hz, 1H), 5.15-5.13 (m, 1H), 2.83 (dd, J=10.0, 7.1 Hz, 1H), 2.74 (dd, J=10.0, 6.0 Hz, 1H), 2.12-2.04 (m, 1H), 0.78 (d, J=6.6 Hz, 3H); $^{13}$C NMR (125 MHz, Benzene-d$_6$) δ 137.28, 117.25, 45.98, 19.36, 10.45; IR (neat) ν 2971, 2926, 1622, 1372, 1205, 1172, 892, 788, 564; HRMS (ESI) calcd. for C$_5$H$_8$IBr [M]$^+$: 273.8849, found 273.7850.

(R)-ethyl 7-iodo-6-methyl-4-oxooct-7-enoate (8a)

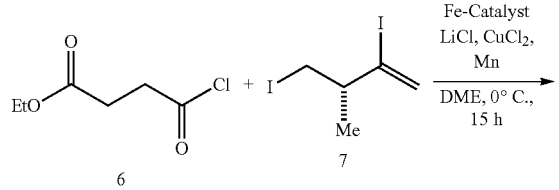

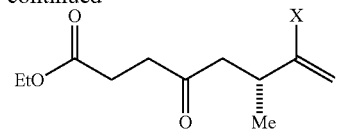

8a: X = I
8b: X = H

Fe(TMHD)$_3$ as a Catalyst:

An oven dried 500 mL single-necked flask equipped with a Teflon-coated egg shaped magnetic stirring bar was charged with Iron(III) tris(2,2,6,6-tetramethyl-3,5-heptanedionate) 4 (4.23 g, 6.99 mmol), manganese (5.11 g, 93.2 mmol), copper(II) chloride (6.26 g, 46.6 mmol), lithium chloride (5.91 g, 139.8 mmol) and 1,2-dimethoxyethane (50 mL) at room temperature. A solution of (R)-2,4-diiodo-3-methylbut-1-ene (7) (15.0 g, 46.6 mmol) in 1,2-dimethoxyethane (66 mL) was charged into the above single-necked flask and added ethyl 4-chloro-4-oxobutanoate (6) (22.93 g, 139.8 mmol) into the reaction mixture. The reaction mixture was cooled to 0° C. and stirred the reaction mixture under nitrogen atmosphere for 15 hours. After completing the reaction florisil (30 g) was added to the reaction mixture and stirred for 30 min at 0° C. Filtered the reaction mixture through Celite, washed the filter cake with ethyl acetate (100 mL) and concentrated under reduced pressure to afford the crude product which was then purified by flash column chromatography on basic alumina using EtOAc/hexanes to afford 11.32 g of (R)-ethyl 7-iodo-6-methyl-4-oxooct-7-enoate (8a) in 75% yield as a colorless liquid. [α]$_D^{23}$ −14.8 (c 1.0, CHCl$_3$); 1H NMR (500 MHz, Benzene-d$_6$) δ 5.81-5.74 (m, 1H), 5.49 (d, J=1.7 Hz, 1H), 3.89 (q, J=7.1 Hz, 2H), 2.47-2.36 (m, 1H), 2.36-2.29 (m, 1H), 2.29-2.21 (m, 2H), 2.20-2.09 (m, 2H), 1.92 (dd, J=16.8, 7.2 Hz, 1H), 0.91 (t, J=7.1 Hz, 3H), 0.84 (d, J=6.6 Hz, 3H); $^{13}$C NMR (125 MHz, Benzene-d$_6$) δ 204.7, 171.9, 124.6, 120.6, 60.0, 48.8, 41.7, 37.3, 27.6, 20.7, 13.8; IR (neat) ν 2977, 2931, 1730, 1716, 1408, 1197, 1174, 899; HRMS (ESI) calcd. for C$_{11}$H$_{18}$IO$_3$ [M+H]$^+$: 325.0295, found 325.0299.

FeBr$_2$(dppb) as a Catalyst:

In a glove box, an oven dried 250 mL single-necked flask equipped with a magnetic stirring bar was charged with FeBr$_2$(dppb) (1.03 g, 1.55 mmol), manganese (3.41 g, 62.2 mmol), copper (II) chloride (4.18 g, 31.1 mmol), lithium chloride (3.95 g, 93.3 mmol) and 1,2-dimethoxyethane (50 mL) at room temperature. A solution of (R)-2,4-diiodo-3-methylbut-1-ene (7) (10.0 g, 31.1 mmol) in 1,2-dimethoxyethane (28 mL) was charged into the above single-necked flask and added ethyl 4-chloro-4-oxobutanoate (6) (7.65 g, 46.7 mmol) into the reaction mixture. The reaction mixture was taken out from glove box, cooled to 0° C. and stirred the reaction mixture under nitrogen atmosphere for 15 hours. After completing the reaction florisil (15 g) was added to the reaction mixture and stirred for 30 min. Filtered the reaction mixture through Celite, washed the filter cake with ethyl acetate (50 mL) and concentrated under reduced pressure to afford the crude product which was then purified by flash column chromatography on silica gel to afford 7.24 g of (R)-ethyl 7-iodo-6-methyl-4-oxooct-7-enoate (8a) in 72% yield as a colorless liquid.

FeBr$_2$(SciOPP) as a Catalyst:

In a glove box, an oven dried 100 mL single-necked flask equipped with a Teflon-coated magnetic stirring bar was charged with FeBr$_2$(SciOPP) (860 mg, 0.78 mmol), manganese (1.7 g, 31.06 mmol), copper (II) chloride (2.08 g, 15.8 mmol), lithium chloride (1.97 g, 46.5 mmol) and 1,2-dimethoxyethane (25 mL) at room temperature. A solution of (R)-2,4-diiodo-3-methylbut-1-ene (7) (5.0 g, 15.5 mmol) in 1,2-dimethoxyethane (15 mL) was charged into the above single-necked flask and added ethyl 4-chloro-4-oxobutanoate (6) (3.8 g, 23.2 mmol) into the reaction mixture. The reaction mixture was taken out from glove box, cooled to 0° C. and stirred the reaction mixture under nitrogen atmosphere for 15 hours. After completing the reaction florisil (5 g) was added to the reaction mixture and stirred for 30 min. Filtered the reaction mixture through Celite, washed the filter cake with ethyl acetate (50 mL) and concentrated under reduced pressure to afford the crude product which was then purified by flash column chromatography on silica gel to afford 4.02 g of (R)-ethyl 7-iodo-6-methyl-4-oxooct-7-enoate (8a) in 80% yield as a colorless liquid.

(R)-ethyl 7-bromo-6-methyl-4-oxooct-7-enoate (S-2)

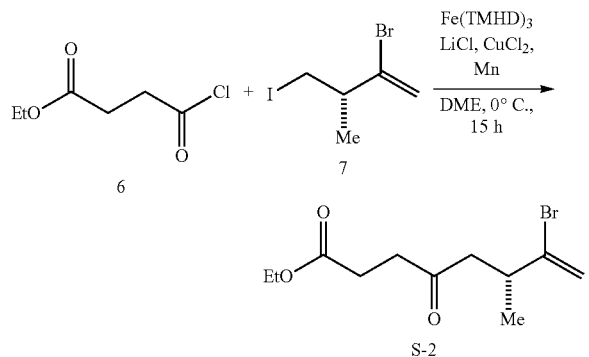

Compound S-2 was synthesized, according to the procedure for 8a using (S)-2-bromo-4-iodo-3-methylbut-1-ene (S-1) as a starting material in 76% yield. [ct]$D_{23}$ −6.4 (c 0.52, CHCl$_3$); 1H NMR (500 MHz, Benzene-d$_6$) δ 5.28-5.25 (m, 1H), 5.19-5.16 (m, 1H), 3.88 (q, J=7.5 Hz, 2H), 2.93-2.85 (m, 1H), 2.41-2.33 (m, 2H), 2.29-2.21 (m, 1H), 2.20-2.06 (m, 2H), 1.98 (dd, J=16.9, 7.5 Hz, 1H), 0.94-0.88 (m, 6H); $^{13}$C NMR (125 MHz, Benzene-d$_6$) δ 204.95, 171.89, 139.95, 115.87, 60.03, 47.49, 39.31, 37.18, 27.60, 19.34, 13.83; IR (neat) v 2974, 2929, 1729, 1714, 1408, 1189, 1172, 898; HRMS (ESI) calcd. for C$_{11}$H$_{17}$BrNaO$_3$ [M+Na]$^+$: 299.0253, found 299.0261.

Additional route to C20-C26 fragment

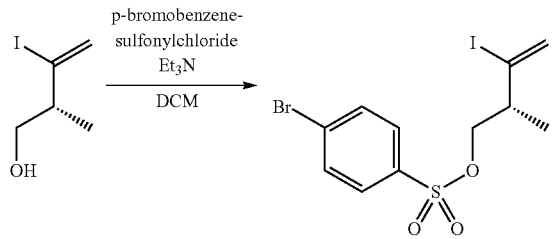

To a solution of the starting material (25.8 g, 0.121 mol), obtained by the synthetic method written in the Supporting Information of J. Am. Chem. Soc. 2009, 131, 15636-15641, in dichloromethane (258 mL) was added Et$_3$N (50.8 mL, 0.364 mol) followed by p-bromobenzenesulfonyl chloride (46.6 g, 0.182 mol) below 10° C. under N$_2$ atmosphere. After being stirred for 8 hrs at room temperature, the mixture was quenched with 5% NaCl aq. (130 mL) at 10-15° C. to give biphasic mixture. The separated organic layer was sequentially washed with a mixture of 5% NaCl aq./5N HCl=2.5/1 (w/w), 5% NaHCO$_3$ aq. and 5% NaCl aq. The organic layer was concentrated under reduced pressure to give a crude material. This crude material was dissolved in 1-propanol (209 mL) at 26° C. and cooled to 15° C. followed by addition of seed crystals (52 mg, 0.12 mmol). To this mixture, 1-propanol/water=1/3 (v/v) (419 mL) was added dropwise at 10-14° C., cooled to 0° C. and the resulting mixture was stirred for 4 hrs. The resulting suspension was filtrated and rinsed with 1-propanol/water=1/2 (v/v). The collected solid was dried at room temperature under reduced pressure to give desired compound (51.3 g, 0.119 mol, 98%).

$^1$H-NMR (500 MHz, CDCl$_3$) δ ppm 1.01 (d, J=6.7 Hz, 3H), 2.35 (tq, J=6.7 Hz, 1H), 3.91 (d, J=6.7 Hz, 2H), 5.82 (d, J=1.8 Hz, 1H), 6.21 (s, 1H), 7.65-7.75 (m, 2H), 7.75-7.83 (m, 2H).

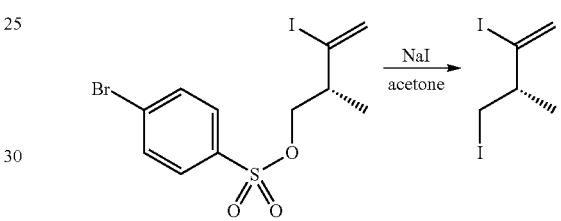

To a solution of the starting material (50.0 g, 0.116 mol) in acetone (150 mL) was added NaI (52.2 g, 0.348 mol) at room temperature under N$_2$ atmosphere and the resulting mixture was heated to 45° C. After being stirred for 25 hrs, the mixture was cooled to room temperature followed by addition of n-hexane (500 mL) and water (250 mL) to give biphasic mixture. The separated organic layer was sequentially washed with 5% NaHCO$_3$ aq., 10% Na$_2$S$_2$O$_3$ aq. and water. The organic layer was dried over Na$_2$SO$_4$, filtrated through a Celite® pad. The filtrated solution was concentrated under reduced pressure at 10-15° C. to give the crude iodide, which was purified by distillation under reduced pressure (bath temperature: 86-94° C., boiling point: 63-64° C. at 0.75 mmHg) to give pure iodide (22.9 g, 0.071 mol, 61%) as an orange oil.

$^1$H-NMR (500 MHz, CDCl$_3$) δ ppm 1.17 (d, J=6.7 Hz, 3H), 2.24 (tq, J=6.6 Hz, 1H), 3.14-3.20 (m, 2H), 5.86 (d, J=1.8 Hz, 1H), 6.20 (s, 1H).

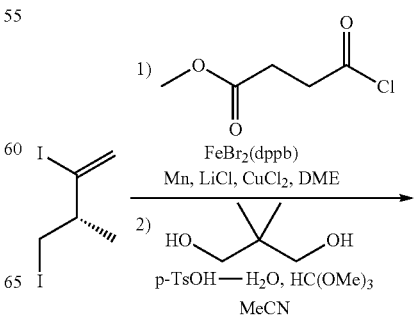

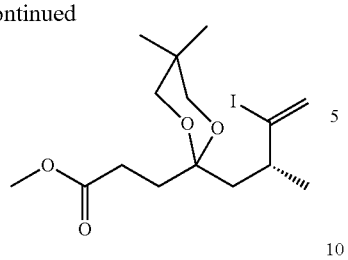

Under N₂ atmosphere in a glove box, LiCl (1.98 g, 46.6 mmol), CuCl₂ (0.418 g, 3.11 mmol), Mn (1.71 g, 31.1 mmol) and FeBr₂(dppb) (0.514 g, 0.777 mmol) were charged in a vial with screw cap. After the vial was taken out of the glove box, the mixture was quickly transferred to another flask filled with N₂. After the flask was purged with N₂ and cooled to 4° C., anhydrous DME (15 mL) was added followed by addition of a solution of the iodide (5.00 g, 15.5 mmol) in anhydrous DME (20 mL) below 12° C. without stirring. To this mixture, acid chloride (3.44 mL, 28.0 mmol) was added dropwise without stirring below 11° C. After being stirred for 22 hrs at 4° C., to the mixture was added MTBE (75 mL) followed by 20% citric acid aq. (50 mL) below 10° C. After being stirred for 30 min at room temperature, the mixture was passed through a Celite® pad and the residue was rinsed with MTBE. The resulting biphasic mixture was separated and the aqueous layer was extracted with MTBE twice. The combined organic layer was washed with 5% NaHCO₃ aq. The organic layer was concentrated under reduced pressure to give crude yellow oil, which was used in the next step without further purification.

To a stirred solution of crude product from the previous step (several batches of crude product combined and calculated as 37.3 mmol) in MeCN (47 mL) was added trimethyl orthoformate (6.12 mL, 56.0 mmol) and 2,2-dimethyl-1,3-propanediol (19.4 g, 187 mmol) followed by p-TsOH hydrate (0.142 g, 0.746 mmol) at room temperature. After being stirred for 20 hrs at room temperature, the mixture was cooled below 5° C. and diluted with n-heptane (175 mL) followed by addition of 5% NaHCO₃ aq. (58 mL) to give a biphasic mixture. The organic layer was separated and the aqueous layer was extracted with n-heptane twice. The combined organic layer was sequentially washed with water and 5% NaCl aq. The organic layer was passed through a neutral silica gel pad (70 g, eluent: 0%, 1.3%, 2% then 5% EtOAc in n-heptane). The collected fractions were concentrated under reduced pressure to give a pale yellow oil. This mixture was dissolved in MeOH/water=10/1 (v/v) (66 mL) at room temperature and cooled to 10-12° C. To this mixture, seed crystals were added and further cooled to 4° C. followed by dropwise addition of MeOH/water=3/5 (v/v) (57 mL). After being stirred for 19 hrs at 4° C., the suspension was filtrated and rinsed with cold MeOH/water=2/1 (v/v) (6lmL). The collected solid was dried under reduced pressure at room temperature to give the desired compound (12.1 g, 30.5 mmol, 82% (65% in 2 steps)) as a white solid.

¹H-NMR (500 MHz, C₆D₆) δ ppm 0.66 (s, 3H), 0.71 (s, 3H), 1.05 (d, J=6.7 Hz, 3H), 1.60 (dd, J=15.0, 5.8 Hz, 1H), 1.97 (dd, J=14.7, 5.5 Hz, 1H), 2.27-2.07 (m, 3H), 2.54 (ddd, J=9.2, 6.7, 2.4 Hz, 2H), 3.32-3.20 (m, 4H), 3.37 (s, 3H), 5.54 (d, J=1.8 Hz, 1H), 5.87 (s, 1H).

Synthesis of Diiodide 10

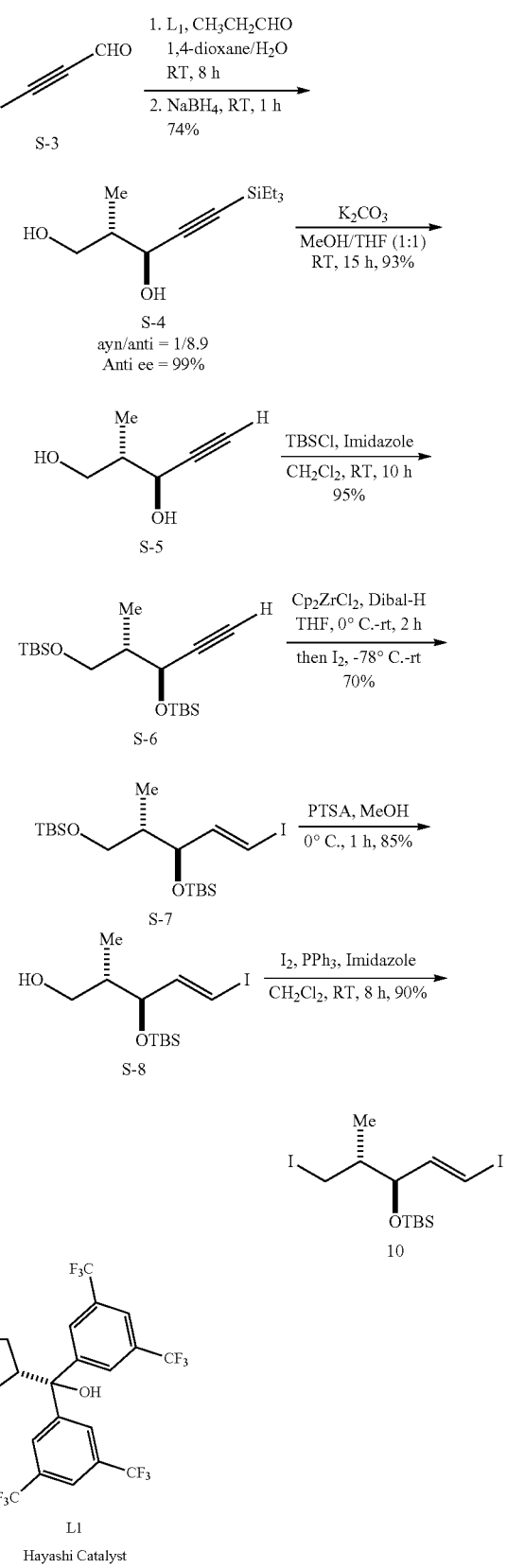

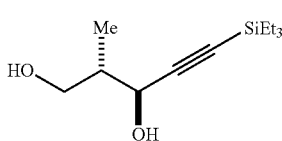

Compound S-4

To a 1,4-dioxane solution (30 mL, 1 M) of 3-(triethylsilyl) propiolaldehyde (See, e.g., McGee, P.; Bellavance, G.; Korobkov, I.; Tarasewicz, A.; Barriault, L. *Chem. Eur. J.* 2015, 21, 9662-9665)S-3 (5.0 g, 29.7 mmol) was added (R)-2-[bis(3,5-bis-trifluoromethyl-phenyl)hydroxymethyl] pyrrolidine L1 (See, e.g., Hayashi, Y.; Kojima, M.; Yasui, Y.; Kanda, Y.; Mukaiyama, T.; Shomura, H.; Nakamura, D.; Ritmaleni, Sato, I. *Chem Cat Chem* 2013, 5, 2887-2892) (1.56 g, 2.97 mmol), $H_2O$ (1.6 mL, 89.1 mmol) and propanal (4.3 mL, 59.5 mmol) at room temperature. After stirring the reaction mixture for 8 hours at room temperature, $NaBH_4$ (2.47 g, 65.3 mmol) was added at 0° C. After stirring the reaction mixture for 1 h at room temperature, the reaction was quenched by addition of buffer (pH=7.0). The organic materials were extracted with ethyl acetate (3×50 mL), and the extracts were washed with water and brine, dried over anhydrous $Na_2SO_4$, concentrated in vacuo to afford crude product. 1H NMR of the crude product revealed the syn/anti ratio as 8.9:1. The crude product was subjected to a silica gel column chromatography to get pure anti isomer S-4 as viscous liquid (5.05 g, 74%). $[t]D^{23}$+5.0 (c 2.5, $CHCl_3$); 1H NMR (600 MHz, Benzene-$d_6$) δ 4.25 (d, J=6.8 Hz, 1H), 3.57 (dd, J=10.8, 4.1 Hz, 1H), 3.38 (dd, J=10.7, 6.9 Hz, 1H), 2.71 (bs, 1H), 2.05 (bs, 1H), 1.85-1.76 (m, 1H), 1.02 (t, J=7.9 Hz, 9H), 0.91 (d, J=6.9 Hz, 3H), 0.58 (q, J=7.9 Hz, 6H); $^{13}C$ NMR (125 MHz, Benzene-$d_6$) δ 107.9, 86.7, 66.6, 65.7, 41.4, 12.8, 7.4, 4.4; IR (neat) v 3316, 2955, 2875, 2170, 1457, 1279, 1004, 977, 697; HRMS (ESI) calcd. for $C_{12}H_{24}NaO_2Si$ [M+Na]$^+$: 251.1438, found 251.1432.

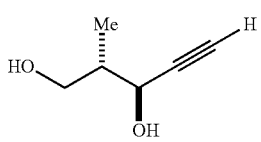

Compound S-5

To a solution of (2S,3S)-2-methyl-5-(triethylsilyl)pent-4-yne-1,3-diol S-4 (5.0 g, 21.91 mmol) in MeOH/THF (1:1, 70 mL), $K_2CO_3$ (6.05 g, 43.82 mmol) was added and the reaction was stirred at room temperature for 15 hours. Upon completion, the reaction mixture was diluted with hexane (100 mL) and filtered through a pad of Celite. The solids were washed with ethyl acetate (100 mL). The filtrate was concentrated under vacuum and the crude product was purified by a silica gel column chromatography yielded diol S-5 as viscous liquid (2.34 g, 93%). $[\alpha]D_{23}$ −0.7 (c 0.2, $CHCl_3$); 1H NMR (500 MHz, Benzene-$d_6$) δ 4.13 (ddd, J=6.9, 5.2, 2.1 Hz, 1H), 3.49-3.44 (m, 1H), 3.30-3.21 (m, 1H), 2.21 (d, J=5.2 Hz, 1H), 2.03-1.98 (m, 1H), 1.77-1.65 (m, 1H), 1.39-1.34 (m, 1H), 0.83 (dd, J=7.0, 1.2 Hz, 3H); $^{13}C$ NMR (125 MHz, Benzene-$d_6$) δ 83.95, 73.23, 65.96, 65.48, 41.06, 12.52; IR (neat) v 3289, 2966, 2934, 1457, 1381, 1025, 64; HRMS (ESI) calcd. for $C_6H_{10}NaO_2$ [M+Na]$^+$: 137.0573, found 137.0565.

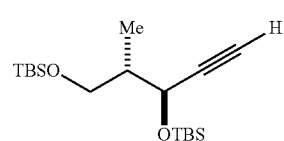

Compound S-6

To a stirred solution of 1,3-diol S-5 (2.3 g, 20.03 mmol) in $CH_2Cl_2$ (66 mL) were added TBS-$C_1$ (9.01 g, 60.09 mmol), imidazole (5.45 g, 80.12 mmol) and DMAP (244 mg, 2.01 mmol) at 0° C. The resulting solution was stirred at room temperature for 10 h. Then, the reaction was diluted with water (100 mL), the two layers were separated, and the aqueous layer washed with $CH_2Cl_2$ (2×50 mL). The combined organic layers were washed with brine, dried over $Na_2SO_4$, and concentrated under vacuum. The crude residue was subjected to a silica gel column chromatography to afford 6.85 g of di-TBS product S-6 in 95% yield. $[\alpha]D_{23}$ −13.9 (c 2.04, $CHCl_3$); 1H NMR (500 MHz, Benzene-$d_6$) δ 4.64 (ddd, J=6.0, 2.2, 1.0 Hz, 1H), 3.59 (d, J=6.0 Hz, 2H), 2.05-1.96 (m, 2H), 1.07 (dd, J=6.9, 0.8 Hz, 3H), 0.98 (d, J=0.9 Hz, 9H), 0.94 (d, J=0.9 Hz, 9H), 0.21 (s, 3H), 0.13 (s, 3H), 0.03 (s, 3H), 0.03 (s, 3H); $^{13}C$ NMR (125 MHz, Benzene-$d_6$) δ 83.7, 73.3, 64.3, 42.9, 25.7, 25.7, 18.1, 18.1, 11.7, −4.7, −5.4, −5.6, −5.7; IR (neat) v 2929, 2857, 1463, 1251, 1077, 833, 773; HRMS (ESI) calcd. for $C_{18}H_{38}NaO_2Si_2$ [M+Na]$^+$: 365.2305, found 365.2999.

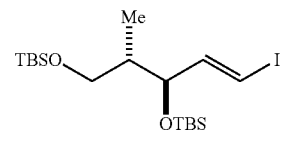

Compound S-7

To a solution of $ZrCp_2Cl_2$ (8.71 mg, 29.81 mmol) in THF (30 mL) was added slowly a solution of DIBAL-H (1.0 M in hexanes, 25.86 mL, 25.83 mmol) at 0° C. under argon. The resultant suspension was stirred for 2 h at room temperature. The reaction mixture was cooled to 0° C. then a solution of acetylene S-6 (6.8 g, 19.87 mmol) in THF (10 mL). The mixture was warmed to room temperature and stirred until a homogeneous solution resulted (ca. 2 h) and then cooled to −78° C., followed by addition of 12 (7.55 g, 29.81 mmol) in THF (20 mL). After 30 min at −78 (C, the reaction mixture temperature was raised to RT and stirred for 2 h. The reaction mixture was quenched with 1N HCl, extracted with ether, washed successively with saturated $Na_2S_2O_3$, $NaHCO_3$ and brine, dried over $Na_2SO_4$, filtered, and concentrated. Flash chromatography on silica gel afforded the title compound vinyl iodide S-7 as clear oil (6.53 g, 70%). $[\alpha]D_{23}$ −10.2 (c 1.89, $CHCl_3$); 1H NMR (500 MHz, Benzene-$d_6$) δ 6.53 (dd, J=14.5, 7.0 Hz, 1H), 6.09 (dd, J=14.5, 1.1 Hz, 1H), 4.07-4.04 (m, 1H), 3.47 (dd, J=10.0, 5.4 Hz, 1H), 3.41 (dd, J=10.0, 6.4 Hz, 1H), 1.74-1.64 (m, 1H), 0.94 (s, 9H), 0.91 (s, 9H), 0.76 (d, J=7.0 Hz, 3H), 0.01 (s, 3H), 0.01 (s, 3H), 0.00 (s, 3H), −0.01 (s, 3H); $^{13}C$ NMR (125 MHz, Benzene-$d_6$) δ 147.3, 76.5, 76.3, 64.2, 42.1, 25.8, 25.6, 18.1, 18.0, 11.9, −4.6, −5.3, −5.6, −5.7; IR (neat) v 2954, 2928, 2856, 1471, 1251, 1098, 831, 772, 668; HRMS (ESI) calcd. for $C_{18}H_{39}INaO_2Si_2$ [M+Na]$^+$: 493.1425, found 493.1416.

Compound S-8

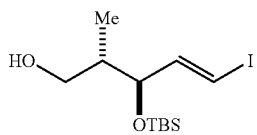

4-Toluenesulfonic acid (238 mg, 10 mol %) was added to a solution of S-6 (6.5 g, 13.82 mmol) in MeOH (45 mL) at 0° C. The reaction mixture was stirred at this temperature for 1h then quenched with Et₃N (2 mL) and stirred for 30 min. Then, the reaction mixture was concentrated under vacuum and the crude residue was purified by a silica gel column chromatography afforded pure alcohol S-8 (4.18 g) as a clear liquid in 85% yield. $[\alpha]_D^{23}$ −34.2 (c 4.53, CHCl₃); ¹H NMR (500 MHz, Benzene-d₆) δ 6.43-6.37 (m, 1H), 6.01-5.97 (m, 1H), 3.81 (dd, J=85.9, 5.9 Hz, 1H), 3.41-3.35 (m, 1H), 3.28-3.23 (m, 1H), 1.52-1.43 (m, 1H), 1.20 (t, J=5.3 Hz, 1H), 0.87 (s, 9H), 0.67 (d, J=7.0 Hz, 3H), −0.05 (s, 3H), −0.07 (s, 3H); ¹³C NMR (125 MHz, Benzene-d₆) δ 147.5, 78.1, 76.8, 64.3, 41.1, 25.6, 17.9, 12.5, −4.7, −5.3; IR (neat) v 2954, 2928, 2856, 1462, 1252, 1067, 1027, 833, 774, 674; HRMS (ESI) calcd. for $C_{12}H_{25}INaO_2Si$ [M+Na]⁺: 379.0561, found 379.0543.

Compound 10

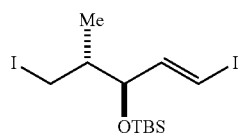

To a solution of primary alcohol S-8 (4.1 g, 11.51 mmol) in CH₂Cl₂ (40 mL) were added successively triphenylphosphine (3.62 g, 13.81 mmol) and imidazole (1.17 g, 17.26 mmol). After complete dissolution, the mixture was cooled to 0° C., and iodine (3.79 g, 14.96 mmol) was added. After 30 min at 0° C., the mixture was warmed to rt and stirred for 8 h. The solvent was removed in vacuo, and the crude was purified by flash chromatography on silica gel to afford diiodide 10 (4.82 g, 90%) as colorless oil. $[\alpha]_D^{20}$=−1.1 (c 1.77, CHCl₃); 1H NMR (500 MHz, Benzene-d₆) δ 6.21 (dd, J=14.5, 7.7 Hz, 1H), 5.89 (dd, J=14.5, 0.8 Hz, 1H), 3.63 (t, J=6.8 Hz, 1H), 3.00 (dd, J=9.7, 5.6 Hz, 1H), 2.79 (dd, J=9.7, 4.7 Hz, 1H), 1.12-1.04 (m, 1H), 0.87 (s, 9H), 0.61 (d, J=6.7 Hz, 3H), 0.00 (s, 3H), −0.05 (s, 3H); ¹³C NMR (125 MHz, Benzene-d₆) δ 146.4, 78.4, 78.1, 40.1, 25.6, 17.9, 16.1, 12.8, −4.5, −5.0; IR (neat) v 2954, 2927, 2855, 1470, 1250, 1080, 1064, 833, 774; HRMS (ESI) calcd. for $C_{12}H_{25}I_2OSi$ [M+H]⁺: 466.9759, found 466.9750.

Synthesis of 9a and 9b

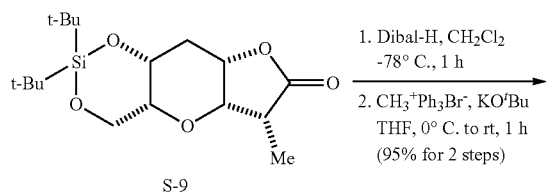

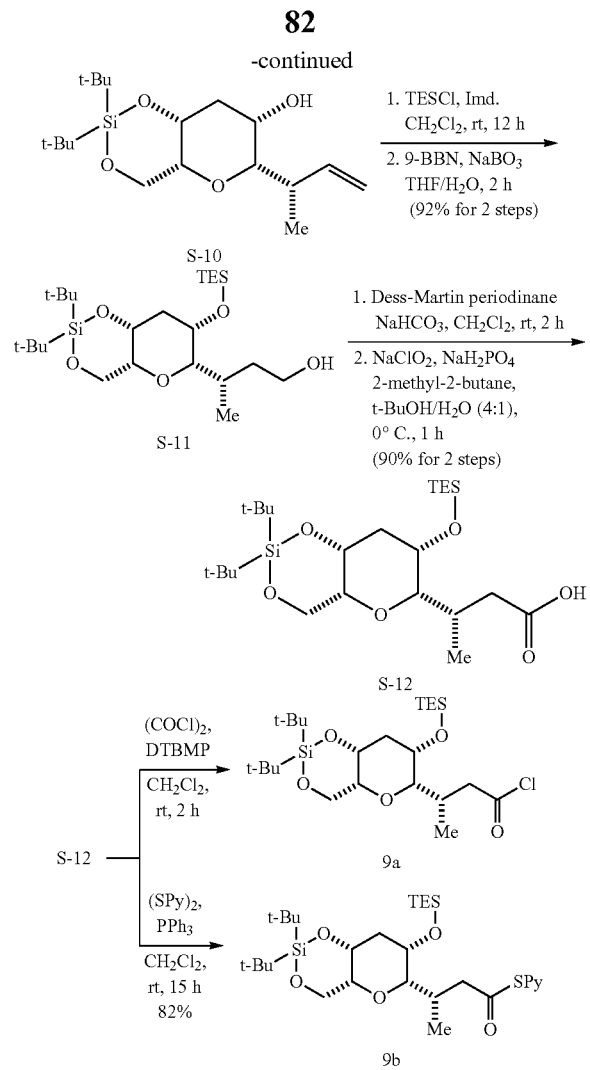

Compound S-8

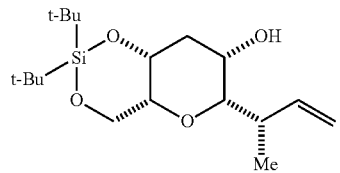

DIBAL-H (1.0 M in hexanes, 3.8 mL, 3.79 mmol) was added dropwise to a solution of lactone S-7 in CH₂Cl₂ (14 mL) at −78° C. under an argon atmosphere. The reaction mixture was stirred for 1 hour at −78° C., and quenched with methanol (0.2 mL) followed by addition of sodium potassium tartrate solution (10 mL) and stirred the resulting solution at room temperature for 1 hour. The organic layer was separated and the aqueous layer was extracted with CH₂Cl₂(2×50 mL). The combined organic layers were washed with water and brine and then dried (Na₂SO₄), filtered, and concentrated to yield lactal as a colorless liquid in quantitative yield. The crude product was used directly for the next reaction without further purification.

To a solution of methyltriphenylphosphonium bromide (4.17 g, 11.68 mmol) in THF (10 mL) was added Kt-OBu (982 mg, 8.76 mmol) at 0° C. and the resulting in an orange suspension was stirred at room temperature for 1h. A solution of above prepared lactal in THF (4 mL) was added dropwise via syringe over a period of 10 min at 0° C., and the suspension was stirred for 1 h at RT. A saturated aqueous solution of NH$_4$Cl (10 mL) was added followed by dilution of the bi-phasic mixture with EtOAc (20 mL). The aqueous layer was extracted with EtOAc (2×20 mL). The combined organic layers were dried (MgSO$_4$), filtered, and concentrated under reduced pressure. The crude product was purified by a silica gel column chromatography yielded olefin S-8 (948 mg, 95% for 2 steps) as a colorless liquid. $[\alpha]_D^{23}$ −40.5 (c 1.26, CHCl$_3$); 1H NMR (500 MHz, Benzene-d$_6$) δ 6.21-6.12 (m, 1H), 5.15 (dt, J=17.3, 1.7 Hz, 1H), 5.11 (ddd, J=10.4, 1.9, 1.2 Hz, 1H), 4.10 (dd, J=12.3, 1.3 Hz, 1H), 3.91-3.89 (m, 1H), 3.80 (dd, J=12.3, 2.9 Hz, 1H), 3.70 (d, J=10.7 Hz, 1H), 3.58-3.53 (m, 1H), 3.02-2.93 (m, 1H), 2.71 (dd, J=9.5, 1.3 Hz, 1H), 2.61-2.59 (m, 1H), 2.15 (dt, J=14.6, 3.0 Hz, 1H), 1.16 (s, 9H), 1.12 (m, 1H), 1.05 (d, J=6.9 Hz, 3H), 1.02 (s, 9H); $^{13}$C NMR (125 MHz, Benzene-d$_6$) δ 142.3, 113.2, 85.1, 76.1, 69.3, 68.3, 63.9, 38.2, 36.6, 27.6, 27.2, 23.0, 20.2, 14.6; IR (neat) v 3504, 2966, 2933, 1473, 1133, 1092, 949, 825, 736; HRMS (ESI) calcd. for C$_{18}$H$_{35}$O$_4$Si [M+H]$^+$: 343.2299, found 343.2285.

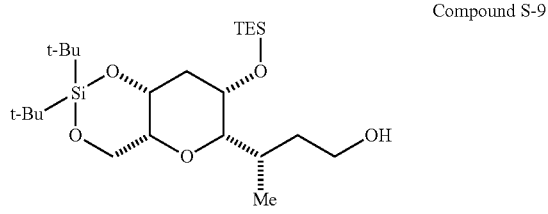

Compound S-9

To a solution of alcohol S-8 (948 mg, 2.76 mmol) in CH$_2$Cl$_2$ (14 mL) at room temperature was added imidazole (470 mg, 6.9 mmol) followed by TES-C$_1$ (0.7 mL, 4.15 mmol). The reaction mixture was stirred at room temperature for 12 h. Upon completion of reaction, methanol (1 mL) was added, and the clear and colorless solution was stirred for 10 min. All volatiles were removed, the resulting crude residue was dried under high vacuum and used for the next step without further purification.

9-BBN (0.5 M in THF, 8.27 mL, 4.14 mmol) was added in dropwise to a solution of above prepared crude residue in THF (14 mL) at 0° C. The clear and colorless solution was stirred for 2 h at room temperature. At this point, TLC analysis indicated complete consumption of starting material. The solution was cooled to 0° C., and water (8.3 mL) was added (gas evolution!), followed by sodium perborate tetrahydrate (2.47 g, 24.84 mmol). The white suspension was allowed to warm to room temperature and stirred for 2 h. The white suspension was filtered and washed with EtOAc (20 mL). The organic layer was diluted with water (20 mL). The layers were separated, and the aqueous phase was extracted three times with 20 mL portions of ethyl acetate. The combined organic phases were washed with water, brine, filtered and concentrated, purified by a silica gel column to afford primary alcohol S-9 (1.21 g, 92% for 2 steps) as viscous liquid. $[\alpha]D_{23}$+4.1 (c 1.16, CHCl$_3$); 1H NMR (500 MHz, Benzene-d$_6$): δ 4.18 (dd, J=12.4, 1.5 Hz, 1H), 3.94 (dd, J=12.4, 2.5 Hz, 1H), 3.89-3.86 (m, 1H), 3.72-3.60 (m, 1H), 3.57-3.52 (m, 1H), 2.64-2.59 (m, 2H), 2.25-2.13 (m, 1H), 2.03 (dt, J=14.9, 2.5 Hz, 1H), 1.93-1.83 (m, 1H), 1.70 (br. s, 1H), 1.54-1.45 (m, 1H), 1.28 (s, 9H), 1.19 (dt, J=14.8, 3.9 Hz, 1H), 1.11 (s, 9H), 1.05 (t, J=8.0 Hz, 9H), 0.81 (d, J=6.8 Hz, 3H), 0.76-0.61 (m, 6H); $^{13}$C NMR (125 MHz, Benzene-d$_6$) δ 86.0, 76.9, 67.8, 67.6, 63.7, 61.4, 38.4, 37.5, 31.2, 27.7, 27.3, 23.2, 20.6, 16.7, 7.0, 5.2; IR (neat) v 2953, 2933, 2875, 1473, 1156, 1106, 1034, 926, 827, 800, 736, 441; HRMS (ESI) calcd. for C$_{24}$H$_{50}$NaO$_5$Si$_2$ [M+Na]$^+$: 497.3089, found 497.3070.

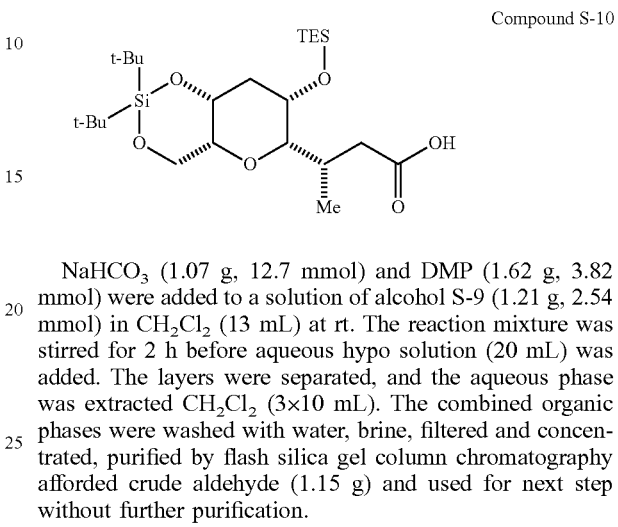

Compound S-10

NaHCO$_3$ (1.07 g, 12.7 mmol) and DMP (1.62 g, 3.82 mmol) were added to a solution of alcohol S-9 (1.21 g, 2.54 mmol) in CH$_2$Cl$_2$ (13 mL) at rt. The reaction mixture was stirred for 2 h before aqueous hypo solution (20 mL) was added. The layers were separated, and the aqueous phase was extracted CH$_2$Cl$_2$ (3×10 mL). The combined organic phases were washed with water, brine, filtered and concentrated, purified by flash silica gel column chromatography afforded crude aldehyde (1.15 g) and used for next step without further purification.

A solution of NaClO$_2$ (549 mg, 6.08 mmol) and NaH$_2$PO$_4$ (1.0 g, 7.29 mmol) in H$_2$O (2.0 mL) was added to a solution of aldehyde in t-BuOH (10 mL) and 2-methyl-2-butene (1.7 mL) at 0° C. After stirring for 1 h, the reaction was quenched by the addition of pH 7 buffer (8 mL). The mixture was extracted with CH$_2$Cl$_2$ (3×15 mL) and the combined organic extracts were washed with brine, dried (Na$_2$SO$_4$), filtered and concentrated. The crude product was purified by a silica gel column chromatography yielded acid S-10 (1.12 g) in 90% yield. $[\alpha]_D^{23}$ −1.8 (c 1.17, CHCl$_3$); 1H NMR (500 MHz, Benzene-d$_6$): δ 4.19 (dd, J=12.3, 1.5 Hz, 1H), 3.95 (dd, J=12.3, 2.6 Hz, 1H), 3.91-3.86 (m, 1H), 3.54-3.49 (m, 1H), 2.72 (dd, J=9.2, 1.8 Hz, 1H), 2.68 (dd, J=15.3, 5.2 Hz, 1H), 2.66-2.64 (m, 1H), 2.63-2.56 (m, 1H), 2.33 (dd, J=15.3, 7.2 Hz, 1H), 2.01 (dt, J=14.9, 2.4 Hz, 1H), 1.28 (s, 9H), 1.19 (dt, J=14.9, 4.0 Hz, 1H), 1.11 (s, 9H), 1.04 (t, J=8.0 Hz, 9H), 0.90 (d, J=6.8 Hz, 3H), 0.75-0.59 (m, 6H); $^{13}$C NMR (125 MHz, Benzene-d$_6$) δ 179.9, 84.6, 76.9, 67.7, 67.5, 63.6, 38.4, 38.1, 30.8, 27.7, 27.3, 23.2, 20.6, 16.0, 6.9, 5.2; IR (neat) v 2954, 2934, 2875, 1705, 1473, 1155, 1106, 1034, 927, 826, 736, 441; HRMS (ESI) calcd. for C$_{24}$H$_{48}$NaO$_6$Si$_2$ [M+Na]$^+$: 511.2882, found 511.2875.

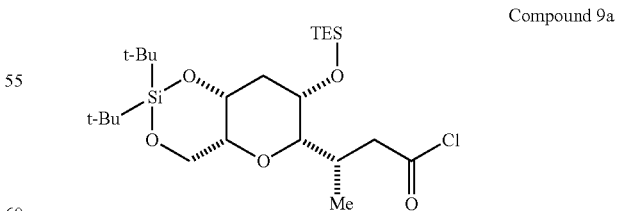

Compound 9a

A solution of acid S-10 (60 mg, 0.12 mmol), DTBMP (40 mg, 0.18) in CH$_2$Cl$_2$ (0.5 mL) was added oxalyl chloride (30 mg, 0.24 mmol) at 0° C. and stirred for 2 h at same temperature. Then, all volatiles were removed under vacuum. The residue was diluted with benzene (2 mL), and passed through a small pad of Celite. The solids were washed with benzene (5 mL), concentrated under vacuum and dried under high vacuum for 1 h to afford acid chloride 9a as pale yellow liquid. The resulting product was used for the next step without further purification. 1H NMR (400 MHz, Benzene-$d_6$) δ 4.13 (d, J=12.4 Hz, 1H), 3.89 (dd, J=12.4, 2.5 Hz, 1H), 3.84-3.79 (m, 1H), 3.39-3.33 (m, 1H), 2.98 (dd, J=16.6, 4.2 Hz, 1H), 2.67-2.54 (m, 2H), 2.54-2.44 (m, 2H), 2.00-1.90 (m, 3H), 1.25 (s, 8H), 1.09 (s, 9H), 1.00 (t, J=7.9 Hz, 9H), 0.74 (d, J=6.7 Hz, 3H), 0.69-0.53 (m, 7H); $^{13}$C NMR (125 MHz, Benzene-$d_6$) δ 172.83, 83.56, 76.96, 67.59, 67.32, 63.52, 50.42, 38.16, 31.61, 27.69, 27.29, 27.21, 23.17, 20.58, 15.50, 6.88, 5.06; IR (neat) v 2954, 2934, 2875, 1707, 1419, 1155, 1105, 1034, 927, 828, 771, 419; ESI-MS (M-Cl+OMe) 525.3026.

Compound 9b

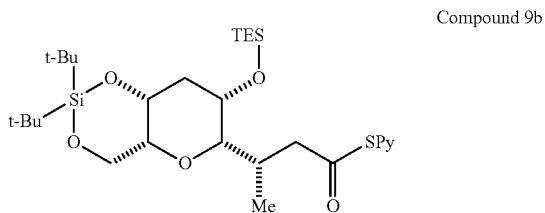

A solution of acid S-10 (1.12 g, 2.29 mmol), triphenylphosphine (900 mg, 3.43 mmol) and 2,2'-dipyridyl disulfide (605 mg, 2.75 mmol) dissolved in $CH_2Cl_2$ (12 mL) was stirred under $N_2$ at RT for 15 h. The reaction mixture was concentrated to yellow oil and purified by silica gel chromatography to give the title compound 9b as a white solid (1.09 mg, 82%). $[t]D^{23}$ −26.5 (c 1.97, $CHCl_3$); 1H NMR (500 MHz, Benzene-$d_6$) δ 8.33-8.28 (m, 1H), 7.63 (d, J=7.9 Hz, 1H), 6.98 (td, J=7.7, 2.0 Hz, 1H), 6.45 (ddd, J=7.5, 4.8, 1.1 Hz, 1H), 4.35-4.25 (m, 1H), 3.95 (dd, J=12.3, 2.6 Hz, 1H), 3.91-3.86 (m, 1H), 3.52-3.45 (m, 1H), 2.89 (dd, J=14.2, 3.5 Hz, 1H), 2.76-2.61 (m, 4H), 2.04-1.97 (m, 1H), 1.30 (s, 9H), 1.17 (dt, J=14.7, 4.0 Hz, 1H), 1.12 (s, 9H), 1.05 (t, J=7.9 Hz, 9H), 0.91 (d, J=6.0 Hz, 3H), 0.77-0.58 (m, 6H); $^{13}$C NMR (125 MHz, Benzene-$d_6$) δ 194.9, 153.0, 149.9, 136.0, 129.6, 122.5, 84.2, 76.9, 67.7, 67.6, 63.5, 47.5, 38.3, 31.8, 27.7, 27.3, 23.2, 20.6, 15.8, 7.0, 5.1; IR (neat) v 2954, 2934, 2875, 1707, 1419, 1155, 1105, 1034, 927, 828, 771, 419; HRMS (ESI) calcd. for $C_{29}H_{51}NNaO_5SSi_2$ [M+Na]$^+$: 604.2919, found 604.2905.

Compound 11

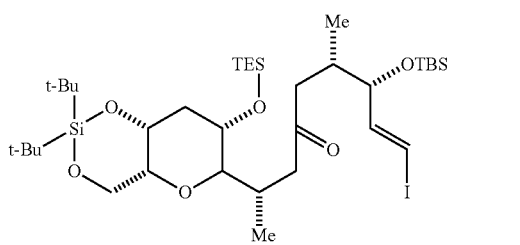

Using Acid Chloride 9a:

An oven dried 2 mL vial was charged with $FeBr_2$(Sci-OPP) (5.6 mg, 0.005 mmol), manganese (11.2 mg, 0.204 mmol), copper (II) chloride (13.80 mg, 0.102 mmol), lithium chloride (13 mg, 0.306 mmol), diiodide 10 (57 mg, 0.122) and acid chloride 9a (52 mg, 0.102 mmol) in 1,2-dimethoxyethane (0.3 mL). The reaction mixture was taken out from glove box, cooled to 0° C. and stirred the reaction mixture under nitrogen atmosphere for 15 hours. After completing the reaction florisil (10 mg) was added to the reaction mixture and stirred for 30 min at 0° C. Filtered the reaction mixture through Celite, washed the filter cake with ethyl acetate (10 mL) and concentrated under reduced pressure to afford the crude product which was then purified by preparative TLC to afford 20.8 mg (25%) of ketone 11 as a viscous colorless liquid. According to the above procedure, ketone coupling undergo in the presence of $FeBr_2$(dppb) as radical initiator afforded 20% product.

Using Thioester 9b:

An oven dried 100 mL single-necked flask was charged with $FeBr_2$(SciOPP) (71 mg, 0.064 mmol), manganese (140 mg, 2.56 mmol), copper (I) iodide (243 mg, 1.28 mmol), lithium chloride (162 mg, 3.84 mmol) and 1,2-dimethoxyethane (4.0 mL) at room temperature. A solution of thio ester 9b (600 mg, 1.03 mmol) and diiodide 10 (578 mg, 1.24 mmol) in 1,2-dimethoxyethane (2.5 mL) was charged into the above single-necked flask. The reaction mixture was taken out from glove box, cooled to 0° C. and stirred the reaction mixture under nitrogen atmosphere for 15 hours. After completing the reaction florisil (3 g) was added to the reaction mixture and stirred for 30 min at 0° C. Filtered the reaction mixture through Celite, washed the filter cake with ethyl acetate (20 mL) and concentrated under reduced pressure to afford the crude product which was then purified by flash column chromatography on silica gel to afford 593 mg (71%) of ketone 11 as a viscous colorless liquid. $[α]_D^{23}$ −29.3 (c 4.8, $CHCl_3$); 1H NMR (500 MHz, Benzene-$d_6$) δ 6.39 (dd, J=14.4, 6.2 Hz, 1H), 6.08 (dd, J=14.4, 1.1 Hz, 1H), 4.13 (dd, J=12.4, 1.6 Hz, 1H), 3.96 (dd, J=12.3, 2.5 Hz, 1H), 3.92-3.87 (m, 1H), 3.81-3.78 (m, 1H), 3.56-3.52 (m, 1H), 2.81-2.73 (m, 2H), 2.63-2.65 (m, 1H), 2.59-2.50 (m, 1H), 2.36 (dd, J=16.7, 4.3 Hz, 1H), 2.26-2.18 (m, 2H), 2.12 (dd, J=16.7, 8.6 Hz, 1H), 2.01 (dt, J=14.9, 2.4 Hz, 1H), 1.27 (s, 9H), 1.22 (dt, J=14.7, 3.9 Hz, 1H), 1.10 (s, 9H), 1.04 (t, J=8.0 Hz, 9H), 0.93 (d, J=6.8 Hz, 3H), 0.89 (s, 9H), 0.85 (d, J=6.7 Hz, 3H), 0.74-0.59 (m, 6H)−0.01 (s, 3H),−0.04 (s, 3H); $^{13}$C NMR (125 MHz, Benzene-$d_6$) δ 208.2, 147.2, 84.5, 78.4, 76.9, 76.6, 67.8, 67.6, 63.9, 46.7, 44.6, 38.4, 34.7, 30.4, 27.7, 27.3, 25.7, 25.7, 23.2, 20.7, 18.0, 16.5, 15.5, 7.0, 5.1,−4.7,−5.2; IR (neat) v 2954, 2932, 2875, 1709, 1472, 1161, 1105, 1007, 927, 827, 772, 737, 441; HRMS (ESI) calcd. for $C_{36}H_{71}INaO_6Si_3$ [M+Na]$^+$: 833.3495, found 833.3465.

Synthesis of Thioester 12

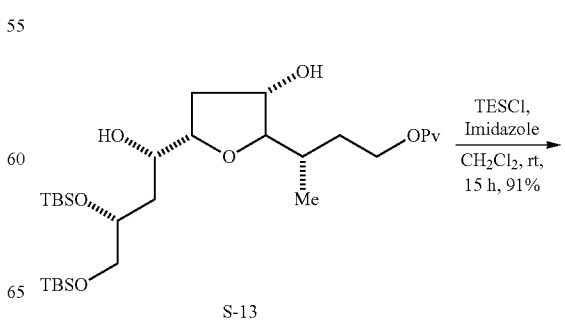

S-13

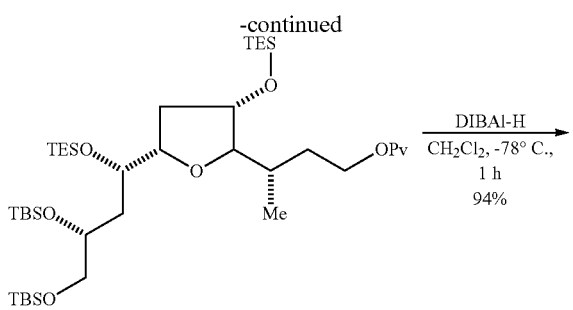

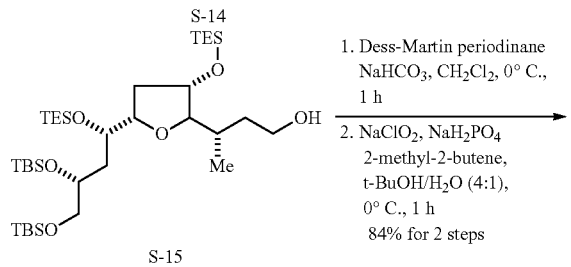

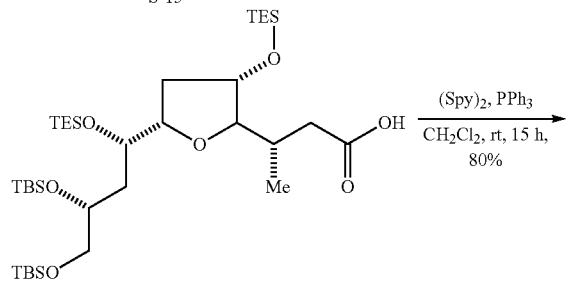

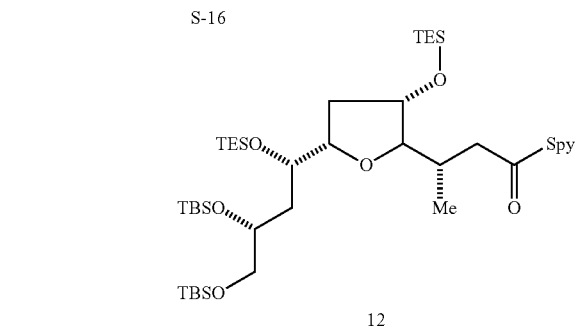

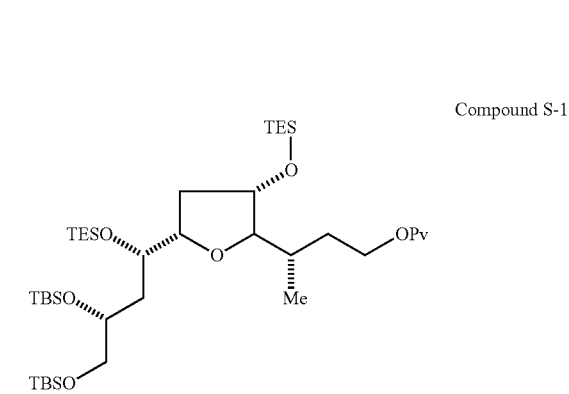

To a stirred solution of diol S-13 (400 mg, 0.69 mmol) in CH$_2$Cl$_2$ (2 mL) were added TES-C$_1$ (311 mg, 2.07 mmol), imidazole (234 mg, 3.45 mmol) at 0° C. The resulting solution was stirred at room temperature for 15 h. Then, the reaction was diluted with water (10 mL), the two layers were separated, and the aqueous layer washed with CH$_2$Cl$_2$ (3×10 mL). The combined organic layers were washed with brine, dried over Na$_2$SO$_4$, and concentrated under vacuum. The crude residue was subjected to a silica gel column chromatography to afford 508 mg of titled product S-14 in 91% yield. [c]D$_{23}$+0.6 (c 0.2, CHCl$_3$); 1H NMR (500 MHz, Benzene-d$_6$) δ 4.29-4.21 (m, 3H), 4.06-4.00 (m, 1H), 3.96-3.92 (m, 1H), 3.82 (dd, J=10.3, 3.0 Hz, 1H), 3.77-3.67 (m, 2H), 2.95 (dd, J=9.1, 3.7 Hz, 1H), 2.35-2.26 (m, 1H), 2.20-2.11 (m, 1H), 2.01-1.94 (m, 1H), 1.94-1.87 (m, 1H), 1.77-1.69 (m, 1H), 1.60-1.50 (m, 2H), 1.22 (s, 9H), 1.12 (t, J=8.0 Hz, 9H), 1.07 (s, 9H), 1.02 (s, 9H), 0.96 (t, J=7.9 Hz, 9H), 0.84 (d, J=6.7 Hz, 3H), 0.83-0.76 (m, 6H), 0.55 (qd, J=7.9, 2.0 Hz, 6H), 0.27 (s, 3H), 0.27 (s, 3H), 0.14 (s, 3H), 0.14 (s, 3H); $^{13}$C NMR (125 MHz, Benzene-d$_6$) δ 177.3, 87.8, 80.9, 72.1, 71.7, 71.0, 67.9, 62.6, 38.5, 38.4, 38.4, 32.5, 29.3, 27.0, 25.9, 18.3, 18.1, 15.9, 7.0, 6.8, 6.7, 6.4, 5.4, 4.9,−4.3,−4.6,−5.4,−5.5; IR (neat) ν 2955, 2936, 1730, 1461, 1239, 1075, 1004, 850, 776. 740; HRMS (ESI) calcd. for C$_{41}$H$_{88}$NaO$_7$Si$_4$ [M+Na]$^+$: 827.599, found 827.5517.

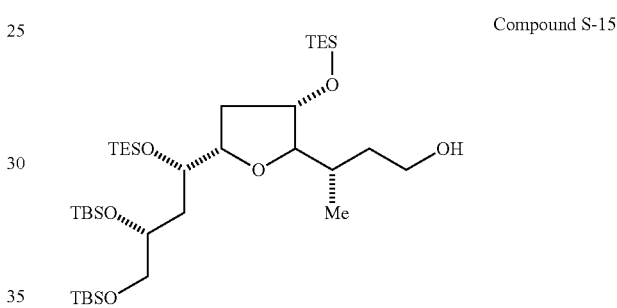

DIBAL-H (1.0 M in hexanes, 1.55 mL, 1.55 mmol) was added dropwise to a solution of lactone S-14 in CH$_2$Cl$_2$ (4 mL) at −78° C. under an argon atmosphere. The reaction mixture was stirred for 1 hour at −78° C., and quenched with methanol (0.2 mL) followed by addition of sodium potassium tartrate solution (10 mL) and stirred the resulting solution at room temperature for 1 hour. The organic layer was separated and the aqueous layer was extracted with CH$_2$Cl$_2$ (2×20 mL). The combined organic layers were washed with water and brine and then dried (Na$_2$SO$_4$), filtered, concentrated and flash silica gel chromatography gave primary alcohol S-15 (420 mg, 94%) as clear oil. [c]D$_{23}$+4.3 (c 1.22, CHCl$_3$); 1H NMR (500 MHz, Benzene-d$_6$) δ 4.27-4.20 (m, 1H), 4.06 (ddd, J=7.9, 6.6, 3.7 Hz, 1H), 3.96 (ddd, J=5.9, 3.6, 1.9 Hz, 1H), 3.86-3.79 (m, 2H), 3.72-3.68 (m, 2H), 3.64 (ddt, J=10.6, 7.6, 5.6 Hz, 1H), 3.04 (dd, J=9.0, 3.6 Hz, 1H), 2.18 (dtd, J=9.1, 7.0, 4.8 Hz, 1H), 2.06-1.96 (m, 2H), 1.92 (ddd, J=14.1, 8.3, 6.2 Hz, 1H), 1.74 (ddd, J=14.0, 8.0, 4.7 Hz, 1H), 1.70 (dd, J=6.1, 5.1 Hz, 1H), 1.64 (ddd, J=13.5, 6.8, 2.0 Hz, 1H), 1.59-1.51 (m, 1H), 1.11 (t, J=8.0 Hz, 9H), 1.07 (s, 9H), 1.01 (s, 9H), 0.97 (t, J=7.9 Hz, 9H), 0.87 (d, J=6.7 Hz, 3H), 0.79 (qd, J=7.9, 1.7 Hz, 6H), 0.56 (qd, J=7.9, 2.4 Hz, 6H), 0.28 (s, 3H), 0.26 (s, 3H), 0.14 (s, 3H), 0.13 (s, 3H); $^{13}$C NMR (125 MHz, Benzene-d$_6$) δ 88.0, 80.6, 71.8, 71.7, 70.9, 67.9, 60.8, 38.4, 38.0, 37.6, 30.0, 25.9, 18.3, 18.9, 16.9, 7.0, 6.8, 5.3, 4.9,−4.3,−4.6,−5.5,−5.6; IR (neat) ν 2953, 2928, 2877, 1471, 1462, 1250, 1076, 1004, 843, 775, 737. 726; HRMS (ESI) calcd. for $C_{36}H_{80}KO_6Si_4$ [M+K]$^+$: 759.4664, found 759.4690.

Compound S-16

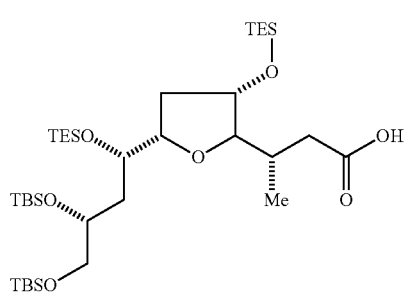

NaHCO$_3$ (243 mg, 2.9 mmol) and Dess-Martin periodinane (370 mg, 0.87 mmol) were added to a solution of alcohol S-15 (420 mg, 0.58 mmol) in CH$_2$Cl$_2$ (4 mL) at 0° C. The reaction mixture was stirred for 1 h before aqueous hypo solution (20 mL) was added. The layers were separated, and the aqueous phase was extracted CH$_2$Cl$_2$ (3×10 mL). The combined organic phases were washed with water, brine, filtered and concentrated, purified by flash silica gel column chromatography afforded crude aldehyde (400 mg) and it was used for next step without further purification.

A solution of NaClO$_2$ (132 mg, 1.45 mmol), 2-methyl-2-butene (0.4 mL, 5.8 mmol) and NaH$_2$PO$_4$ (240 mg, 1.74 mmol) was added to a solution of aldehyde in t-BuOH (4 mL), and H$_2$O (1 mL) at 0° C. After stirring for 1 h, the reaction was quenched by the addition of pH 7 buffer (4 mL). The mixture was extracted with CH$_2$Cl$_2$ (3×10 mL) and the combined organic extracts were washed with brine, dried (Na$_2$SO$_4$), filtered and concentrated. The crude product was purified by a silica gel column chromatography yielded acid S-16 (360 mg) in 84% yield. [0]$D_{23}$+14.3 (c 1.7, CHCl$_3$); 1H NMR (500 MHz, Benzene-d$_6$) δ 4.25-4.19 (m, 1H), 4.03 (ddd, J=8.2, 6.6, 3.8 Hz, 1H), 3.95 (ddd, J=6.6, 4.2, 2.7 Hz, 1H), 3.76-3.68 (m, 2H), 3.79 (dd, J=10.3, 3.4 Hz, 1H), 3.08 (dd, J=8.0, 4.1 Hz, 1H), 3.04 (dd, J=15.9, 3.2 Hz, 1H), 2.63-2.54 (m, 1H), 2.30 (dd, J=15.9, 9.9 Hz, 1H), 1.99 (ddd, J=13.8, 8.1, 3.8 Hz, 1H), 1.91 (ddd, J=13.9, 7.9, 6.3 Hz, 1H), 1.73 (ddd, J=13.5, 8.2, 4.7 Hz, 1H), 1.60 (ddd, J=13.4, 7.4, 2.8 Hz, 1H), 1.10 (t, J=8.0 Hz, 9H), 1.06 (s, 9H), 1.02 (d, J=6.9 Hz, 3H), 1.01 (s, 9H), 0.95 (t, J=7.9 Hz, 9H), 0.78 (qd, J=7.9, 2.8 Hz, 6H), 0.58-0.49 (m, 6H), 0.25 (s, 3H), 0.25 (s, 3H), 0.13 (s, 3H), 0.13 (s, 3H); $^{13}$C NMR (125 MHz, Benzene-d$_6$) δ 170.0, 86.3, 80.8, 72.0, 71.9, 70.8, 67.8, 38.6, 38.5, 38.1, 29.6, 25.9, 18.3, 18.1, 16.7, 7.0, 6.7, 5.3, 4.8, −4.4,−4.7,−5.5,−5.6; IR (neat) v 2953, 2929, 2877, 1708, 1462, 1250, 1076, 1004, 833, 774, 737; HRMS (ESI) calcd. for $C_{36}H_{79}O_7Si_4$ [M+H]$^+$: 735.4897, found 735.4897.

Compound 12

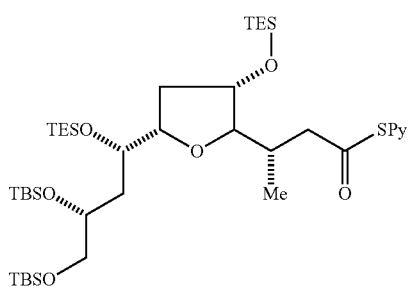

A solution of acid S-16 (300 mg, 0.41 mmol), triphenylphosphine (161 mg, 0.61 mmol) and 2,2'-dipyridyl disulfide (99 mg, 0.45 mmol) dissolved in CH$_2$Cl$_2$ (2 mL) was stirred under N$_2$ for 24 h. The reaction mixture was concentrated to yellow oil and purified by silica gel chromatography to give the title compound 12 as pale yellow solid (270 mg, 80%). [α]$D_{23}$+16.3 (c 3.1, CHCl$_3$); 1H NMR (600 MHz, Benzene-d$_6$) δ 8.26 (ddd, J=4.8, 2.0, 0.9 Hz, 1H), 7.54 (d, J=7.9 Hz, 1H), 6.89 (td, J=7.7, 1.9 Hz, 1H), 6.40 (ddd, J=7.6, 4.8, 1.1 Hz, 1H), 4.25-4.18 (m, 1H), 4.05-3.99 (m, 1H), 3.96-3.91 (m, 1H), 3.79 (dd, J=10.3, 3.3 Hz, 1H), 3.76-3.66 (m, 2H), 3.40 (dd, J=15.0, 2.5 Hz, 1H), 3.06 (dd, J=7.5, 4.1 Hz, 1H), 2.75-2.68 (m, 1H), 2.65 (dd, J=14.9, 10.3 Hz, 1H), 1.97 (ddd, J=13.9, 8.2, 3.6 Hz, 1H), 1.89 (ddd, J=12.8, 7.9, 6.3 Hz, 1H), 1.72 (ddd, J=13.4, 8.4, 4.7 Hz, 1H), 1.56 (ddd, J=13.4, 7.4, 2.8 Hz, 1H), 1.12 (t, J=7.9 Hz, 9H), 1.06-1.03 (s, 12H), 0.99 (s, 9H), 0.94 (t, J=8.0 Hz, 9H), 0.84-0.75 (m, 6H), 0.55-0.49 (m, 6H), 0.25 (s, 3H), 0.24 (s, 3H), 0.12 (s, 3H), 0.11 (s, 3H); IR (neat) v 2953, 2929, 2877, 1707, 1471, 1420, 1250, 1080, 1004, 834, 774, 737; HRMS (ESI) calcd. for $C_{41}H_{81}NNaO_6SSi_4$ [M+Na]$^+$: 850.4754, found 850.4773.

Compound 13

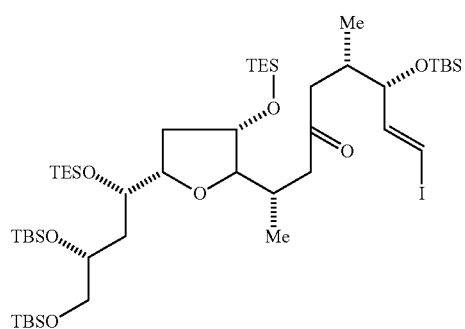

An oven dried 50 mL single-necked flask was charged with FeBr$_2$(SciOPP) (8 mg, 5 mol %), manganese (16.4 mg, 0.3 mmol), copper (I) iodide (28.4 mg, 0.15 mmol), lithium chloride (19 mg, 0.44 mmol) and 1,2-dimethoxyethane (0.5 mL) at room temperature. A solution of thio ester 12 (100 mg, 0.12 mmol) and diiodide 10 (67 mg, 0.14 mmol) in 1,2-dimethoxyethane (0.5 mL) was charged into the above single-necked flask. The reaction mixture was taken out from glove box, cooled to 0° C. and stirred the reaction mixture under nitrogen atmosphere for 15 hours. After completing the reaction florisil (100 mg) was added to the reaction mixture and stirred for 30 min at 0° C. Filtered the reaction mixture through Celite, washed the filter cake with ethyl acetate (10 mL) and concentrated under reduced pressure to afford the crude product which was then purified by flash column chromatography on silica gel to afford 82 mg (64%) of ketone 13 as a viscous colorless liquid. [α]$_D^{23}$ −11.6 (c 1.3, CHCl$_3$); 1H NMR (500 MHz, Benzene-d$_6$) δ 6.39 (dd, J=14.4, 6.2 Hz, 1H), 6.14-6.08 (m, 1H), 4.26-4.19 (m, 1H), 4.06-4.00 (m, 1H), 4.00-3.95 (m, 1H), 3.80 (dd, J=10.3, 3.3 Hz, 1H), 3.77-3.66 (m, 3H), 3.09 (dd, J=8.1, 3.9 Hz, 1H), 3.00 (dd, J=16.8, 2.6 Hz, 1H), 2.72-2.62 (m, 1H), 2.44 (dd, J=16.6, 3.9 Hz, 1H), 2.36-2.15 (m, 3H), 2.03-1.87 (m, 2H), 1.74 (ddd, J=13.4, 8.5, 4.4 Hz, 1H), 1.57 (ddd, J=13.5, 7.1, 2.5 Hz, 1H), 1.13 (t, J=7.9 Hz, 9H), 1.06 (d, J=0.8 Hz, 9H), 1.03-1.00 (m, 12H), 0.97 (t, J=7.9 Hz, 9H), 0.91 (s, 9H), 0.88 (d, J=6.5 Hz, 3H), 0.83-0.77 (m, 6H), 0.55 (q, J=8.1 Hz, 6H), 0.26 (s, 3H), 0.25 (s, 3H), 0.1 (s, 6H),–0.02 (s, 3H),–0.04 (s, 3H); $^{13}$C NMR (125 MHz, Benzene-d$_6$) δ 207.7, 147.3, 86.9, 80.9, 78.4, 76.6, 72.2, 71.9, 70.9, 67.8, 47.3, 44.8, 38.7, 38.6, 34.5, 28.6, 25.9, 25.7, 18.3, 18.1, 18.0, 17.1, 15.8, 7.1, 6.8, 5.5, 4.9,–4.3,–4.6, –4.7,–5.2, –5.4,–5.5; IR (neat) v 2954, 2928, 2856, 1713, 1471, 1462, 1361, 1252, 1078, 1005, 835, 775, 740; HRMS (ESI) calcd. for C$_{48}$H$_{101}$INaO$_7$Si$_5$ [M+Na]$^+$: 1079.5336, found 1079.5275.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims.

Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of preparing a compound of Formula (II-3):

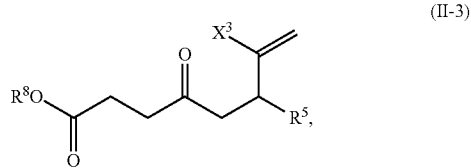

or a salt thereof, the method comprising coupling a compound of Formula (II-1):

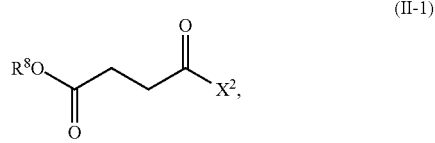

or a salt thereof, with a compound of Formula (II-2):

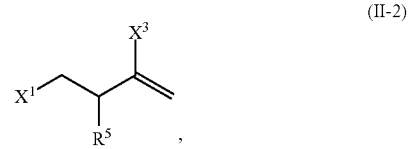

or a salt thereof, wherein:

$X^1$ and $X^3$ are each independently a halogen or a leaving group;

$X^2$ is halogen, a leaving group, or —SR$^S$;

R$^s$ is optionally substituted alkyl, optionally substituted carbocyclyl, optionally substituted aryl, optionally substituted heterocyclyl, or optionally substituted heteroaryl;

$R^5$ is hydrogen, halogen, or optionally substituted alkyl; and $R^8$ is optionally substituted alkyl, optionally substituted carbocyclyl, optionally substituted aryl, optionally substituted heterocyclyl, optionally substituted heteroaryl, optionally substituted acyl, or an oxygen protecting group.

2. The method of claim 1, wherein the compound of Formula (II-3) is the following:

or a salt thereof; the compound of Formula (II-1) is the following:

or a salt thereof; and the compound of Formula (II-2) is the following:

or a salt thereof.

3. The method of claim 1, wherein the step of coupling is carried out in the presence of copper and iron.

4. The method of claim 1, wherein the step of coupling is carried out in the presence of a zirconium complex.

5. The method of claim 1, wherein the step of coupling is carried out in the presence of a lithium salt.

6. The method of claim 1, wherein the step of coupling is carried out in the presence of a reducing metal.

7. The method of claim 1, wherein the step of coupling is carried out in the presence of an iron complex, a copper salt, a lithium salt, and a reducing metal.

8. The method of claim 1, wherein $X^1$ is halogen.

9. The method of claim 1, wherein $X^2$ is $-SR^S$.

10. The method of claim 9, wherein $R^S$ is optionally substituted heteroaryl.

11. A compound having the structure:

or a salt thereof.

12. The method of claim 1 further comprising reacting the compound of Formula (II-3):

(II-3)

or a salt thereof, in the presence of a reagent of formula $R^{P9}OH$, to yield a compound of Formula (III-1):

(III-1)

or a salt thereof; wherein:
 $X^3$ is halogen or a leaving group;
 $R^8$ is optionally substituted alkyl, optionally substituted carbocyclyl, optionally substituted aryl, optionally substituted heterocyclyl, optionally substituted heteroaryl, optionally substituted acyl, or an oxygen protecting group; and
 each $R^{P9}$ is independently hydrogen, optionally substituted alkyl, optionally substituted acyl, or an oxygen protecting group; optionally wherein two $R^{P9}$ groups are joined together with the intervening atoms.

13. The method of claim 12, wherein the compound of Formula (II-3) is the following:

or a salt thereof; the reagent of Formula $R^{P9}OH$ is the following:

or a salt thereof; and the compound of Formula (III-1) is the following:

or a salt thereof.

14. The method of claim 1, wherein the compound of Formula (II-1) is the following:

or a salt thereof.

15. The method of claim 14, wherein the compound of Formula (II-2) is the following:

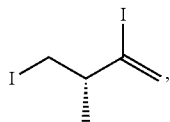

or a salt thereof; and the compound of Formula (II-3) is the following:

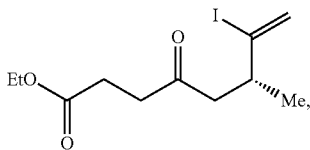

or a salt thereof.

16. The method of claim 14, wherein the compound of Formula (II-2) is the following:

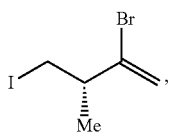

or a salt thereof; and the compound of Formula (II-3) is the following:

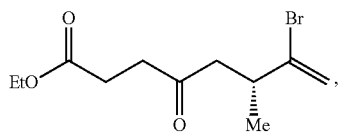

or a salt thereof.

17. The method of claim 3, wherein the iron is an iron (II) or iron (III) complex.

18. The method of claim 3, wherein the iron is an iron complex of the formula:

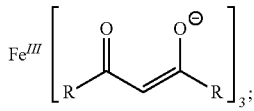

wherein each instance of R is independently optionally substituted alkyl, optionally substituted carbocyclyl, optionally substituted aryl, optionally substituted heteroaryl, or optionally substituted heterocyclyl.

19. The method of claim 18, wherein the iron complex is selected from iron(III) tris(2,2,6,6-tetramethyl-3,5-heptanedionate) (Fe(TMHD)$_3$), iron(III) 1,3-diphenyl-1,3-propanedionate (Fe(DBM)$_3$), and tris(acetylacetonato) iron(III) (Fe(acac)$_3$).

20. The method of claim 3, wherein the iron is an iron complex of the formula: Fe(X)$_2$(ligand); wherein each instance of X is independently halogen; and "ligand" is two phosphine ligands or a bisphosphine ligand.

21. The method of claim 20, wherein the iron complex is selected from iron(II) bromide (1,4-bis(diphenylphosphino) benzene) (FeBr$_2$(dppb)), iron(II) chloride (1,4-bis(diphenylphosphino)benzene) (FeCl$_2$(dppb)), iron(II) bromide (1,2-bis[bis[3,5-di(t-butyl)phenyl]phosphino]benzene) (FeBr$_2$(SciOPP)), iron(II) chloride (1,2-bis[bis[3,5-di(t-butyl)phenyl]phosphino]benzene) (FeCl$_2$(SciOPP)), iron(II) bromide (1,2-bis(diphenylphosphino)ethane) (FeBr$_2$(dppe)), iron(II) chloride (1,2-bis(diphenylphosphino)ethane) (FeCl$_2$(dppe)), FeBr$_2$(PPh$_3$)$_2$, and FeCl$_2$(PPh$_3$)$_2$.

22. The method of claim 3, wherein the iron is an iron complex selected from iron(III) tris(2,2,6,6-tetramethyl-3,5-heptanedionate) (Fe(TMHD)$_3$), iron(II) bromide (1,4-bis(diphenylphosphino)benzene) (FeBr$_2$(dppb)), and iron(II) bromide (1,2-bis[bis[3,5-di(t-butyl)phenyl]phosphino]benzene)(FeBr$_2$(SciOPP).

23. The method of claim 3, wherein the copper is a copper (I) salt or copper (II) salt.

24. The method of claim 3, wherein the copper is a copper salt selected from CuCl, CuBr, CuI, CuCN, copper(I)-thiophene-2-carboxylate (CuTc), CuBr$_2$, and CuCl$_2$.

25. The method of claim 24, wherein the copper salt is CuCl$_2$.

26. The method of claim 5, wherein the lithium salt is selected from LiCl, LiBr, and LiI.

27. The method of claim 26, wherein the lithium salt is LiCl.

28. The method of claim 6, wherein the reducing metal is Zn metal or Mn metal.

29. The method of claim 28, wherein the reducing metal is Mn metal.

30. The method of claim 4, wherein the zirconium complex is di(cyclopentadienyl)zirconium(IV) dichloride (Cp$_2$ZrCl$_2$).

31. The method of claim 7, wherein the step of coupling is carried out in the presence of an iron complex selected from iron(III) tris(2,2,6,6-tetramethyl-3,5-heptanedionate) (Fe(TMHD)3), iron(II) bromide (1,4-bis(diphenylphosphino)benzene) (FeBr$_2$(dppb)), and iron(II) bromide (1,2-bis[bis[3,5-di(t-butyl)phenyl]phosphino]benzene) (FeBr$_2$(SciOPP)); CuCl$_2$; LiCl; and Mn metal.

32. The method of claim 1, wherein the step of coupling is carried out in a solvent.

33. The method of claim 32, wherein the solvent is dimethoxyethane (DME).

34. The method of claim 1, wherein the step of coupling is carried out at a temperature ranging from approximately 0° C. to approximately room temperature, inclusive.

35. The method of claim 34, wherein the strep of coupling is carried out at approximately 0° C.

36. The method of claim 1, wherein:
(i) the step of coupling is carried out in the presence of an iron complex selected from iron(III) tris(2,2,6,6-tetramethyl-3,5-heptanedionate) (Fe(TMHD)$_3$), iron(II) bromide (1,4-bis(diphenylphosphino)benzene) (FeBr$_2$ (dppb)), and iron(II) bromide (1,2-bis[bis[3,5-di(t-butyl)phenyl]phosphino]benzene) (FeBr$_2$(SciOPP); CuCl$_2$; LiCl; and Mn metal;
(ii) the step of coupling is carried out in dimethoxyethane (DME) at approximately 0° C.; and
(ii) $X^2$ is —Cl; $X^1$ is —I; and $X^3$ is —I or —Br.

37. The method of claim 8, wherein $X^1$ is —I.

38. The method of claim 1, wherein $X^2$ is halogen.

39. The method of claim 38, wherein $X^2$ is —Cl.

40. The method of claim 1, wherein $X^3$ is halogen.

41. The method of claim 40, wherein $X^3$ is —I or —Br.

42. The method of claim 1, wherein $R^5$ is $C_{1-6}$ alkyl.

43. The method of claim 42, wherein $R^5$ is methyl.

44. The method of claim 1, wherein $R^8$ is $C_{1-6}$ alkyl.

45. The method of claim 44, wherein $R^8$ is methyl or ethyl.

46. The method of claim 12, wherein the reaction is carried out in the presence of an acid.

47. The method of claim 46, wherein the acid is p-toluenesulfonic acid (p-TsOH).

48. The method of claim 12, wherein the reaction is carried out in the presence of an orthoformate.

49. The method of claim 48, wherein the orthoformate is trimethyl orthoformate.

50. The method of claim 12, wherein the reagent of formula $R^{P9}OH$ is the following:

and in the compound of Formula (III-1) two $R^{P9}$ are joined together with the intervening atoms to form:

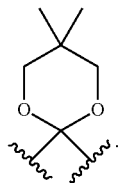 [SMILES: *C1(*)OCC(C)(C)CO1]

51. The method of claim 12, wherein the reaction is carried out in a solvent.

52. The method of claim 51, wherein the solvent is acetonitrile (MeCN).

53. The method of claim 12, wherein the reaction is carried out at approximately room temperature.

54. The method of claim 12, wherein:
   (i) the reagent of formula $R^{P9}OH$ is the following:

(ii) the reaction is carried out in the presence of p-toluenesulfonic acid (p-TsOH) and trimethyl orthoformate; and
   (ii) the reaction is carried out in MeCN at approximately room temperature.

55. The method of claim 12, wherein $X^3$ is halogen.

56. The method of claim 55, wherein $X^3$ is —I.

57. The method of claim 12, wherein $R^5$ is $C_{1-6}$ alkyl.

58. The method of claim 57, wherein $R^5$ is methyl.

59. The method of claim 12, wherein $R^8$ is $C_{1-6}$ alkyl.

60. The method of claim 59, wherein $R^8$ is methyl or ethyl.

* * * * *